(12) United States Patent
Iguchi et al.

(10) Patent No.: US 9,359,647 B2
(45) Date of Patent: Jun. 7, 2016

(54) PROBE FOR DETECTION OF POLYMORPHISM IN EGFR GENE, AMPLIFICATION PRIMER, AND USE THEREOF

(71) Applicant: ARKRAY, Inc., Kyoto (JP)

(72) Inventors: Aki Iguchi, Kyoto (JP); Moeko Ijuin, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 0 days.

(21) Appl. No.: 14/165,530

(22) Filed: Jan. 27, 2014

(65) Prior Publication Data

US 2014/0170657 A1 Jun. 19, 2014

Related U.S. Application Data

(62) Division of application No. 13/285,883, filed on Oct. 31, 2011, now abandoned.

(30) Foreign Application Priority Data

Oct. 29, 2010 (JP) .................................. 2010-244643

(51) Int. Cl.
C12Q 1/68 (2006.01)

(52) U.S. Cl.
CPC ........ *C12Q 1/6886* (2013.01); *C12Q 2600/156* (2013.01)

(58) Field of Classification Search
None
See application file for complete search history.

(56) References Cited

U.S. PATENT DOCUMENTS

| 8,637,245 B2 | 1/2014 | Costa et al. |
| 2008/0261219 A1 | 10/2008 | Whitcombe et al. |
| 2009/0149403 A1 | 6/2009 | MacLachlan et al. |
| 2010/0009360 A1 | 1/2010 | Rosell Costa et al. |
| 2010/0068713 A1* | 3/2010 | Hirai et al. ........................ 435/6 |
| 2011/0244460 A1* | 10/2011 | Hirai et al. ................... 435/6.11 |
| 2013/0323736 A1 | 12/2013 | Whitcombe et al. |
| 2014/0113293 A1 | 4/2014 | Rosell Costa et al. |

FOREIGN PATENT DOCUMENTS

| CN | 101586152 A | 11/2009 |
| EP | 1881079 | 1/2008 |
| EP | 2314717 | 4/2011 |
| EP | 1866438 | 1/2012 |
| JP | 2005-229834 A | 9/2005 |
| JP | 2005-270053 A | 10/2005 |
| JP | 2008-534025 | 8/2008 |
| JP | 2009-544283 | 12/2009 |
| WO | WO 2006/106316 | 10/2006 |
| WO | WO 2008/009740 | 1/2008 |
| WO | 2009/061500 A1 | 5/2009 |
| WO | 2010/071147 A1 | 6/2010 |
| WO | WO 2010071147 A1 * | 6/2010 |
| WO | 01/42486 A1 | 6/2011 |

OTHER PUBLICATIONS

Taylor, Claire. (2009) Mutation scanning using high-resolution melting. Biochemical Society Transactions, 37(2):433-437.*
NM_005228.3 (EGFR NCBI Reference Sequence, GI:41327737, priority to Sep. 28, 2009, 7 pages).*
Willmore-Payne et al. (2008) The Use of EGFR Exon 19 and 21 Unlabeled DNA Probes to Screen for Activating Mutations in Non-Small Cell Lung Cancer. Journal of Biomolecular Techniques, 19:217-224.*
Wong et al. (1987) Increased expression of the epidermal growth factor receptor gene in malignant gliomas is invariably associated with gene amplification. PNAS, 84:6899-6903.*
Molina-Vila et al. (2008) A Sensitive Method for Detecting EGFR Mutations in Non-small Cell Lung Cancer Samples with Few Tumor Cells. Journal of Thoracic Oncology, 3(11):1224-1235.*
Kosaka et al. (2004) Mutations of the Epidermal Growth Factor Receptor Gene in Lung Cancer: Biological and Clinical Implications. Cancer Research, 64, 8919-8923.*
Buck et al. (1999) Design strategies and performance of custom DNA sequencing primers, Biotechniques, 27:528-536.
Caplin et al. (1999) LightCycler TM hybridization probes, Biochemica, 1:5-8.
Crockett et al. (2001) Fluorescein-labeled oligonucleotides for real time PCR: using the inherent quenching of deoxyguanosine nucleotides, Anal. Biochem. 290:89-97.
dbSNP Cluster Report for rs121434568 (obtained from <http://www.ncbi.nlm.nih.gov/projects/SNP/snp_ref.cgi?searchType=adhoc_search&type=rs&rs=rs121434568> on Sep. 10, 2013, 3 pages.
Endo et al. (2005) Epidermal growth factor receptor gene mutation in non-small cell lung cancer using highly sensitive and fast TaqMan PCR assay, Lung Cancer, 50:375-384.
Extended European Search Report issued in the corresponding European Application No. 11187131.5 dated Jan. 9, 2012.
Eun et al. (2000) Simultaneous quantitation of two orchid viruses by the TaqMan real-time RT-PCR. J. Virol. Methods, 87:151-160.
GenBank record NM_005228.3 GI:41327737, *Homo sapiens* epidermal growth factor receptor (erythroblastic leukemia viral (v-erbb) oncogen homolog, avian) (EGFR), transcript variant 1, mRNA. Sep. 29, 2009. Accessed from http://www.ncbi.nlm.nih.gov/nuccore/413277377?sat=13&satkey=5013309 on Nov. 21, 2012. Seven pages.
Harvey et al. (2005) Southern blotting as a diagnostic method in: Walker et al., Medical Biomethods Handbook, New New Jersey, Humana Press, pp. 35-42.
Hill (2005) Conformation-sensitive gel electrophoresis in: Walter et al., Medical Biomethods Handbook, New Jersey, Humana Press, pp. 147-153.
Hoshi et al. (2007) Rapid detection of epidermal growth factor receptor mutations in lung cancer by the SMart-amplification process, Clin. Cancer Res., 13:4974-4983.

(Continued)

*Primary Examiner* — Michele K Joike
*Assistant Examiner* — Neil P Hammell
(74) *Attorney, Agent, or Firm* — Morgan, Lewis & Bockius LLP

(57) ABSTRACT

A polymorphism-detecting probe, an amplification primer and the use thereof are provided to enable simple and highly reliable determination of different polymorphisms in an EGFR gene.

8 Claims, 7 Drawing Sheets

(56) References Cited

OTHER PUBLICATIONS

Li et al. (2007) Bronchial and peripheral murine lung carcinomas induced by T790M-L858R mutant EGFR respond to HKI-272 and rapamycin combination therapy, Cancer Cell, 12:81-93.

Marchetti et al. (2005) EGFR mutations in non-small-cell lung cancer: analysis of a large series of cases and development of a rapid and sensitive method for diagnostic screening with potential implications on pharmacologic treament, J. Clin. Oncol., 23:857-865.

Mitsudomi et al. (2006) Mutations of epidermal growth factor receptor gene predict prolonged survival After gefitinib treatment in patients with non-small-cell lung cancer with postoperative recurrence, J. Clin. Oncol., 23:2513-2520.

Nelson et al. (2005) Lehninger principles of biochemistry, 4th ed., New York: H. Freeman and Co., pp. 297-298.

Office Action issued in corresponding Chinese Patent Application No. 201110348377.2 dated Jul. 10, 2013.

Paez et al. (2004) EGFR mutations in lung cancer: correlation with Clinical Response to gefitinib therapy, Science, 304:1497-1500.

Pao et al. (2005) Acquired resistance of lung adenocarcinomas to gefitinib or erlotinib is associated with a Second mutation in the EGFR kinase domain, PLoS Medi., 2:225-235.

Rozen et al. (2000) Primer3 on the WWW for general users and for biologist programmers. In: Krawetz S., Misener S. (eds) Bioinformatics methods and protocols: methods in molecular biology, Humana Press, Totowa, NJ, pp. 365-389.

Sasaki et al. (2006) L858R EGFR mutation status correlated with clinico-pathological features of Japanese lung cancer, Lung Cancer, 54:103-108.

Taylor et al. (2009) Mutation scanning using high-resolution melting, Biochem. Soc. Trans., 37:433-437.

Willmore-Payne et al. (2006) Detection of epidermal growth factor receptor and human epidermal growth factor receptor 2 activating mutations in lung adenocarcinoma by high-resolution melting amplicon analysis: correlation with gene copy number, protein expression, and hormone receptor expression, Hum. Pathol., 37:755-763.

Willmore-Payne et al. (2008) The use of EGFR exon 19 and 21 unlabeled DNA probes to screen for activating mutations in-non-small cell lunch cancer, J. Biol. Tech., 19:217-224.

Xue et al. (2008) EGFR polymorphism prediction of radiosensitivity of nasopharyngeal carcinoma, J. Cancer Control and Treatment, 21:32-37 (partial machine translation).

Yatabe et al. (2006) A rapid, sensitive assay to detect EGFR mutation in small biopsy specimens from lung cancer, J. Mol. Diagn., 8:335-341.

Office Action issued in corresponding Chinese Patent Application No. 201110348377.2 dated Mar. 7, 2014.

Office Action issued in related Japanese Patent Application No. 2011/237880 dated May 12, 2015 (with partial translation).

Sasaki et al., "EGFR Mutation Status in Japanese Lung Cancer Patients: Genotyping Analysis Using LightCycler," Clinical Cancer Research, 11: 2924-2929 (2005).

"Idenshi Kogaku Jikken Noto," Yodosha Co., Ltd, Analysis of Gene [from sequence to microarray], 2: 14 (1997) (with partial translation).

Office Action issued in corresponding European Patent Application No. 11187131.5 dated Jul. 14, 2015.

* cited by examiner

PROBE FOR DETECTION OF POLYMORPHISM IN EGFR GENE, AMPLIFICATION PRIMER, AND USE THEREOF

SEQUENCE LISTING SUBMISSION VIA EFS-WEB

A computer readable text file, entitled "SequenceListing.txt," created on or about Oct. 26, 2011 with a file size of about 19 kb contains the sequence listing for this application and is hereby incorporated by reference in its entirety.

BACKGROUND OF THE INVENTION

The present invention relates to a probe configured to detect a polymorphism in an EGFR gene, an amplification primer, and the use thereof.

Epidermal growth factor receptor (EGFR) is the tyrosine kinase receptor for epidermal growth factor (EGF). EGFR is associated with a high frequency of expression in many solid tumors, and overexpression is known to be related to the malignancy or prognosis of a cancer. In this regard, gefitinib or the like that is an EGFR tyrosine kinase inhibitor (EGFR-TKI) is used as a therapeutic agent for cancers. However, a patient may exhibit an improvement in the effect of gefitinib in shrinking a tumor, or resistance to gefitinib may preclude a therapeutic effect. In recent years, the relationship between the sensitivity to this type of therapeutic agent and EGFR mutations has been elucidated. (PLoS Medicine, 2005. Vol. 2, No. 3, p. 225-235, and Journal of Clinical Oncology. 2005, Vol. 23, No. 11, p. 2513-2520).

These mutations are known to include a substitution mutation at position 790 and position 858 in EGFR, and a deletion mutation at exon 19 in the EGFR gene (PLoS Medicine, 2005, Vol. 2. No. 3, p. 225-235, and Journal of Clinical Oncology, 2005, Vol. 23. No. 1, p. 2513-2520). The mutation at position 790 is a mutation in which threonine (T) that is the amino acid at position 790 in EGFR is substituted by methionine (M). In the partial sequence of the EGFR gene illustrated in SEQ ID NO: 21, the cytosine (c) nucleotide at position 347 is substituted by thymin (t). The mutation at position 858 is a mutation in which leucine (L) that is the amino acid at position 858 in EGFR is substituted by arginine (R). In the partial sequence of the EGFR gene illustrated in SEQ ID NO: 1, the thymin (t) nucleotide at position 261 is substituted by guanine (g). The deletion mutation at exon 19 in the EGFR gene is a mutation in which several continuous nucleotides or more than ten continuous nucleotides are deleted in exon 19, and in the partial sequence of the EGFR gene illustrated in SEQ ID NO: 2, for example, any of the nucleotides at positions 112-164 are deleted. Therefore in the EGFR gene, there is the possibility of more effective and patient-specific cancer therapy if the presence or absence of a mutation (polymorphism) is detected to thereby evaluate sensitivity to gefitinib prior to therapy.

Various methods have been reported into relation to detection of polymorphisms in genes, and for example, include a method such as PCR restriction fragment length polymorphism (PCR-RFLP).

However, the PCR-RFLP method is labor intensive and in the event that an amplification product becomes dispersed, there is a risk of contamination of a separate subsequent reaction. These problems are related to difficulties associated with automatization of detection of polymorphisms.

In recent years, these problems have resulted in detection using melting curve analysis (Tm analysis) as a method of detection of gene polymorphism. In this method, a hybrid (double-stranded DNA) is formed from target single-stranded DNA from a detection sample and a probe that is complementary to the sequence of interest including the gene polymorphism that is the target of detection. Then a heating process is executed in relation to the hybridization product. The dissociation (melting) of the hybrid resulting from the temperature increase is detected by signal measurement using absorbance or the like to thereby determine the presence or absence of a target polymorphism by determining a Tm value based on the detection result. A Tm value increases corresponding to high sequence identity in the hybridization product, and decreases corresponding to low sequence identity. Consequently, a Tm value (evaluation reference value) can be obtained in advance in relation to the hybridization product of the sequence of interest including the gene polymorphism that is the target of detection and the complementary probe, and the Tm value (measurement value) of the target single-stranded DNA from a detection sample and the probe is measured. When the measurement value is the same as the evaluation reference value, it is determined that the target polymorphism is present in the target DNA. When the measurement value is lower than the evaluation reference value, it is determined that the target polymorphism is not present in the target DNA.

A melting curve may be obtained by performing the Tm analysis described herein. The melting curve may have a horizontal axis showing the temperature (° C.) during measurement, and a vertical axis showing the change in the fluorescent intensity.

"Tm value" is the temperature (dissociation temperature: Tm) at which double-stranded nucleic acid dissociates, and generally is defined as the temperature at which the absorbance at 260 nm reaches 50% of the total increase in absorbance. That is to say, when a solution containing double-stranded nucleic acid, for example double-stranded DNA, is heated, the absorbance at 260 nm increases. The increase results from the breakage of hydrogen bonds between the strands in the double-stranded DNA resulting from the heating and the dissociation into single-stranded DNA (DNA melting). When all double-stranded DNA dissociates to form single-stranded DNA, the absorbance exhibits approximately a 1.5 increase of the absorbance when commencing heating (absorbance when only double-stranded DNA is present). In this manner, completion of melting can be determined. The Tm value is set based on this phenomenon.

However, a detection method using this type of Tm analysis determines at least a one-nucleotide difference on the basis of the Tm value, and therefore when there is a plurality of genetic polymorphisms, the analysis of a single sample is extremely labor-intensive.

BRIEF SUMMARY OF THE INVENTION

For the above reasons, the detection of polymorphisms in an EGFR gene is important in relation to the selection of a method of treatment for a disease. Therefore, it is an object of the present invention to provide a polymorphism-detection probe configured to enable determination of a polymorphism comprising a one-nucleotide difference in a simple manner and with superior reliability, and to a method of detection of a polymorphism.

To achieve the above object, the probe according to some embodiments of the present invention is a labeled probe comprising at least one oligonucleotide selected from the group consisting of oligonucleotides P1. P3, P5-P7, and P15 to P18.

(P1) An oligonucleotide comprising a sequence at least about 85% identical to a complementary nucleotide sequence of 11 to 50 nucleotides to nucleotides 251 to 261 of SEQ ID NO: 1:

(P3) An oligonucleotide comprising a sequence at least about 85% identical to a complementary nucleotide sequence of 5 to 50 nucleotides to nucleotides 257 to 261 of SEQ ID NO: 1;

(P5) An oligonucleotide comprising a sequence at least about 85% identical to a nucleotide sequence of 9 to 50 nucleotides comprising nucleotides 104 to 112 of SEQ ID NO: 2;

(P6) An oligonucleotide comprising a sequence at least about 85% identical to a nucleotide sequence of 16 to 50 nucleotides comprising nucleotides 104 to 119 of SEQ ID NO: 2;

(P7) An oligonucleotide comprising a sequence at least about 85% identical to a nucleotide sequence of 10 to 50 nucleotides comprising nucleotides 136 to 145 of SEQ ID NO: 3;

(P15) An oligonucleotide comprising a sequence at least about 85% identical to a complementary nucleotide sequence of 6 to 50 nucleotides to nucleotides 259 to 264 of SEQ ID NO: 1;

(P16) An oligonucleotide comprising a sequence at least about 85% identical to a complementary nucleotide sequence of 5 to 50 nucleotides to nucleotides 258 to 262 of SEQ ID NO: 1;

(P17) An oligonucleotide comprising a sequence at least about 85% identical to a nucleotide sequence of 16 to 50 nucleotides comprising nucleotides 249 to 264 of SEQ ID NO: 1; and (P18) An oligonucleotide comprising a sequence at least about 85% identical to a nucleotide sequence of 8 to 50 nucleotides comprising nucleotides 257 to 264 of SEQ ID NO: 1.

In further embodiments, the oligonucleotide P1 is an oligonucleotide comprising a complementary nucleotide sequence of 11 to 50 nucleotides to nucleotides 251 to 261 of SEQ ID NO: 1:

the oligonucleotide P3 is an oligonucleotide comprising a complementary nucleotide sequence of 5 to 50 nucleotides to nucleotides 257 to 261 of SEQ ID NO: 1:

the oligonucleotide P5 is an oligonucleotide comprising a nucleotide sequence of 9 to 50 nucleotides comprising nucleotides 104 to 112 of SEQ ID NO: 2:

the oligonucleotide P6 is an oligonucleotide comprising a nucleotide sequence of 16 to 50 nucleotides comprising nucleotides 104 to 119 of SEQ ID NO: 2;

the oligonucleotide P7 is an oligonucleotide comprising a nucleotide sequence of 10 to 50 nucleotides comprising nucleotides 136 to 145 of SEQ ID NO: 3;

the oligonucleotide P15 is an oligonucleotide comprising a complementary nucleotide sequence of 6 to 50 nucleotides to nucleotides 259 to 264 of SEQ ID NO: 1;

the oligonucleotide P16 is an oligonucleotide comprising a complementary nucleotide sequence of 5 to 50 nucleotides to nucleotides 258 to 262 of SEQ ID NO: 1;

the oligonucleotide P17 is an oligonucleotide comprising a nucleotide sequence of 16 to 50 nucleotides comprising nucleotides 249 to 264 of SEQ ID NO: 1; and the oligonucleotide P18 is an oligonucleotide comprising a nucleotide sequence of 8 to 50 nucleotides comprising nucleotides 257 to 264 of SEQ ID NO: 1.

The method of detecting a polymorphism according to some embodiments of the present invention is a method of detecting a polymorphism in an EGFR gene in a sample using the probe according to the present invention, comprising adding to the sample the probe according to the present invention, obtaining a melting curve for the probe, and determining the melting temperature of the probe from the melting curve, wherein the melting temperature indicates the presence of the polymorphism in the EGFR gene.

A determination method according to the present invention is a method configured to determine efficacy of EGFR-TKI or a resistance to EGFR-TKI and is characterized by including a step of detecting a polymorphism in an EGFR gene using the method of the present invention and a step of determining efficacy or a resistance to EGFR-TKI based on the presence or absence of the polymorphism.

A kit according to some embodiments of the present invention is a reagent kit for detecting a polymorphism in an EGFR gene and includes the probe according to the present invention.

A primer according to some embodiments of the present invention is a primer comprising or consisting of a sequence selected from the group consisting of oligonucleotides P8 to P13.

(P8) An oligonucleotide of 10 to 50 nucleotides homologous to nucleotides 224 to 233 of SEQ ID NO: 1, and in which the 3' terminal is the nucleotide C at position 233.

(P9) An oligonucleotide of 10 to 50 nucleotides complementary to nucleotides 284 to 293 of SEQ ID NO: 1, and in which the 3' terminal is the nucleotide C complementary to the nucleotide G at position 284.

(P10) An oligonucleotide of 10 to 50 nucleotides complementary to nucleotides 290 to 299 of SEQ ID NO: 1, and in which the 3' terminal is the nucleotide C complementary to the nucleotide G at position 290.

(P11) An oligonucleotide of 10 to 50 nucleotides homologous to nucleotides 86 to 95 of SEQ ID NO: 2, and in which the 3' terminal is the nucleotide G at position 95.

(P12) An oligonucleotide of 10 to 50 nucleotides homologous to nucleotides 64 to 73 of SEQ ID NO: 2, and in which the 3' terminal is the nucleotide C at position 73.

(P13) An oligonucleotide of 1 to 50 nucleotides complementary to nucleotides 155 to 164 of SEQ ID NO: 2, and in which the 3' terminal is the nucleotide C complementary to the nucleotide G at position 155.

The method for detecting a polymorphism according to some embodiments of the present invention enables simple and highly reliable determination of a polymorphism in an EGFR gene by use of the probe for detecting a polymorphism according to the present invention. More specifically, even when the target polymorphism coexists in a mutant EGFR gene and a wild-type EGFR gene in a sample, the wild-type and mutant polymorphisms can be determined in a simple manner and with high reliability. Furthermore, the primer according to the present invention enables specific amplification of the domain including the polymorphism in the EGFR gene. In this manner, according to the present invention, since the polymorphism in the EGFR gene can be amplified and determined in a simple manner with high reliability, the detection results for example can be reflected in the selection of a regime of treatment for a disease as described above. For example, the efficacy of or resistance to EGFR-TKI of gefitinib and the like can be determined. Furthermore, the present invention enables application to the detection of a polymorphism in an EGFR gene in diverse areas including biochemistry in addition to medical fields.

DETAILED DESCRIPTION OF THE INVENTION

Figure 1:
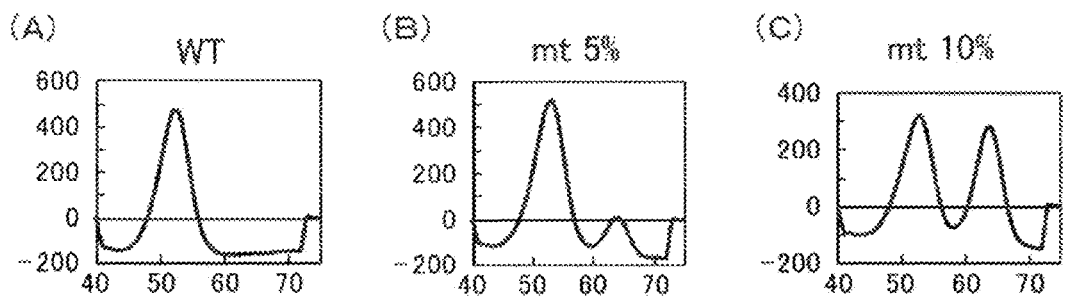
FIG. 1 depicts graphs (A)-(C) illustrating the results of Tm analysis of a reaction solution using different samples according to example 1 of the present invention.

In the present invention, a polymorphism of a gene means a diversity at one or a plurality of gene loci generated for example by mutation. The mutation includes for example, a substitution, deletion, insertion, or addition mutation.

The EGFR gene includes the partial sequence of SEQ ID NOs: 1, 2 and 21 that have been registered respectively as illustrated below in relation to the following GenHtank Accession Numbers.
(SEQ ID NO: 1)
  NT_033968
Nucleotide sequence of positions 4848624-4849033
(SEQ ID NO: 2)
  NT_033968.6

Nucleotide sequence of positions 4831717-4832003
(SEQ ID NO: 21)
  NG_007726
Nucleotide sequence of positions 167001-168020

In the present invention, a polymorphism being the target of detection in an EGFR gene includes the following polymorphisms for example.

A polymorphism of the nucleotide (k) at position 261 in the partial sequence of the EGFR gene of SEQ ID NO: 1.

A polymorphism of at least one of the nucleotides at positions 104-133 in the partial sequence of the EGFR gene of SEQ ID NO: 2.

A polymorphism of at least one of the nucleotides at positions 130-164 in the partial sequence of the EGFR gene of SEQ ID NO: 2.

A polymorphism of the nucleotide (y) at position 347 in the partial sequence of the EGFR gene of SEQ ID NO: 21.

The polymorphism in SEQ ID NO: 1 is hereinafter termed "polymorphism 858 of EGFR exon 21," the polymorphism in SEQ ID NO: 2 is hereinafter termed the "EGFR exon 19 polymorphism", and the polymorphism in SEQ ID NO: 21 is hereinafter termed "EGFR 790 polymorphism." The polymorphisms are respective present in wild and mutant variant. In each polymorphism the wild-type EGFR gene is termed the wild-type gene and the mutant-type EGFR gene is termed the mutant-type gene.

The polymorphism in nucleotide (k) at position 261 in SEQ ID NO: 1 is thymin (t) in the wild-type, and guanine (g) in the mutant-type. The amino acid at position 858 in EGFR in the wild-type is leucine (L), and the amino acid at position 858 in EGFR in the mutant-type is arginine (R).

In the present invention, the expression "EGFR exon 21 L858R" means a mutation at exon 21 in the EGFR gene, and that the mutation on the codon 858 is a mutation of the amino acid from leucine to arginine. In the present invention, the expression "mutant-type of EGFR exon 21" means "EGFR exon 21 L858R." The nucleotide sequence in the EGFR exon 21 in the present invention means the nucleotide sequence in positions 4848624-4849033 of GenBank Accession No. NT_033968. The EGFR exon 21 L858R mutation denotes the mutation from thymin (T) to guanine (G) of the nucleotide at position 4848884 shown in (GenBank Accession No. NT_033968.

The polymorphism in the nucleotides at positions 104 to 164 in SEQ ID NO: 2 for example is the polymorphism as illustrated in Table 1 below (reference is made to Journal of Clinical Oncology, 2005, Vol. 23, No. 11, p. 2513-2520). In Table 1, the polymorphism 1 is a wild variant. The nucleotide sequence of polymorphism 1 below corresponds to the oligonucleotide at positions 104 to 164 in SEQ ID NO: 2. In Table 1 below, the polymorphisms 2 to 18 are a mutant variant (exon 19 deletion mutation) in which at least one nucleotide is deleted in the domain of positions 112 to 164 in SEQ ID NO: 2. Of those polymorphisms, polymorphisms 2 to 17 are a mutant variant in which at least one nucleotide is deleted in the domain of positions 122 to 132 in SEQ ID NO: 2, and more specifically, in which a plurality of nucleotides are deleted in the domain of positions 112 to 140. The polymorphism 18 is a mutant variant in which the nucleotides at positions 137 to 151 in SEQ ID NO: 2 are deleted. In the polymorphisms 2 to 18 in Table 1, the symbol "-" means that the nucleotide at the position corresponding to polymorphism 1 is deleted.

TABLE 1

| Polymorphism | | 104 | 111 | 121 | 131 | 141 | 151 | 161 |
|---|---|---|---|---|---|---|---|---|
| WT | 1 | CCCGTCG | CTATCAAGGA | ATTAAGAGAA | GCAACATCTC | CGAAAGCCAA | Caaggaaatc | ctcg |
| MT | 2 | CCCGTCG | CTATCAA--- | ---------- | --AACATCTC | CGAAAGCCAA | C--------- | ---- |
|  | 3 | CCCGTCG | CTATCAAG-- | ---------- | ---ACATCTC | CGAAAGCCAA | -aaggaaatc | ctcg |
|  | 4 | CCCGTCG | CTATCAAGGA | A--------- | cCAACATCTC | CGAAAGCCAA | Caaggaaatc | ctcg |
|  | 5 | CCCGTCG | CTATCAAGGA | AT-------- | -------CTC | CCAAAGCCAA | Caaggaaate | ctcg |
|  | 6 | CCCGTCG | CTATCAAGGA | AT-------- | ---------- | CGAAAGCCAA | Caaggaaatc | ctcg |
|  | 7 | CCCGTCG | CTATCAAGGA | A--------- | ---cCATCTC | CGAAAGCCAA | Caaggaaatc | ctcg |
|  | 8 | CCCGTCG | CTATCAAGGA | A--------- | ---------C | CGAAAGCCAA | Caaggaaatc | ctcg |
|  | 9 | CCCGTCG | CTATCAAGG | ---------- | -------tTC | CGAAAGCCAA | Caaggaaatc | ctcg |
|  | 10 | CCCGTCG | CTATCAAGGA | AT-------- | ----CATCTC | CGAAAGCCAA | Caaggaaatc | ctcg |
|  | 11 | CCCGTCG | CTATCAAGGA | AT-------- | ---------- | CGAAAGCCAA | Caaggaaatc | ctcg |
|  | 12 | CCCGTCG | CTATCAAGGA | A--------- | ---------C | aGAAAGCCAA | Caaggaaatc | ctcg |
|  | 13 | CCCGTCG | CTATCAAGG- | ---------- | ----tATCTC | CGAAAGCCAA | Caaggaaatc | ctcg |
|  | 14 | CCCGTCG | CTATCAAGGt | ---------- | --------TC | CGAAAGCCAA | Caaggaaatc | ctcg |
|  | 15 | CCCGTCG | CTATCAA--- | ---------- | ----AaTCTC | CGAAAGCCAA | Caaggaaatc | ctcg |
|  | 16 | CCCGTCG | C--------A | ATTAAGAt--- | -----ATCTC | CCAAAGCCAA | Caaggaaatc | ctcg |
|  | 17 | CCCGTCG | CTATCAAGGA | A--------- | -CAA-----C | CGAAAGCCAA | Caaggaaatc | ctcg |
|  | 18 | CCCGTCG | CTATCAAGGA | ATTAAGAGAA | GCAACA---- | ---------- | -aaggaaatc | ctcg |

※The sequences 1-18 are respectively shown as SEQ ID NOs: 29-31, 34-48.

When at least one of the above two-site polymorphisms in an EGFR gene is the above type of mutant-type variant, it can be determined for example that there is a strong possibility of resistance to EGFR-TKI of gefitinib or the like.

The nucleotide (y) in the wild-type variant at position 347 of SEQ ID NO: 21 is cytosine (c), and in this case, the amino acid at position 790 in EGFR is threonine (T). The mutant-type variant is thymin (t), and in this case, the amino acid at position 790 in EGFR is methionine (M). When the polymorphism in the EGFR gene is the above type of mutant-type variant, it is possible to determine for example a possibility of resistance to EGFR-TKI of gefitinib or the like.

In the present invention, "a sequence having sequence identity" is a sequence for example, at least about 75%, 80%, 85%, 86%, 87%, 88%, 89%, 90%, 91%, 92%, 93%, 94%, 95%, 96%, 97%, 98%, 99% or 100% identical to a specific sequence. For example, the identity may be at least 85%, at least 90%, at least 95%, at least 96%, at least 97%, at least 98%, at least 99%, or 100%. That is, in the present invention, the sequence having sequence identity may be a sequence configured from the specific nucleotide sequence described above (the sequence having 100% sequence identity) or a sequence in which substitution, deletion, insertion, and/or addition of at least one nucleotide is applied to the specific nucleotide sequence (the sequence having sequence identity of at least 80% and less than 100%, for example) (hereinafter, the same applies). As used herein, "identity" is a measure of the identity of nucleotide sequences or amino acid sequences (e.g. sequences of the probes and primers described herein) compared to a reference nucleotide or amino acid sequence. In general, the sequences are aligned so that the highest order match is obtained. "Identity" per se has an art-recognized meaning and can be calculated using well known techniques.

Identity or percent identity at the nucleotide or amino acid sequence level can be determined by BLAST (Basic Local Alignment Search Tool) analysis using the algorithm employed by the programs blastp, blastn, blastx, tblastn, and tblastx (Altschul et al. (1997), Nucleic Acids Res. 25, 3389-3402, and Karlin et al. (1990), Proc. Natl. Acad. Sci. USA 87, 2264-2268, both fully incorporated by reference), which are tailored for sequence similarity searching. The approach used by the BLAST program is to first consider similar segments, with and without gaps, between a query sequence and a database sequence, then to evaluate the statistical significance of all matches that are identified, and finally to summarize only those matches which satisfy a preselected threshold of significance. For a discussion of basic issues in similarity searching of sequence databases, see Altschul et al. (1994), Nature Genetics 6, 119-129, which is fully incorporated by reference. The search parameters for histogram, descriptions, alignments, expect (i.e., the statistical significance threshold for reporting matches against database sequences), cutoff, matrix, and filter (low complexity) can be at the default settings. The default scoring matrix used by blastp, blastx, tblastn, and tblastx is the BLOSUM62 matrix (Henikoff et al. (1992). Proc. Natl. Acad. Sci. USA 89, 10915-10919, fully incorporated by reference), recommended for query sequences over 85 in length (nucleotide bases or amino acids).

For blastn, designed for comparing nucleotide sequences, the scoring matrix is set by the ratios of M (i.e., the reward score for a pair of matching residues) to N (i.e., the penalty score for mismatching residues), wherein the default values for M and N can be +5 and −4, respectively. Four blastn parameters can be adjusted as follows: Q=10 (gap creation penalty); R=10 (gap extension penalty); wink=1 (generates word hits at every winkth position along the query); and gapw=16 (sets the window width within which gapped alignments are generated). The equivalent Blastp parameter settings for comparison of amino acid sequences can be: Q=9: R=2; wink=1; and gapw=32. A Bestfit comparison between sequences, available in the GCG package version 10.0, can use DNA parameters GAP=50 (gap creation penalty) and LEN=3 (gap extension penalty), and the equivalent settings in protein comparisons can be GAP=8 and LEN=2.

The site that generates the polymorphism described above, that is to say, the site on the sense strand and the site on the complementary anti-sense strand are termed the "detection site," and the domain that includes the detection site and enables hybridization with the probe for detection of the polymorphism is termed the "hybridizing domain or the detection sequence". The detection sequence in which the detection site is a wild-type variant is termed a "wild-type detection sequence" and a detection sequence in which the detection site is a mutant-type variant is termed a "mutant-type detection sequence."

In the present invention, the probe for detection of the EGFR 858 polymorphism (t/g) is termed an "EGFR 858 probe", the probe for detection of the exon 19 polymorphism is termed an "exon 19 probe," and the probe for detection of the EGFR 790 polymorphism (c/t) is termed an "EGFR 790 probe."

As used herein a "probe" is defined as a nucleic acid, capable of binding to a target nucleic acid of complementary nucleotide sequence through one or more types of chemical bonds, usually through complementary base pairing, usually through hydrogen bond formation. As used herein, a probe may include natural (i.e. A, G, U, C or T) or modified nucleotides (e.g. 7-deazaguanosine, inosine, etc.). In addition, the nucleotides in probes may be joined by a linkage other than a phosphodiester bond, so long as it does not interfere with hybridization. Thus, probes may be peptide nucleic acids in which the constituent nucleotides are joined by peptide bonds rather than phosphodiester linkages.

In the detection sequence, the probe that hybridizes with the wild-type detection sequence stronger than with the mutant-type detection sequence is termed as a "wild-type probe." In the detection sequence, the probe that hybridizes with the mutant-type detection sequence stronger than with the wild-type detection sequence is termed as a "mutant-type probe." The "strength of hybridization" can be expressed, for example, by the relationship of the Tm value. Specifically, the "strength of hybridization" can be expressed by the high-low relationship between the Tm value of a double-stranded nucleic acid composed of a probe and a wild-type detection sequence and the Tm value of a double-stranded nucleic acid composed of the probe and a mutant-type detection sequence. That is, the wild-type probe shows a higher Tm value with the wild-type detection sequence than with the mutant-type detection sequence. On the other hand, the mutant-type probe shows a higher Tm value with the mutant-type detection sequence than with the wild-type detection sequence.

With respect to "shows a higher Tm value," it is applicable as long as the difference between the peaks in the respective Tm values can be detected. Specifically, the difference between the Tm values may be at least 3° C., at least 4° C., or at least 5° C. The upper limit of the difference between the Tm values is not limited at all, and is, for example, 30° C.

In the present invention, the amplification domain in the EGFR gene for example may be a domain in the sense strand of the EGFR gene, may be a domain in the corresponding anti-sense strand, or may be both such domains.

In the present invention, the terminal of the nucleotide sequence means the nucleotide on furthest 5' or 3' end of the nucleotide sequence. Alternatively, the 5' terminal domain is a domain of a number of nucleotides from the 5' terminal of the nucleotide sequence, and the 3' terminal domain is a domain of a number of nucleotides from the 3' terminal of the nucleotide sequence. A number of nucleotides is, for example, 1 nucleotide to 10 nucleotides from the terminal. In the present invention, a nucleotide at the Zth position (Z being a positive integer) from the terminal of the nucleotide sequence is a sequence that takes the terminal nucleotide to be the $1^{st}$ position.

"Probe for Detection of Polymorphism"

(1) EGFR 858 Probe

The probe for detection of a polymorphism according to the present invention as described above is a labeled probe capable of detecting a genetic mutation in EGFR exon 21 L858R and comprises a sequence at least about 75%, 80%, 85%, 86%, 87%, 88%, 19%, 90%, 91%, 92%, 93%, 94%, 95%, 96%, 97%, 98%, 99% or 100% identical to at least one of the following P1, P3, and P15-P18 oligonucleotides.

(P1) An oligonucleotide comprising or consisting of a sequence at least about 85% identical to a complementary nucleotide sequence of 11 to 50 nucleotides to nucleotides 251 to 261 of SEQ ID NO: 1:

(P3) An oligonucleotide comprising or consisting of a sequence at least about 85% identical to a complementary nucleotide sequence of 5 to 50 nucleotides to nucleotides 257 to 261 of SEQ ID NO: 1;

(P5) An oligonucleotide comprising or consisting of a sequence at least about 85% identical to a nucleotide sequence of 9 to 50 nucleotides comprising or consisting of nucleotides 104 to 112 of SEQ ID NO: 2:

(P6) An oligonucleotide comprising or consisting of a sequence at least about 85% identical to a nucleotide sequence of 16 to 50 nucleotides comprising or consisting of nucleotides 104 to 119 of SEQ ID NO: 2:

(P7) An oligonucleotide comprising or consisting of a sequence at least about 85% identical to a nucleotide sequence of 10 to 5 (nucleotides comprising or consisting of nucleotides 136 to 145 of SEQ ID NO: 3;

(P15) An oligonucleotide comprising or consisting of a sequence at least about 85% identical to a complementary nucleotide sequence of 6 to 50 nucleotides to nucleotides 259 to 264 of SEQ ID NO: 1;

(P16) An oligonucleotide comprising or consisting of a sequence at least about 85% identical to a complementary nucleotide sequence of 5 to 50 nucleotides to nucleotides 258 to 262 of SEQ ID NO: 1:

(P17) An oligonucleotide comprising or consisting of a sequence at least about 85% identical to a nucleotide sequence of 16 to 50 nucleotides comprising or consisting of nucleotides 249 to 264 of SEQ ID NO: 1; and (P18) An oligonucleotide comprising or consisting of a sequence at least about 85% identical to a nucleotide sequence of 8 to 50 nucleotides comprising or consisting of nucleotides 257 to 264 of SEQ ID NO: 1.

The probe according to additional embodiments of the present invention may include at least one of the following P1, P3, P5-P7, and P15-P18 oligonucleotides.

(P1) An oligonucleotide comprising or consisting of a sequence at least about 75%, 80%, 85%, 86%, 87%, 88%, 89%, 90%, 91%, 92%, 93%, 94%, 95%, 96%, 97%, 98%, 99% or 100% identical to a complementary nucleotide sequence of 11 to 50 nucleotides to nucleotides 251 to 261 of SEQ ID NO: 1;

(P3) An oligonucleotide comprising or consisting of a sequence at least about 75%, 80%, 85%, 86%, 87%, 88%, 89%, 90%, 91%, 92%, 93%, 94%, 95%, 96%, 97%, 98%, 99% or 100% identical to a complementary nucleotide sequence of 5 to 50 nucleotides to nucleotides 257 to 261 of SEQ ID NO: 1;

(P5) An oligonucleotide comprising or consisting of a sequence at least about 75%, 80%, 85%, 86%, 87%, 88%, 89%, 90%, 91%, 92%, 93%, 94%, 95%, 96%, 97%, 98%, 99% or 100% identical to a nucleotide sequence of 9 to 50 nucleotides comprising nucleotides 104 to 12 of SEQ ID NO: 2;

(P6) An oligonucleotide comprising or consisting of a sequence at least about 75%, 801%, 85%, 86%, 87%, 88%, 89%, 90%, 91%, 92%, 93%, 94%, 95%, 96%, 97%, 98%, 99% or 100% identical to a nucleotide sequence of 16 to 50 nucleotides comprising nucleotides 104 to 119 of SEQ ID NO: 2:

(P7) An oligonucleotide comprising or consisting of a sequence at least about 75%, 80%, 85%, 86%, 87%, 88%, 89%, 90%, 91%, 92%, 93%, 94%, 95%, 96%, 97%, 98%, 99% or 100% identical to a nucleotide sequence of 10 to 50 nucleotides comprising nucleotides 136 to 145 of SEQ ID NO: 3:

(P15) An oligonucleotide comprising or consisting of a sequence at least about 75%, 80%, 85%, 86%, 87%, 88%, 89%, 90%, 91%, 92%, 93%, 94%, 95%, 96%, 97%, 98%, 99% or 100% identical to a complementary nucleotide sequence of 6 to 50 nucleotides to nucleotides 259 to 264 of SEQ ID NO: 1:

(P16) An oligonucleotide comprising or consisting of a sequence at least about 75%, 80%, 85%, 86%, 87%, 88%, 89%, 90%, 91%, 92%, 93%, 94%, 95%, 96%, 97%, 98%, 99% or 100% identical to a complementary nucleotide sequence of 5 to 50 nucleotides to nucleotides 258 to 262 of SEQ ID NO: 1:

(P17) An oligonucleotide comprising or consisting of a sequence at least about 75%, 80%, 85%, 86%, 87%, 88%, 89%, 90%, 91%, 92%, 93%, 94%, 95%, 96%, 97%, 98%, 99% or 100% identical to a nucleotide sequence of 16 to 50 nucleotides comprising nucleotides 249 to 264 of SEQ ID NO: 1; and (P18) An oligonucleotide comprising or consisting of a sequence at least about 75%, 80%, 85%, 86%, 87%, 88%, 89%, 90%, 91%, 92%, 93%, 94%, 95%, 96%, 97%, 98%, 99% or 100% identical to a nucleotide sequence of 8 to 50 nucleotides comprising nucleotides 257 to 264 of SEQ ID NO: 1.

The probe according to yet additional embodiments of the present invention may include at least one of the following P1, P3, P5-P7, and P15-P18 oligonucleotides.

(P1) An oligonucleotide of at least 11, 15, 20, 25, 30, 35, 40, 45, or 50 nucleotides comprising or consisting of a complementary nucleotide sequence to a sequence at least about 75%, 80%, 85%, 86%, 87%, 88%, 89%, 90%, 91%, 92%, 93%, 94%, 95%, 96%, 97%, 98%, 99% or 100% identical to nucleotides 251 to 261 of SEQ ID NO: 1:

(P3) An oligonucleotide of at least 5, 10, 15, 20, 25, 30, 35, 40, 45, or 50 nucleotides comprising or consisting of a complementary nucleotide sequence to a sequence at least about 75%, 80%, 85%, 86%, 87%, 88%, 89%, 90%, 91%, 92%, 93%, 94%, 95%, 96%, 97%, 98%, 99% or 100% identical to nucleotides 257 to 261 of SEQ ID NO: 1;

(P5) An oligonucleotide of at least 9, 15, 20, 25, 30, 35, 40, 45, or 50 nucleotides comprising or consisting of a sequence at least about 75%, 80%, 85%, 86%, 87%, 88%, 89%, 90%, 91%, 92%, 93%, 94%, 9, 95%, 96%, 97%, 98%, 99% or 100% identical to nucleotides 104 to 112 of SEQ ID NO: 2;

(P6) An oligonucleotide of at least 16, 20, 25, 30, 35, 40, 45, or 50 nucleotides comprising or consisting of a sequence at least about 75%, 80%, 85%, 86%, 87%, 88%, 89%, 90%, 91%, 92%, 93%, 94%, 95%, 96%, 97%, 98%, 99% or 100% identical to nucleotides 104 to 119 of SEQ ID NO: 2:

(P7) An oligonucleotide of at least 10, 15, 20, 25, 30, 35, 40, 45, or 50 nucleotides comprising or consisting of a sequence at least about 75%, 80%, 85%, 86%, 87%, 88%, 89%, 90%, 91%, 92%, 93%, 94%, 95%, 96%, 97%, 98%, 99% or 100% identical to nucleotides 136 to 145 of SEQ ID NO: 3;

(P15) An oligonucleotide of at least 6, 10, 15, 20, 25, 30, 35, 40, 45, or 50 nucleotides comprising or consisting of a complementary nucleotide sequence to a sequence at least about 75%, 80%, 85%, 86%, 87%, 88%, 89%, 90%, 91%, 92%, 93%, 94%, 95%, 96%, 97%, 98%, 99% or 100% identical to nucleotides 259 to 264 of SEQ ID NO: 1;

(P16) An oligonucleotide of at least 5, 10, 15, 20, 25, 30, 35, 40, 45, or 50 nucleotides comprising or consisting of a complementary nucleotide sequence to a sequence at least about 75%, 80%, 85%, 86%, 87%, 88%, 89%, 90%, 91%, 92%, 93%, 94%, 95%, 96%, 97%, 98%, 99% or 100% identical to nucleotides 258 to 262 of SEQ ID NO: 1:

(P17) An oligonucletide of at least 16, 20, 25, 30, 35, 40, 45, or 50 nucleotides comprising or consisting of a sequence at least about 75%, 80%, 85%, 86%, 87%, 88%, 89%, 90%, 91%, 92%, 93%, 94%, 95%, 96%, 97%, 98%, 99% or 100% identical to nucleotides 249 to 264 of SEQ ID NO: 1; and (P18) An oligonucleotide of at least 8, 10, 15, 20, 25, 30, 35, 40, 45, or 50 nucleotides comprising or consisting of a sequence at least about 75%, 80%, 85%, 86%, 87%, 88%, 89%, 90%, 91%, 92%, 93%, 94%, 95%, 96%, 97%, 98%, 99% or 100% identical to nucleotides 257 to 264 of SEQ ID NO: 1.

The probes may be fluorescence-labeled probes. The probes are, for example, probes capable of detecting a genetic mutation in EGFR.

For example, the oligonucleotides P1, P3, and P15 to P18 may be the oligonucleotides described below.

(P1) An oligonucleotide comprising or consisting of a sequence at least about 75%, 80%, 85%, 86%, 87%, 88%, 89%, 90%, 91%, 92%, 93%, 94%, 95%, 96%, 97%, 9, 98%, 99% or 100% identical to a complementary nucleotide sequence to a nucleotide sequence of 11 to 50 nucleotides comprising or consisting of nucleotides 251 to 261 of SEQ ID NO: 1, and in which the nucleotide corresponding to nucleotide 261 is adenine or cytosine, the nucleotide corresponding to nucleotide 251 is cytosine, and the cytosine is fluorescence-labeled.

(P3) An oligonucleotide comprising or consisting of a sequence at least about 75%, 80%, 85%, 86%, 87%, 88%, 89%, 90%, 91%, 92%, 93%, 94%, 95%, 96%, 97%, 98%, 99% or 100% identical to a complementary nucleotide sequence to a nucleotide sequence of 5 to 50 nucleotides comprising or consisting of nucleotides 257 to 261 of SEQ ID NO: 1, and in which the nucleotide corresponding to nucleotide 261 is adenine or cytosine, the nucleotide corresponding to nucleotide 257 is cytosine, and the cytosine is fluorescence-labeled.

(P15) An oligonucleotide comprising or consisting of a sequence at least about 75%, 80%, 85%, 86%, 87%, 88%, 89%, 90%, 91%, 92%, 93%, 94%, 95%, 96%, 97%, 98%, 99% or 100% identical to a complementary nucleotide sequence to a nucleotide sequence of 6 to 50 nucleotides comprising or consisting of nucleotides 259 to 264 of SEQ ID NO: 1, and in which the nucleotide corresponding to nucleotide 261 is adenine or cytosine, and cytosine positioned at the 3' side relative to the nucleotide is fluorescence-labeled.

(P16) An oligonucleotide comprising or consisting of a sequence at least about 75%, 80%, 85%, 86%, 87%, 88%, 89%, 90%, 91%, 92%, 93%, 94%, 95%, 96%, 97%, 98%, 99% or 100% identical to a complementary nucleotide sequence to a nucleotide sequence of 5 to 50 nucleotides comprising or consisting of nucleotides 258 to 262 of SEQ ID NO: 1, and in which the nucleotide corresponding to nucleotide 261 is adenine or cytosine, and cytosine positioned at the 5' side relative to the nucleotide is fluorescence-labeled.

(P17) An oligonucleotide comprising or consisting of a sequence that is at least about 75%, 80%, 85%, 86%, 87%, 88%, 89%, 90%, 91%, 92%, 93%, 94%, 95%, 96%, 97%, 98%, 99% or 100% identical to a nucleotide sequence of 16 to 50 nucleotides comprising or consisting of 249 to 264 nucleotides of SEQ ID NO: 1, and in which the nucleotide corresponding to nucleotide 261 is thymine or guanine, and cytosine positioned at the 5' side relative to the nucleotide is fluorescence-labeled.

(P18) An oligonucleotide comprising or consisting of a sequence that is at least about 75%, 80%, 85%, 86%, 87%, 88%, 89%, 90%, 91%, 92%, 93%, 94%, 95%, 96%, 97%, 98%, 99% or 100% identical to a nucleotide sequence of 8 to 50 nucleotides comprising or consisting of nucleotides 257 to 264 of SEQ ID NO: 1, and in which the nucleotide corresponding to nucleotide 261 is thymine or guanine, and cytosine positioned at the 3' side relative to the nucleotide is fluorescence-labeled.

Probes configured from oligonucleotides according to P1, P3, and P15-P18 are probes for detection of the EGFR 858 polymorphism (t/g), in other words, the EGFR 858 probe. These probes are probes for detection of the presence or absence of a substitution mutation in the nucleotide at position 261 in the nucleotide sequence of SEQ ID NO: 1.

Each of the oligonucleotides according to P1, P3, and P15-P18, for example, is complementary to the sense strand of the EGFR gene, and the polymorphism can be confirmed by hybridization with the sense strand. In the oligonucleotide according to P1, the nucleotide that is complementary (corresponding) to the nucleotide (t or g) at position 261 of SEQ ID NO: 1 is adenine (a) or cytosine (c). In the oligonucleotide according to P1, the oligonucleotide having the nucleotide that is complementary (corresponding) to the nucleotide (t or g) at position 261 of SEQ ID NO: 1 is adenine (a) is also referred to as "P1-wt" and the oligonucleotide having the nucleotide that is complementary (corresponding) to the nucleotide (t or g) at position 261 of SEQ ID NO: 1 is cytosine (c) is also referred to as "P1-mt." Since the P1-wt strongly hybridizes with the EGFR 858 wild-type detection sequence as compared to the EGFR 858 mutant-type detection sequence, it may be termed an EGFR 858 wild-type probe. Since the P1-mt strongly hybridizes with the EGFR 858 mutant-type detection sequence as compared to the EGFR 858 wild-type detection sequence, it may be termed an EGFR 858 mutant-type probe. The polymorphism in an EGFR gene can be detected depending on whether these oligonucleotides strongly hybridize with the EGFR 858 wild-type detection sequence or with the EGFR 858 mutant-type detection sequence out of the detection sequences for EGFR gene.

The oligonucleotide according to P3 for example is complementary to the sense strand of the EGFR gene, and the polymorphism can be confirmed by hybridization with the sense strand. In the oligonucleotide according to P3, the nucleotide that is complementary (corresponding) to the nucleotide (t or g) position 261 of SEQ ID NO: 1 is adenine (a) or cytosine (c). In the oligonucleotide according to P3, the oligonucleotide having the nucleotide that is complementary (corresponding) to the nucleotide (t or g) at position 261 of SEQ ID NO: 1 is adenine (a) is also referred to as "P3-wt" and the oligonucleotide having the nucleotide that is complementary (corresponding) to the nucleotide (t or g) at position 261 of SEQ ID NO: 1 is cytosine (c) is also referred to as "P3-mt" Since the P3-wt strongly hybridizes with the EGFR 858 wild-type detection sequence as compared to the EGFR 858 mutant-type detection sequence, it may be termed an EGFR 858 wild-type probe. Since the P3-mt strongly hybridizes with the EGFR 858 mutant-type detection sequence as compared to the EGFR 858 wild-type detection sequence, it may be termed an EGFR 858 mutant-type probe. The polymorphism in an EGFR gene can be detected depending on whether these oligonucleotides strongly hybridize with the EGFR 858 wild-type detection sequence or with the EGFR 858 mutant-type detection sequence out of the detection sequences for EGFR gene.

As described above, the oligonucleotide according to P1 (3T-EGFR-858-R2) has a nucleotide length of 11 to 50 nucleotides, a nucleotide length of 11 to 40 nucleotides, a nucleotide length of 11 to 30 nucleotides, or a nucleotide length of 12 to 20 nucleotides. The oligonucleotide according to P3 (3T-EGFR-858-R1) has a nucleotide length of 5 to 50 nucleotides as described above, a nucleotide length of 10 to 40 nucleotides, and a nucleotide length of 10 to 30 nucleotide-nucleotides, or a nucleotide length of 12 to 20 nucleotides.

In each of the oligonucleotides, there is no particular limitation on the site that is labeled by a labeling substance, including for example, the 5' terminal domain, the 3' terminal domain, the 5' terminal, and the 3' terminal. Furthermore, as described below, the nucleotide that is labeled by a labeling substance in the above oligonucleotides includes, for example, cytosine (c) or guanine (g). The labeling substance for example may be directly labeled on the nucleotide, or the nucleotide may be indirectly labeled by labeling of a site at any of the nucleotide residues including the nucleotide.

The oligonucleotide P1 according to some embodiment may include the fluorescence-labeled nucleotide that is complementary (corresponding) to the nucleotide at position 251 at the $1^{st}$ to $3^{rd}$ position counted from the 3' terminal. The "nucleotide that is complementary (corresponding) to the nucleotide at position 251" in the oligonucleotide means a nucleotide (c) that is complementary to the nucleotide (g) at position 251 in the nucleotide sequence of SEQ ID NO: 1 when the oligonucleotide is aligned with the nucleotide sequence of SEQ ID NO: 1. More specifically, the nucleotide that is complementary to nucleotide 251 is expressed by c in the oligonucleotide according to P1.

The oligonucleotide according to P1 may include the fluorescence-labeled nucleotide that is complementary to the nucleotide at position 251 at the 3' terminal.

The P1-mt is for example the oligonucleotide of SEQ ID NO: 7, and the P1-wt is for example the oligonucleotide of SEQ ID NO: 8.

```
                                              (SEQ ID NO: 7)
                      5'-ttggcccgcccaaaatc-3'
                      (3T-EGFR-858-R2)

(SEQ ID NO: 8)
                      5'-ttggccagcccaaaatc-3'
```

The oligonucleotide P3 according to some embodiment may include the fluorescence-labeled nucleotide that is complementary (corresponding) to the nucleotide at position 257 at the $1^{st}$ to $3^{rd}$ position counted from the 3' terminal. The "nucleotide that is complementary (corresponding) to the nucleotide at position 257" in the oligonucleotide means a nucleotide (c) that is complementary to the nucleotide (g) at position 257 in the nucleotide sequence of SEQ ID NO: 1 when the oligonucleotide is aligned with the nucleotide sequence of SEQ ID NO: 1. More specifically, the nucleotide that is complementary to nucleotide 257 is expressed by c in the oligonucleotide according to P3.

The P3-wt is for example the oligonucleotide of SEQ ID NOs: 12-14, and the P3-mt is for example the oligonucleotide of SEQ ID NOs: 9-11.

```
                                              (SEQ ID NO: 12)
                         5'-cagtttggccagccc-3'

(SEQ ID NO: 13)
                         5'-ctgtttggccagccc-3'

(SEQ ID NO: 14)
                         5'-ccgtttggccagccc-3'
```

```
5'-cagtttggcccgccc-3'                    (SEQ ID NO: 9)
(3T-EGFR-858-R1)

5'-ctgtttggcccgccc-3'                    (SEQ ID NO: 10)

5'-ccgtttggcccgccc-3'                    (SEQ ID NO: 11)
```

The oligonucleotide according to P15 includes, for example, the oligonucleotides according to P15-1-P15-5.

(P15-1) An oligonucleotide including a sequence at least about 75%, 80%, 85%, 86%, 87%, 88%, 89%, 90%, 91%, 92%, 93%, 94%, 95%, 96%, 97%, 98%, 99% or 100% identical to a complementary nucleotide sequence of 30 to 50 nucleotides to nucleotides 235 to 264 of SEQ ID NO: 1; and in which the nucleotide corresponding to nucleotide 261 is adenine or cytosine, the nucleotide corresponding to nucleotide 235 is cytosine, and the cytosine is fluorescence-labeled.

(P15-2) An oligonucleotide including a sequence at least about 75%, 80%, 85%, 86%, 87%, 88%, 89%, 90%, 91%, 92%, 93%, 94%, 95%, 96%, 97%, 98%, 99% or 100% identical to a complementary nucleotide sequence of 26 to 50 nucleotides to nucleotides 239 to 264 of SEQ ID NO: 1; and in which the nucleotide corresponding to nucleotide 261 is adenine or cytosine, the nucleotide corresponding to nucleotide 239 is cytosine, and the cytosine is fluorescence-labeled.

(P15-3) An oligonucleotide including a sequence at least about 75%, 80%, 85%, 86%, 87%, 88%, 89%, 90%, 91%, 92%, 93%, 94%, 95%, 96%, 97%, 98%, 99% or 100% identical to a complementary nucleotide sequence of 21 to 50 nucleotides to nucleotides 244 to 264 of SEQ ID NO: 1; and in which the nucleotide corresponding to nucleotide 261 is adenine or cytosine, the nucleotide corresponding to nucleotide 244 is cytosine, and the cytosine is fluorescence-labeled.

(P15-4) An oligonucleotide including a sequence at least about 75%, 80%, 85%, 86%, 87%, 88%, 89%, 90%, 91%, 92%, 93%, 94%, 95%, 96%, 97%, 98%, 99% or 100% identical to a complementary nucleotide sequence of 7 to 50 nucleotides to nucleotides 258 to 264 of SEQ ID NO: 1; and in which the nucleotide corresponding to nucleotide 261 is adenine or cytosine, the nucleotide corresponding to nucleotide 258 is cytosine, and the cytosine is fluorescence-labeled.

(P15-5) An oligonucleotide including a sequence at least about 75%, 80%, 85%, 86%, 87%, 88%, 89%, 9, 1%, 92%, 93%, 94%, 95%, 96%, 97%, 98%, 99% or 100% identical to a complementary nucleotide sequence of 6 to 50 nucleotides to nucleotides 259 to 264 of SEQ ID NO: 1; and in which the nucleotide corresponding to nucleotide 261 is adenine or cytosine, the nucleotide corresponding to nucleotide 259 is cytosine, and the cytosine is fluorescence-labeled.

The oligonucleotide according to P16 includes, for example, the oligonucleotides according to P16-1-P16-10.

(P16-1) An oligonucleotide including a sequence at least about 75%, 80%, 85%, 86%, 87%, 88%, 89%, 90%, 91%, 92%, 93%, 94%, 95%, 96%, 97%, 98%, 99% or 100% identical to a complementary nucleotide sequence of 6 to 50 nucleotides to nucleotides 258 to 263 of SEQ ID NO: 1, and in which the nucleotide corresponding to nucleotide 261 is adenine or cytosine, the nucleotide corresponding to nucleotide 263 is cytosine, and the cytosine is fluorescence-labeled.

(P16-2) An oligonucleotide including a sequence at least about 75%, 80%, 85%, 86%, 87%, 88%, 89%, 90%, 91%, 92%, 93%, 94%, 95%, 96%, 97%, 98%, 99% or 100% identical to a complementary nucleotide sequence of 5 to 50 nucleotides to nucleotides 258 to 262 of SEQ ID NO: 1, and in which the nucleotide corresponding to nucleotide 261 is adenine or cytosine, the nucleotide corresponding to nucleotide 262 is cytosine, and the cytosine is fluorescence-labeled.

(P16-3) An oligonucleotide including a sequence at least about 75%, 80%, 85%, 86%, 87%, 88%, 89%, 90%, 91%, 92%, 93%, 94%, 95%, 96%, 97%, 98%, 99% or 100%, identical to a complementary nucleotide sequence of 14 to 50 nucleotides to nucleotides 258 to 271 of SEQ ID NO: 1, and in which the nucleotide corresponding to nucleotide 261 is adenine or cytosine, the nucleotide corresponding to nucleotide 271 is cytosine, and the cytosine is fluorescence-labeled.

(P16-4) An oligonucleotide including a sequence at least about 75%, 80%, 85%, 86%, 87%, 88%, 89%, 90%, 91%, 92%, 93%, 94%, 95%, 96%, 97%, 98%, 99% or 100% identical to a complementary nucleotide sequence of 17 to 50 nucleotides to nucleotides 258 to 274 of SEQ ID NO: 1, and in which the nucleotide corresponding to nucleotide 261 is adenine or cytosine, the nucleotide corresponding to nucleotide 274 is cytosine, and the cytosine is fluorescence-labeled.

(P16-5) An oligonucleotide including a sequence at least about 75%, 80%, 85%, 86%, 87%, 88%, 89%, 90%, 91%, 92%, 93%, 94%, 95%, 96%, 97%, 98%, 99% or 100% identical to a complementary nucleotide sequence of 18 to 50 nucleotides to nucleotides 258 to 275 of SEQ ID NO: 1, and in which the nucleotide corresponding to nucleotide 261 is adenine or cytosine, the nucleotide corresponding to nucleotide 275 is cytosine, and the cytosine is fluorescence-labeled.

(P16-6) An oligonucleotide including a sequence at least about 75%, 80%, 85%, 86%, 87%, 88%, 89%, 90%, 91%, 92%, 93%, 94%, 95%, 96%, 97%, 98%, 99% or 100% identical to a complementary nucleotide sequence of 19 to 50 nucleotides to nucleotides 258 to 276 of SEQ ID NO: 1, and in which the nucleotide corresponding to nucleotide 261 is adenine or cytosine, the nucleotide corresponding to nucleotide 276 is cytosine, and the cytosine is fluorescence-labeled.

(P16-7) An oligonucleotide including a sequence at least about 75%, 80%, 85%, 86%, 87%, 88%, 89%, 90%, 91%, 92%, 93%, 94%, 95%, 96%, 97%, 98%, 99% or 100% identical to a complementary nucleotide sequence of 21 to 50 nucleotides to nucleotides 258 to 278 of SEQ ID NO: 1, and in which the nucleotide corresponding to nucleotide 261 is adenine or cytosine, the nucleotide corresponding to nucleotide 278 is cytosine, and the cytosine is fluorescence-labeled.

(P16-8) An oligonucleotide including a sequence at least about 75%, 80%, 85%, 86%, 87%, 88%, 89%, 90%, 91%, 92%, 93%, 94%, 95%, 96%, 97%, 98%, 99% or 100% identical to a complementary nucleotide sequence of 23 to 50 nucleotides to nucleotides 258 to 280 of SEQ ID NO: 1, and in which the nucleotide corresponding to nucleotide 261 is adenine or cytosine, the nucleotide corresponding to nucleotide 280 is cytosine, and the cytosine is fluorescence-labeled.

(P16-9) An oligonucleotide including a sequence at least about 75%, 80%, 85%, 86%, 87%, 88%, 89%, 90%, 91%, 92%, 93%, 94%, 95%, 96%, 97%, 98%, 99% or 100% identical to a complementary nucleotide sequence of 24 to 50 nucleotides to nucleotides 258 to 281 of SEQ ID NO: 1, and in which the nucleotide corresponding to nucleotide 261 is adenine or cytosine, the nucleotide corresponding to nucleotide 281 is cytosine, and the cytosine is fluorescence-labeled.

(P16-10) An oligonucleotide including a sequence at least about 75%, 80%, 85%, 86%, 87%, 88%, 89%, 90%, 91%, 92%, 93%, 94%, 95%, 96%, 97%, 9, 98%, 99% or 100% identical to a complementary nucleotide sequence of 27 to 50 nucleotides to nucleotides 258 to 284 of SEQ ID NO: 1, and in which the nucleotide corresponding to nucleotide 261 is adenine or cytosine, the nucleotide corresponding to nucleotide 284 is cytosine, and the cytosine is fluorescence-labeled.

The oligonucleotide according to P17 includes, for example, the oligonucleotides according to P17-1-P17-4.

(P17-1) An oligonucleotide including a sequence that is at least about 75%, 80%, 85%, 86%, 87%, 88%, 89%, 90%, 91%, 92%, 93%, 94%, 95%, 96%, 97%, 98%, 99% or 100% identical to a nucleotide sequence of 29 to 50 nucleotide, including nucleotides 236 to 264 of SEQ ID NO: 1, and in which the nucleotide corresponding to nucleotide 261 is thymine or guanine, the nucleotide corresponding to nucleotide 236 is cytosine, and the cytosine is fluorescence-labeled.

(P17-2) An oligonucleotide including a sequence that is at least about 75%, 80%, 85%, 86%, 87%, 88%, 89%, 90%, 91%, 92%, 93%, 94%, 95%, 96%, 97%, 98%, 99% or 100% identical to a nucleotide sequence of 24 to 50 nucleotides including nucleotides 241 to 264 of SEQ ID NO: 1, and in which the nucleotide corresponding to nucleotide 261 is thymine or guanine, the nucleotide corresponding to nucleotide 241 is cytosine, and the cytosine is fluorescence-labeled.

(P17-3) An oligonucleotide including a sequence that is at least about 75%, 80%, 85%, 86%, 87%, 88%, 89%, 90%, 91%, 92%, 93%, 94%, 95%, 96%, 97%, 98%, 99% or 100% identical to a nucleotide sequence of 18 to 50 nucleotides including nucleotides 247 to 264 of SEQ ID NO: 1, and in which the nucleotide corresponding to nucleotide 261 is thymine or guanine, the nucleotide corresponding to nucleotide 247 is cytosine, and the cytosine is fluorescence-labeled.

(P17-4) An oligonucleotide including a sequence that is at least about 75%, 80%, 85%, 86%, 87%, 88%, 89%, 90%, 91%, 92%, 93%, 94%, 95%, 96%, 97%, 98%, 99% or 100% identical to a nucleotide sequence of 16 to 50 nucleotides including nucleotides 249 to 264 of SEQ ID NO: 1, and in which the nucleotide corresponding to nucleotide 261 is thymine or guanine, the nucleotide corresponding to nucleotide 249 is cytosine, and the cytosine is fluorescence-labeled.

The oligonucletide according to P18 includes, for example, the oligonucleotides according to P18-1-P18-5.

(P18-1) An oligonucleotide including a sequence that is at least about 75%, 80%, 85%, 86%, 87%, 88%, 89%, 90%, 91%, 92%, 93%, 94%, 95%, 96%, 97%, 98%, 99% or 100% identical to a nucleotide sequence of 8 to 50 nucleotides including nucleotides 257 to 264 of SEQ ID NO: 1, and in which the nucleotide corresponding to nucleotide 261 is thymine or guanine, the nucleotide corresponding to nucleotide 264 is cytosine, and the cytosine is fluorescence-labeled.

(P18-2) An oligonucleotide including a sequence that is at least about 75%, 80%, 85%, 86%, 87%, 88%, 89%, 90%, 91%, 92%, 93%, 94%, 95%, 96%, 97%, 98%, 99% or 100% identical to a nucleotide sequence of 9 to 50 nucleotides including nucleotides 257 to 265 of SEQ ID NO: 1, and in which the nucleotide corresponding nucleotide 261 is thymine or guanine, the nucleotide corresponding to nucleotide 265 is cytosine, and the cytosine is fluorescence-labeled.

(P18-3) An oligonucleotide including a sequence that is at least about 75%, 80%, 85%, 86%, 87%, 88%, 89%, 90%, 91%, 92%, 93%, 94%, 95%, 96%, 97%, 98%, 99% or 100% identical to a nucleotide sequence of 13 to 50 nucleotides including nucleotides 257 to 269 of SEQ ID NO: 1, and in which the nucleotide corresponding to nucleotide 261 is thymine or guanine, the nucleotide corresponding to nucleotide 269 is cytosine, and the cytosine is fluorescence-labeled.

(P18-4) An oligonucleotide including a sequence that is at least about 75%, 80%, 85%, 86%, 87%, 88%, 89%, 90%, 91%, 92%, 93%, 94%, 95%, 96%, 97%, 98%, 99% or 100% identical to a nucleotide sequence of 16 to 50 nucleotides including nucleotides 257 to 272 of SEQ ID NO: 1, and in which the nucleotide corresponding to nucleotide 261 is thymine or guanine, the nucleotide corresponding to nucleotide 272 is cytosine, and the cytosine is fluorescence-labeled.

(P18-5) An oligonucleotide including a sequence that is at least about 75%, 80%, 85%, 86%, 87%, 88%, 89%, 90%, 91%, 92%, 93%, 94%, 95%, 96%, 97%, 98%, 99% or 100% identical to a nucleotide sequence of 23 to 50 nucleotides including nucleotides 257 to 279 of SEQ ID NO: 1, and in which the nucleotide corresponding to nucleotide 261 is thymine or guanine, the nucleotide corresponding to nucleotide 279 is cytosine, and the cytosine is fluorescence-labeled.

The EGFR 858 probe of the present invention may be a probe in which the nucleotides at the both ends are cytosine and each cytosine is labeled. An example of such a probe includes the labeled oligonucleotide P19 below.

(P19) An oligonucleotide including a sequence at least about 75%, 80%, 85%, 86%, 87%, 88%, 89%, 90%, 91%, 92%, 93%, 94%, 95%, 96%, 97%, 98%, 99% or 100% identical to a complementary nucleotide sequence of 18 to 50 nucleotides to nucleotides 257 to 274 of SEQ ID NO: 1.

The probe may be a fluorescence-labeled probe. The probe is, for example, a probe capable of detecting a genetic mutation in EGFR.

For example, the oligonucleotide according to P19 may be the oligonucleotide described below.

(P19) An oligonucleotide including a sequence at least about 75%, 80%, 85%, 86%, 87%, 88%, 89%, 90%, 91%, 92%, 93%, 94%, 95%, 96%, 97%, 98%, 99% or 100% identical to a complementary nucleotide sequence of 18 to 50 nucleotides to nucleotides 257 to 274 of SEQ ID NO: 1, and in which the nucleotide corresponding to nucleotide number 261 is adenine or cytosine, the nucleotide corresponding to nucleotide 257 and the nucleotide corresponding to nucleotide 274 are cytosine, and each cytosine is fluorescence-labeled.

For example, the description, in relation to the oligonucleotides according to P1 and P3 can be applied to the oligonucleotides according to P15 to P19 unless otherwise noted. For example the labeled site in each oligonucleotide may be a cytosine residue as described above. With respect to the oligonucleotides according to P15, P16, and P19, for example, the labeled site may be a cytosine residue corresponding to guanine in SEQ ID NO: 1. With respect to the oligonucleotides according to P17 and P18, for example, the labeled site may be a cytosine residue in SEQ ID NO: 1.

The lower limit of the nucleotide length of the oligonucleotide according to P15 may be as short as 6 nucleotides or as long as 16 nucleotides.

The lower limit of the nucleotide length of the oligonucleotide according to P16 may be as short as 5 nucleotides or 6 nucleotides, or as long as 18 nucleotides.

The lower limit of the nucleotide length of the oligonucleotide according to P17 may be as short as 16 nucleotides or as long as 20 nucleotides.

The lower limit of the nucleotide length of the oligonucleotide according to P18 may be as short as 8 nucleotides or as long as 20 nucleotides.

The upper limit of the nucleotide length of each of the oligonucleotides according to P15 to P19 may be as long as 50 nucleotides or 40 nucleotides, or as short as 30 nucleotides.

With respect to the oligonucleotides according to P15 to P19, the specific examples of the sequences thereof will be described below. In each of the sequences below, the nucleotide corresponding to the target polymorphism site can be either a wild-type or a mutant-type, for example. Specifically, for example, in the oligonucleotides according to P15, P16, and P19, such nucleotides can be expressed by m (a or c), and in the oligonucleotides according to P17 and P18, such nucleotides can be expressed by k (t or g). However, the present invention is not limited to the sequences below.

```
P15-1
                                     (SEQ ID NO: 72)
5'-gccCgcccaaaatctgtgatcttgacatgc-3'
(3T-EGFR-858-R4)

P15-2
                                     (SEQ ID NO: 73)
5'-gccCgcccaaaatctgtgatcttgac-3'
(3T-EGFR-858-R5)

P15-3
                                     (SEQ ID NO: 74)
5'-tggccCgcccaaaatctgtgatc-3'
(3T-EGFR-858-R6)

P15-4
                                     (SEQ ID NO: 75)
5'-agcagtttggccCgcc-3'
(3T-EGFR-858-R7)

P15-5
                                     (SEQ ID NO: 76)
5'-acccagcagtttggccCgc-3'
(3T-EGFR-858-R8)

P16-1
                                     (SEQ ID NO: 77)
5'-ccCgcccaaaatctgtga-3'
(3T-EGFR-858-R9)

P16-2
                                     (SEQ ID NO: 78)
5'-cCgcccaaaatctgtgat-3'
(3T-EGFR-858-R10)

P16-3
                                     (SEQ ID NO: 79)
5'-cagtttggccCgcccaaaatct-3'
(3T-EGFR-858-R11)

P16-4
                                     (SEQ ID NO: 80)
5'-cagcagtttggccCgcccaaaa-3'
(3T-EGFR-858-R12)

P16-5
                                     (SEQ ID NO: 81)
5'-ccagcagtttggccCgcccaaaa-3'
(3T-EGFR-858-R13)

P16-6
                                     (SEQ ID NO: 82)
5'-cccagcagtttggccCgcccaaaa-3'
(3T-EGFR-85-R14)

P16-7
                                     (SEQ ID NO: 83)
5'-cacccagcagtttggccCgcccaa-3'
(3T-EGFR-858-R15)

P16-8
                                     (SEQ ID NO: 84)
5'-cgcacccagcagtttggccCgccc-3'
(3T-EGFR-858-R16)

P16-9
                                     (SEQ ID NO: 85)
5'-ccgcacccagcagtttggccCgcc-3'
(3T-EGFR-858-R17)

P16-10
                                     (SEQ ID NO: 86)
5'-cttccgcacccagcagtttggccCgcc-3'
(3T-EGFR-858-R18)

P17-1
                                     (SEQ ID NO: 89)
5'-catgtcaagatcacagattttgggcGggc-3'
(5T-EGFR-858-F1)

P17-2
                                     (SEQ ID NO: 90)
5'-caagatcacagattttgggcGggc-3'
(5T-EGFR-858-F2)

P17-3
                                     (SEQ ID NO: 91)
5'-cacagattttgggcGggccaaa-3'
(5T-EGFR-858-F3)

P17-4
                                     (SEQ ID NO: 92)
5'-cagattttgggcGggccaaa-3'
(5T-EGFR-858-F4)

P18-1
                                     (SEQ ID NO: 94)
5'-atcacagattttgggcGggc-3'
(3T-EGFR-858-F6)

P18-2
                                     (SEQ ID NO: 95)
5'-atcacagattttgggcGggcc-3'
(3T-EGFR-858-F7)

P18-3
                                     (SEQ ID NO: 96)
5'-attttgggcGggccaaac-3'
(3T-EGFR-858-F8)

P18-4
                                     (SEQ ID NO: 97)
5'-attttgggcGggccaaacTgc-3'
(3T-EGFR-858-E9)

P18-5
                                     (SEQ ID NO: 98)
5'-ggcGggccaaacTgctgggtgc-3'
(3T-EGFR-858-F10)

P19-1
                                     (SEQ ID NO: 88)
5'-cagcagtttggccCgccc-3'
(35T-EGFR-858-R21)
```

(2) Exon 19 Probe

The exon 19 probe according to the present invention as described above is a probe capable of detecting a genetic mutation in EGFR exon 19 deletion and comprises at least one of the following P5-P7 labeled oligonucleotides (P5) An oligonucleotide including a sequence that is at least about 75%, 80%, 85%, 86%, 87%, 88%, 89%, 90%, 91%, 92%, 93%, 94%, 95%, 96%, 97%, 98%, 99% or 100% identical to a nucleotide sequence of 9 to 50 nucleotides comprising nucleotides 104 to 112 of SEQ ID NO: 2.

(P6) An oligonucleotide including a sequence that is at least about 75%, 80%, 85%, 86%, 87%, 88%, 89%, 90%, 91%, 92%, 93%, 94%, 95%, 96%, 97%, 98%, 99% or 100% identical to a nucleotide sequence of 16 to 50 nucleotides comprising nucleotides 104 to 119 of SEQ ID NO: 2.

(P7) An oligonucleotide including a sequence that is at least about 75%, 80%, 85%, 86%, 87%, 88%, 89%, 90%, 91%, 92%, 93%, 94%, 95%, 96%, 97%, 98%, 99% or 100% identical to a nucleotide sequence of 10 to 50 nucleotides comprising nucleotides 136 to 145 of SEQ ID NO: 3.

The probes may be fluorescence-labeled probes. The probes are, for example, probes capable of detecting a genetic mutation in EGFR.

For example, the oligonucleotides according to P5 to P7 may be the oligonucleotides described below.

(P5) An oligonucleotide including a sequence that is at least about 75%, 80%, 85%, 86%, 87%, 88%, 89%, 90%, 91%, 92%, 93%, 94%, 95%, 96%, 97%, 98%, 99% or 100% identical to a nucleotide sequence of 9 to 50 nucleotides comprising nucleotides 104 to 112 of SEQ ID NO: 2, and in which the nucleotide corresponding to nucleotide 112 is thymine, the nucleotide corresponding to nucleotide 104 is cytosine, and the cytosine is fluorescence-labeled;

(P6) An oligonucleotide including a sequence that is at least about 75%, 80%, 85%, 86%, 87%, 88%, 89%, 90%, 91%, 92%, 93%, 94%, 95%, 96%, 97%, 98%, 99% or 100% identical to a nucleotide sequence of 16 to 50 nucleotides comprising nucleotides 104 to 119 of SEQ ID NO: 2, and in which the nucleotide at position 119 is substituted by a nucleotide other than G, and in which the nucleotide corresponding to nucleotide 104 is cytosine, and the cytosine is fluorescence-labeled; and (P7) An oligonucleotide including a sequence that is at least about 75%, 80%, 85%, 86%, 87%, 88%, 89%, 90%, 91%, 92%, 93%, 94%, 95%, 96%, 97%, 98%, 99% or 100% identical to a nucleotide sequence of 10 to 50 nucleotides comprising nucleotides 136 to 145 of SEQ ID NO: 3, and in which the nucleotide corresponding to nucleotide 145 is cytosine, and the cytosine is fluorescence-labeled.

The probe configured from the oligonucleotides in P5 to P7 above is a probe for detection of an exon 19 polymorphism, that is to say, the exon 19 probe.

The oligonucleotides P5 to P7 above for example are complementary to the antisense chain of the EGFR gene, and enables confirmation of the polymorphism by hybridization with the antisense chain.

For example, when the nucleotides at positions 104 to 112 of SEQ ID NO: 2 are wild-type variants, the oligonucleotide P5 strongly hybridizes with the detection sequence as compared to the case where the nucleotides at positions 104 to 112 of SEQ ID NO: 2 are the mutant-type variant resulting from a deletion mutation. Therefore, it is possible to detect whether there is an exon 19 polymorphism, that is to say, an exon 19 wild-type variant (polymorphism 1 in Table 1) in the EGFR gene, or whether there is an exon 19 mutant-type variant (polymorphisms 2-17 in Table 1) depending on whether the oligonucleotide P5 strongly hybridizes with the wild-type detection sequence or the mutant-type detection sequence out of the detection sequences for EGFR gene. Hereafter, a probe comprising the oligonucleotide P5 is termed an exon 19 wild-type probe.

For example, the oligonucleotide P6 strongly hybridizes with the detection sequence with the exception of the nucleotide at position 119 when the nucleotides at positions 104 to 119 of SEQ ID NO: 2 are the wild-type variant. Therefore, it is possible to detect whether there is an exon 19 polymorphism, that is to say, an exon 19 wild-type variant (polymorphism 1 in Table 1) in the EGFR gene, or whether there is an exon 19 mutant-type variant (polymorphisms 2-15 and 17 in Table 1) by whether or not the oligonucleotide P6 strongly hybridizes with the detection sequence of the EGFR gene. Hereafter, a probe comprising the oligonucleotide P6 is termed an exon 19 mutant-type (sub) probe.

For example, the oligonucleotide P7 strongly hybridizes with the detection sequence when the nucleotides at positions 137 to 151 of SEQ ID NO: 2 are mutant-type variants resulting from a deletion mutation as compared to the case where the nucleotides at positions 137 to 151 of SEQ ID NO: 2 are the wild-type variants having no deletion mutation. Therefore, it is possible to detect whether there is an exon 19 polymorphism, that is to say, an exon 19 wild-type variant (polymorphism 18 in Table 1) in the EGFR gene, or whether there is an exon 19 mutant-type variant (polymorphism 18 in Table 1) depending on whether the oligonucleotide P7 strongly hybridizes with the wild-type sequence or the mutant-type sequence out of the detection sequences for EGFR gene. Hereafter, a probe comprising the oligonucleotide P7 is termed an exon 19 mutant-type (del) probe.

As described above, the oligonucleotide according to P5 (5FL-EGFR-EX19-F2) has a nucleotide length of 9 to 50 nucleotides, a nucleotide length of 20 to 40 nucleotides, a nucleotide length of 25 to 35 nucleotides, or a nucleotide length of 10 to 30 nucleotides. The oligonucleotide according to P6 (5T-EGFR-EX19-No19-F2-3) has a nucleotide length of 9 to 50 nucleotides as described above, a nucleotide length of 20 to 40 nucleotides, a nucleotide length of 25 to 35 nucleotides, or a nucleotide length of 10 to 30 nucleotides. The oligonucleotide according to P7 (3T-EGFR-EX19-No18-F1) has a nucleotide length of 10 to 50 nucleotides as described above, a nucleotide length of 10 to 30 nucleotides, a nucleotide length of 12 to 30 nucleotides, or a nucleotide length of 15 to 20 nucleotides.

In each of the oligonucleotides, there is no particular limitation on the site that is labeled by a labeling substance, and, in some embodiments, it is the 5' terminal domain or the 3' terminal domain, and, in further embodiments, the 5' terminal or the 3' terminal. Furthermore, as described below, the nucleotide that is labeled by a labeling substance in the above oligonucleotides according to some embodiments is cytosine (c) or guanine (g). The labeling substance for example may be directly labeled on the nucleotide, or the nucleotide may be indirectly labeled by labeling of a site at any of the nucleotide residues including the nucleotide.

The oligonucleotide P5 according to some embodiments may include the fluorescence-labeled nucleotide corresponding to the nucleotide at position 104 at the $1^{st}$ to $3^{rd}$ position counted from the 5' terminal. The oligonucleotide P6 according to some embodiments may include the fluorescence-labeled nucleotide corresponding to the nucleotide at position 104 at the $1^{st}$ to $3^{rd}$ position counted from the 5' terminal. The "nucleotide corresponding to the nucleotide at position X," "nucleotide that is homologous to the nucleotide at position X," or "nucleotide corresponding to nucleotide X" in the oligonucleotide means a nucleotide (c) that is homologous to the nucleotide (c) at position X in the relevant nucleotide sequence. For example, the "nucleotide corresponding to the nucleotide at position 104," "nucleotide that is homologous to the nucleotide at position 104," or "nucleotide corresponding to nucleotide 104" in the nucleotide sequence of SEQ ID NO: 2 means a nucleotide (c) that is homologous to the nucleotide (c) at position 104 in the nucleotide sequence of SEQ ID NO: 2. More specifically, the nucleotide that is homologous to nucleotide number 104 is expressed by c in the oligonucleotide according to P5 and P6. The oligonucleotide P7 according to some embodiments may include the fluorescence-labeled nucleotide that is homologous to the nucleotide at position 145 at the $1^{st}$ to $3^{rd}$ position counted from the 3' terminal. The "nucleotide corresponding to the nucleotide at position 145," "nucleotide that is homologous to the nucleotide at position 145," or "nucleotide corresponding to nucleotide 145," in the nucleotide sequence of SEQ ID NO: 3 means a nucleotide (c) that is homologous to the nucleotide (c) at position 145 in the nucleotide sequence of SEQ ID NO: 3. More specifically, the nucleotide that is homologous to nucleotide number 145 is expressed by c in the oligonucleotide according to P7.

The oligonucleotide P5 according to some embodiments may include the fluorescence-labeled nucleotide that is homologous to the nucleotide at position 104 at the 5' terminal. The oligonucleotide P6 according to some embodiments may include the fluorescence-labeled nucleotide that is homologous to the nucleotide at position 104 at the 5' terminal. The oligonucleotide P7 according to some embodiments may include the fluorescence-labeled nucleotide that is homologous to the nucleotide at position 145 at the 3' terminal.

The oligonucleotide according to P5 is for example the oligonucleotide of SEQ ID NO: 5.

```
                                           (SEQ ID NO: 5)
    5'-cccgtcgctatcaaggaattaagagaagc-3'
    (5FL-EGFR-EX19-F2)
```

The oligonucleotide according to P6 is for example the oligonucleotide of SEQ ID NO: 4.

```
                                           (SEQ ID NO: 4)
    5'-cccgtcgctatcaagtaattaagagaagcaaca-3'
    (5T-EGFR-EX19-No19-F2-3)
```

The oligonucleotide according to P7 is for example the oligonucleotide of SEQ ID NO: 6.

```
                                           (SEQ ID NO: 6)
    5'-agcaacaaaggaaatc-3'
    (3T-EGFR-EX19-No18-F1)
```

Hybridization between the probe described herein and the target sequence gives double-strand nucleotides. The double-strand nucleotides can be detected electrochemically or by fluorescence.

In the present invention, each of the oligonucleotides (P1), (P3), (P5)-(P7), and (P15)-(P19) may be, for example, an oligonucleotide that hybridizes to a strand complementary to each of the oligonucleotides under stringent conditions. The hybridization can be detected by, for example, various hybridization assays. For example, the methods and conditions described in Molecular Cloning: A Laboratory Manual, Third Edition (Sambrook & Russell, Cold Spring Harbor Laboratory Press, 2001) and the like can be employed as the hybridization assays and the stringent conditions.

In the present invention, as described above, the oligonucleotides according to P1, P3, P5-P7, and P15-P19 each may be an oligonucleotide including (comprising or consisting of) a sequence having a sequence about 75%, 80%, 85%, 86%, 87%, 88%, 89%, 90%, 91%, 92%, 93%, 94%, 95%, 96%, 97%, 98%, 99% or 100% identical to any one of the sequences described above. The probe of the present invention may be a probe configured from the oligonucleotides described above or a probe containing the oligonucleotides described above.

The probe may be configured from either native nucleic acids or non-native nucleic acids, for example. Examples of the native nucleic acids include DNA and RNA. Examples of the non-native nucleic acids include peptide nucleic acid (PNA) and cross-linking nucleic acid such as Bridged Nucleic Acid (BNA, also referred to as Locked Nucleic Acid (LNA)). When the probe is configured from the non-native nucleic acids, for example, ability of hybridizing to the target sequence to be detected can be increased. Therefore, for example, the sequence of the probe can be designed shorter. The prediction of the Tm value of a double-stranded nucleic acid composed of a probe configured from the LNA and the target sequence to be detected can be calculated using the website of EXIQON (exiqon.com/oligo-tools).

Specifically, in some embodiments, the fluorescence-labeled oligonucleotide for example includes a substance that emits fluorescent light when not hybridized to the target sequence, and in which the fluorescent intensity increases or decreases when hybridized to the target sequence. Furthermore, the fluorescence-labeled oligonucleotide for example includes a substance that emits fluorescent light when not hybridized to the target sequence, and in which the fluorescent intensity decreases when hybridized to the target sequence.

There is no particular limitation on the fluorescent dye, and includes for example a fluorescent substance such as a fluorophore or the like. The fluorescent dye includes fluorescein, fluorophor, rhodamine, polymethine dye derivatives, and the like. Commercially available fluorescent dyes include PACIFIC BLUE (manufactured by Molecular Probes), BODIPY FL (manufactured by Molecular Probes), FluorePrime (manufactured by Amersham Pharmacia), Fluoredite (manufactured by Millipore), FAM (manufactured by ABI). Cy3 and Cy5 (manufactured by Amersham Pharmacia), TAMRA (manufactured by Molecular Probes), and the like. There is no particular limitation on the detection conditions for the fluorescent dye, and for example, suitable determination is enabled by the type of fluorescent dye that is used. Detection is enabled for example using PACIFIC BLUE at a detection wavelength of 450-480 nm. TAMRA at a detection wavelength of 585-700 nm, and BODIPY FL at a detection wavelength of 515-555 nm. Use of the fluorescence-labeled oligonucleotides as described above for example enables simple confirmation of the hybridization and dissociation in response to the fluctuation in the fluorescent intensity by detection of fluorescence as a signal and by measurement of the fluorescent intensity that is used as a signal value.

In light of detection efficiency, the probe for detection of a polymorphism according to some embodiments is a labeled probe having a label attached thereto. An actual example of the labeling substance in the labeled probe for example includes a fluorescent dye or a fluorophore. An actual example of the labeled probe includes, but is not limited to, a probe that is labeled with a fluorescent dye and in which the fluorescent light is emitted when in an independent configuration and which decreases (for example, undergoes quenching) as a result of the formation of a hybrid.

A probe using the above type of quenching phenomenon is generally termed a "quenching probe". Quenching probes according to some embodiments include a probe in which a nucleotide in the 3' domain of the oligonucleotide (for example, the 3' terminal) or the 5' domain of the oligonucleotide (for example, the 5' terminal) is labeled with a fluorescent dye, and the nucleotide to be labeled may be cytosine (C). In this case, in some embodiments of the present invention, a nucleotide sequence in the labeled probe may be designed so that a nucleotide that forms a pair with the terminal nucleotide C in the labeled probe or a nucleotide that is separated by 1 to 3 nucleotides from the nucleotide forming such a pair in the detection target sequence for hybridization with the labeled probe is a guanine (G). This type of probe is generally termed as "guanine quenching probe", and is known as a so-called "QPROBE". When this type of guanine quenching probe hybridizes with the detection target sequence, a phenomenon occurs in which the C on the terminal labeled by fluorescent dye approaches the G in the detection target sequence and therefore the emission of fluorescent light is weakened (fluorescent intensity is decreased). The use of this type of probe enables simple confirmation of hybridization and dissociation in response to the fluctuation in the signal. Furthermore the labeling substance can be typically bonded to the nucleotide of a phosphate group.

The probe according to the present invention may add a phosphate group to the 3' terminal. DNA (target DNA) that detected the presence or the absence of a mutation can be prepared by a gene amplification method such as PCR, and at that time, the probe according to the present invention may coexist in the reaction solution for the gene amplification reaction. In this case, when a phosphate group is added to the 3' terminal of the probe, the probe itself can sufficiently prevent the extension due to the gene amplification reaction. Furthermore the same effect is obtained by addition of the labeling substance as described above to the 3' terminal.

In addition to a method of detection using a QProbe, a known detection method may be applied. This type of detection method includes for example a Taq-man Probe method or an RFLP method.

There is no particular limitation on the fluorescent dye, and includes for example fluorescein, fluorophor, rhodamine, polymethine dye derivatives, and the like. Commercially available fluorescent dyes include BODIPY FL (manufactured by Molecular Probes), FluorePrime (manufactured by Amersham Pharmacia), Fluoredite (manufactured by Millipore). FAM (manufactured by ABI), Cy3 and Cy5 (manufactured by Amersham Pharmacia), TAMRA (manufactured by Molecular Probes), and the like. A combination of fluorescent dyes used in a plurality of probes for example may enable detection under different conditions, and without particular limitation thereon, the combination may include PACIFIC BLUE (detection wavelength of 450-480 nm), TAMRA (detection wavelength of 585-700 nm), and BODIPY FL (detection wavelength of 515-555 nm).

Method of Detection of Polymorphism

The method of detecting a polymorphism according to the present invention is a method of detecting a polymorphism in an EGFR gene, and is characterized by use of a probe that hybridizes with the detection sequence.

The method of detecting a polymorphism according to the present invention is characterized by use of the probe for detecting a polymorphism according to the present invention. The following description does not impose any limitation on other features of configuration or conditions or the like. In addition to the medical field, the present invention can be applied, for example, to polymorphism detection in an EGFR gene in the fields excluding diagnosis and treatment.

The method of detecting a polymorphism according to the present invention for example includes step (A) and step (B) below.

(A) A step of changing the temperature of the reaction system including the nucleic acid to be detected that detects the polymorphism and the probe for detecting a polymorphism, and measuring a signal value indicating the state of melting of the hybridization product formed by the nucleic acid to be detected and the probe for detecting a polymorphism according to the present invention.

(B) A step of determining the polymorphism in the nucleic acid to be detected from the fluctuation in the signal value associated with the temperature change.

In the step (A), the probe for detecting a polymorphism according to the present invention for example may be a single type or may combine use of two or more. The type of probe that is used for detecting a polymorphism for example enables suitable determination in response to the polymorphism of the detection target.

It is sufficient if the probe or probes for detecting a polymorphism used in step (A) includes at least one probe that is the probe for detecting a polymorphism according to the present invention. The type of probe for example enables suitable determination in response to the polymorphism of the detection target in the EGFR gene. In the present invention, for example, detection of only the EGFR 858 polymorphism may be executed, detection of only the exon 19 polymorphism may be executed, or detection of both polymorphisms in a single reaction system may be executed. Furthermore, it is possible to detect at least one of the EGFR 858 polymorphism and the exon 19 polymorphism, and another polymorphism in a single reaction system. There is no particular limitation on the other polymorphism, and for example, may include an EGFR 790 polymorphism in the EGFR gene.

When only detecting the EGFR 858 polymorphism, the EGFR 858 probe of the probe for detection of a polymorphism according to the present invention may be used. The EGFR 858 probe may be an EGFR 858 wild-type probe, an EGFR 858 mutant-type probe, or a combination of both.

When detecting only the exon 19 polymorphism, of the probes for detection of a polymorphism according to the present invention, at least one type of the exon 19 wild-type probe, the exon 19 mutant-type (sub) probe, and the exon 19 mutant-type (del) probe may be used. The use of the exon 19 wild-type probe enables detection of whether the exon 19 polymorphism is an exon 19 wild-type variant (polymorphism 1) or an exon 19 mutant-type variant (polymorphism 2 to polymorphism 17). The use of the exon 19 mutant-type (sub) probe enables detection of whether the polymorphism is an exon 19 wild-type variant (polymorphism 1) or an exon 19 mutant-type variant (polymorphism 2-15, and 17). The use of the exon 19 mutant-type (del) probe enables detection of whether the polymorphism is an exon 19 wild-type variant (polymorphism 1) or an exon 19 mutant-type variant (polymorphism 18). In the present invention, any of the exon 19 wild-type probe, the exon 19 mutant-type (sub) probe, and the exon 19 mutant-type (del) probe may be used. Since it is possible to determine whether the polymorphism is the polymorphism 1 or the polymorphism 2-18, two or more types may be used in combination. There is no particular limitation on the probe combination, in some embodiments, a combination of P5 and P7 enables detection of the 18 types of polymorphism 1-18 and the combination of P6 and P7 enables detection of 17 types with the exception of polymorphism 16 (although P5 is subjected to self quenching. P6 does not undergo self quenching), that P5 used in isolation enables detection of 17 types with the exception of polymorphism 18, P6 used in isolation enables detection of 16 types with the exception of polymorphism 16 and 18 (although P5 is subjected to self quenching, P6 does not undergo self quenching), and P7 used in isolation enables detection of only one type being polymorphism 18.

The present invention according to some embodiments may combine the EGFR 858 probe and the exon 19 probe. Since the probe according to the present invention as described above enables detection of a polymorphism with superior reliability. Therefore for example, the EGFR 858 polymorphism and the exon 19 polymorphism can be respectively detected specifically even when the EGFR 858 probe and an exon 19 probe are used in a single reaction solution. As described above, the exon 19 wild-type probe, the exon 19 mutant-type (sub) probe and the exon 19 mutant-type (del) probe may be used in combination as the exon 19 probes.

The present invention according to additional embodiments detects the EGFR 790 polymorphism or simultaneously detects the EGFR 858 polymorphism and/or the exon 19 polymorphism. "Simultaneously detects" for example includes the meaning of detection by use of the same single reaction system. In this case, the present invention in addition to both probes may combine use of the EGFR 790 probe.

There is no particular limitation on the EGFR 790 probe, and for example, it includes a probe comprising the oligonucleotide (P14) below.

(P14) An oligonucleotide including a sequence at least about 75%, 80%, 85%, 86%, 87%, 88%, 89%, 90%, 91%, 92%, 93%, 94%, 95%, 96%, 97%, 98%, 99% or 100% identical to a complementary nucleotide sequence of 14 to 50 nucleotides to nucleotides 334 to 347 of SEQ ID NO: 21, in which the nucleotide (g) at position 334 in the nucleotide sequence of SEQ ID NO: 21 is the 5' terminal.

The probe may be a fluorescence-labeled probe. The probe is, for example, a probe capable of detecting a genetic mutation in EGFR.

For example, the oligonucleotide according to P14 may be the oligonucleotide described below.

(P14) An oligonucleotide including a sequence at least about 75%, 80%, 85%, 86%, 87%, 88%, 89%, 90%, 91%, 92%, 93%, 94%, 95%, 96%, 97%, 98%, 99% or 100% identical to a complementary nucleotide sequence to an oligonucleotide of 14 to 50 nucleotides to nucleotides 334 to 347 of SEQ ID NO: 21, in which the nucleotide (g) at position 334 in the nucleotide sequence of SEQ ID NO: 21 is the 5' terminal, and in which the nucleotide corresponding to nucleotide 347 is guanine or adenine and the nucleotide corresponding to nucleotide 334 is cytosine.

The probe comprising the oligonucleotide according to (P14), for example, is a probe for detection of the presence or absence of a substitution mutation in the nucleotide at position 347 in the nucleotide sequence of SEQ ID NO: 21. The oligonucleotide according to (P14), for example, is complementary to the sense strand of the EGFR gene, and the polymorphism can be confirmed by hybridization with the sense strand. In the oligonucleotide according to (P14), the nucleotide that is complementary to the nucleotide at position 347 of SEQ ID NO: 21 is expressed by r. The denotation r refers to guanine (g) and adenine (a). Since an oligonucleotide in which r is guanine (g) strongly hybridizes with the EGFR 790 wild-type detection sequence as compared to the EGFR 790 mutant-type detection sequence, it may be termed an EGFR 790 wild-type probe. Since an oligonucleotide in which r is adenine (a) strongly hybridizes with the EGFR 790 mutant-type detection sequence as compared to the EGFR 790 wild-type detection sequence, it may be termed an EGFR 790 mutant-type probe. These oligonucleotides enable detection of the EGFR gene polymorphism depending on whether these oligonucleotides strongly hybridize with the EGFR 790 wild-type detection sequence or the EGFR 790 mutant-type detection sequence out of the detection sequences for EGFR gene. The 3' terminal of the oligonucleotide according to (P14) is cytosine.

The oligonucletide according to (P14) includes the oligonucleotide of SEQ ID NO: 22, and in that the nucleotide sequence, r, has the same denotation as that described above. Actual examples of the oligonucleotide include the oligonucleotide of SEQ ID NO: 23 that is an EGFR790 mutant-type probe and the oligonucleotide of SEQ ID NO: 24 that is an EGFR790 wild-type probe.

```
                                       (SEQ ID NO: 22)
           5'-tgagctgcrtgatgaggtgcac-3

(SEQ ID NO: 23)
           5'-tgagctgcatgatgaggtgcac-3'
           (3T-EGFR-T790M-mt-R3

(SEQ ID NO: 24)
           5'-tgagctgcgtgatgaggtgcac-3'
```

In the present invention, as described above, the oligonucleotide according to P14 may be an oligonucleotide including a sequence that is at least about 75%, 80%, 85%, 86%, 87%, 88%, 89%, 90%, 91%, 92%, 93%, 94%, 95%, 96%, 97%, 98%, 99% or 100% identical to any one of the sequences described above. In step (A), when the probe for detection of a polymorphism is a combination of two or more types, each probe for example may be a labeled probe that includes a different labeling substance. The different labeling substances may be labeling substances that include different detection conditions.

In the present invention, the nucleic acid to be detected includes single-stranded nucleic acid or double-stranded nucleic acid. When the nucleic acid to be detected is double stranded, for example, as described below, step (A) may include a step in which the reaction system is heated, and the double-stranded nucleic acid to be detected is dissociated. The dissociation of the double-stranded nucleic acid into a single-strand nucleic acid for example facilitates hybridization between the single-stranded nucleic acid and the probe for detection of a polymorphism according to the present invention.

In the present invention, the nucleic acid to be detected for example may be a nucleic acid originally contained in the test sample, or, since the detection accuracy can be improved, the nucleic acid to be detected may be an amplification product amplified by a nucleic acid amplification method using the nucleic acid as template nucleic acid. The amplification product may be an amplification product using DNA in the sample as a template. Furthermore, the nucleic acid to be detected may be cDNA that is synthesized from RNA such as the total RNA, mRNA or the like in the test sample using RT-PCR (reverse transcription PCR), or may be an amplification product using cDNA as a template. The amplification product for example may be an amplification product of a domain including the detection sequence. The detection sequence may include only the detection site of the EGFR858 polymorphism as the detection site or may include only the detection site of the exon 19 polymorphism as the detection site. Further, the detection sequence may include the EGFR858 polymorphism and the exon 19 polymorphism as the detection site. Furthermore, the detection sequence may further include the EGFR790 polymorphism as described above as the detection site.

When the nucleic acid to be detected is the amplification product above, the method of detection of a polymorphism according to the present invention for example may further include a step of producing the amplification product from template nucleic acid. The amplification product production step for example may be performed in advance of the step (A) above, or may be performed during the step (A).

When the nucleic acid to be detected is the amplification product above, an amplification product may be prepared in advance for use in the step (A) and a reaction system may be prepared that includes the probe for detection of a polymorphism according to the present invention and the amplification product, or the amplification product may be prepared from the template nucleic acid in the reaction system in the presence of the probe for detection of the polymorphism according to the present invention and a reaction system may be prepared that includes the probe for detection of a polymorphism and the amplification product.

There is no particular limitation on the method of amplifying the nucleic acid, and for example, the method includes a polymerase chain reaction (PCR) method, a nucleic acid sequence based amplification (NASBA) method, a transcription-mediated amplification (TMA) method, a strand displacement amplification (SDA) method, and of those methods, the PCR method may be used. There is no particular limitation on the conditions for the amplification method, and performance is possible using a known method.

A primer for amplifying the sequence including the target polymorphism to be detected in the EGFR gene in the production of the amplification product from the template nucleic acid may be used.

There is no particular limitation on the amplification domain of the primer, and suitable definition may be performed according to the target polymorphism to be detected. In other words, when the target polymorphism to be detected is the EGFR858 polymorphism, the amplification domain may be the domain including the detection site of the EGFR858 polymorphism, that is to say, the domain that includes the nucleotide at position 261 in the nucleotide sequence of SEQ ID NO: 1. More specifically, the amplification domain may be the domain that includes the sequence that hybridizes with at least one of the oligonucleotides according to P1, P3, and P15. P19 in the nucleotide sequence of SEQ ID NO: 1 of the EGFR gene. Furthermore, when the target polymorphism to be detected is the exon 19 polymorphism, the amplification domain may be the domain that includes the detection site for the exon 19 polymorphism, that is to say, the domain that includes the nucleotides at positions 112 to 151 in the nucleotide sequence of SEQ ID NO: 2. More specifically, the domain may include the sequence that hybridizes with at least one of the oligonucleotides according to P5 to P6 in the nucleotide sequence of SEQ ID NO: 2 and the oligonucleotide according to P7 in the nucleotide sequence of SEQ ID NO: 3. Furthermore, when the target polymorphism to be detected is the EGFR858 polymorphism and the exon 19 polymorphism, the amplification domain may be the two domains being the domain that includes the detection site for the exon 19 polymorphism and the domain that includes the detection site for the EGFR858 polymorphism. The amplification domain further may include the domain that includes the detection site for the EGFR790 polymorphism.

There is no particular limitation on the primer sequence, and for example, it is sufficient if it enables amplification of the detection sequence including the detection site, and may be suitably defined by a known method in response to the detection sequence and peripheral sequences thereto. There is no particular limitation on the primer length, and may be set to a generally-used length, and for example a nucleotide length of 10 to 50 nucleotides may be used.

The primer for example includes use of any one of a forward primer that amplifies the sense strand (hereinafter denoted as "F primer") and a reverse primer that amplifies the antisense strand (hereinafter denoted as "R primer"). However, both as a pair in the configuration of a primer set may be used. An example of the primer will be described in relation to the primer according to the present invention.

A primer configured to detect a genetic mutation in EGFR-exon21 L858R includes a primer that amplifies the region that includes the sequence that hybridizes with at least one of the oligonucleotides according to P1, P3, and P15-P19 in the nucleotide sequence of SEQ ID NO: 1 in the EGFR gene, and more specifically, is a primer selected from the group consisting of oligonucleotides P8 to P10.

(P8) An oligonucleotide of 10 to 50 nucleotides homologous to nucleotides 224 to 233 of SEQ ID NO: 1, and in which the 3' terminal is the nucleotide C at position 233.

(P9) An oligonucleotide of 10 to 50 nucleotides complementary to nucleotides 284 to 293 of SEQ ID NO: 1, and in which the 3' terminal is the nucleotide C complementary to the nucleotide G at position 284.

(P10) An oligonucleotide of 10 to 50 nucleotides complementary to nucleotides 290 to 299 of SEQ ID NO: 1, and in which the 3' terminal is the nucleotide C complementary to the nucleotide G at position 290.

The oligonucleotide according to P8 for example includes the oligonucleotide of SEQ ID NO: 15, the oligonucleotide of P9 for example includes the oligonucleotide of SEQ ID NO: 17, and the oligonucleotide of P10 for example includes the oligonucleotide of SEQ ID NO: 16.

```
                                       (SEQ ID NO: 15)
     3'-aggaacgtactggtgaaaacaccgc-3'
     (EGFR-L858R-F2)

(SEQ ID NO: 16)
     5'-ttactttgcctccttctgcatggtattc-3'
     (EGFR-L858R-R2)

(SEQ ID NO: 17)
     5'-gcctccttctgcatggtattctttctc-3'
     (EGFR-L858R-R1)
```

A primer configured to detect a genetic mutation in EGFR-exon19 deletion includes a primer that amplifies the region that includes the sequence that hybridizes with at least one of the oligonucleotides according to P5 and P6 in the nucleotide sequence of SEQ ID NO: 2 in the EGFR gene, or the region that includes the sequence that hybridizes with the oligonucleotide according to P7 in the nucleotide sequence of SEQ ID NO: 3 and more specifically, is a primer selected from the group consisting of oligonucleotides P11-P13.

(P11) An oligonucleotide of 10 to 50 nucleotides homologous to nucleotides 86 to 95 of SEQ ID NO: 2, and in which the 3' terminal is the nucleotide C at position 95.

(P12) An oligonucleotide of 10 to 50 nucleotides homologous to nucleotides 64 to 73 of SEQ ID NO: 2, and in which the 3' terminal is the nucleotide C at position 73.

(P13) An oligonucleotide of 10 to 50 nucleotides complementary to nucleotides 155 to 164 of SEQ ID NO: 2, and in which the 3' terminal is the nucleotide C complementary to the nucleotide G at position 155.

The oligonucleotide according to P11 for example includes the oligonucleotide of SEQ ID NO: 18, the oligonucleotide according to P12 for example includes the oligonucleotide of SEQ ID NO: 19, and the oligonucleotide according to P13 for example includes the oligonucleotide of SEQ ID NO: 20.

```
                                      (SEQ ID NO: 18)
    5'-gatcccagaaggtgagaaag-3'
    (EGFR-EX19-F1)

(SEQ ID NO: 19)
    5'-tctctctgtcatagggactc-3'
    (EGFR-EX19-F2)

(SEQ ID NO: 20)
    5'-gaaactcacatcgaggatttc-3'
    (EGFR-EX19-R1)
```

The primers may be a polymorphism detecting primer capable of detecting a genetic mutation in EGFR.

In the reaction system, there is no particular limitation on the primer addition concentration and for example, a single type of primer may have a concentration of 0.1-4 µmol/L, 0.25-1.5 µmol/L, or 0.5-1 µmol/L. Furthermore, when using an F primer and an R primer, there is no particular limitation on the addition ratio of the F primer (F) and the R primer (R) (mole ratio F:R) and for example a ratio of 1:0.25-1:4 or 1:0.5-1:2 may be used.

In step (A), there is no particular limitation on the addition ratio (molar ratio) of the probe for detection of the polymorphism according to the present invention relative to the nucleic acid to be detected, and in light of ensuring a sufficient detection signal, may be no more than times one. The nucleic acid to be detected may be the total of the nucleic acid that includes the wild-type detection sequence and the nucleic acid that includes the mutant-type detection sequence, or may be the total of the amplification product that includes the wild-type detection sequence and the amplification product that includes the mutant-type detection sequence. Although the ratio of the nucleic acid that includes the detection sequence strongly hybridizes with the probe for detection of a polymorphism in the nucleic acid to be detected is normally unknown, as a result, the addition ratio (mole ratio) with the probe for detection of a polymorphism may be no more than 20 times relative to the nucleic acid that includes the detection sequence strongly hybridizes with (the amplification product including the detection sequence described above), no more than 10 times, or no more than 5 times. There is no particular lower limitation, and for example, it may be, at least 0.001 times, at least 0.01 times, or at least 0.1 times. The addition ratio of the probe for detection of the polymorphism according to the present invention relative to the nucleic acid to be detected for example may be a mole ratio relative to the double-stranded nucleic acid, or a mole ratio relative to the single-stranded nucleic acid.

There is no particular limitation on the addition concentration of the probe for detection of a polymorphism according to the present invention in the reaction system, and for example, a single type of probe for detection of a polymorphism may be added in the range of 10-1000 nmol/L, or in the range of 20-500 nmol/L.

There is no limitation on the test sample used in the method of detection of a polymorphism according to the present invention, and it includes a biological sample. Actual examples of the biological sample include whole blood, haemocytes such as white blood cells or the like, bone marrow, cells from the oral cavity such as the tunica mucosa oris or the like, somatic cells such as the nails, hair or the like, reproductive cells, sputum, amniotic fluid, paraffin encased tissue samples, urine, gastric juices, gastric lavage solution, or the like. In the present invention, there is no particular limitation on the method of obtaining the sample, the method of preparing the nucleic acid to be detected from the sample, or the like, and a known and conventional method may be used. For example, when the biological sample is whole blood, the concentration of the whole blood in the reaction system for example, is 0.01-2 volume %, 0.05-1.5 volume %, or 0.1-1 volume %, and when the biological sample is blood serum, the concentration of the blood serum in the reaction system for example, is (0.1-20 volume %, 0.25-15 volume %, or 0.5-10 volume %.

The method of detection of a polymorphism according to the present invention can be used in so-called Tm analysis as described above (hereinafter referred to as melting curve analysis). The Tm value in Tm analysis will be described below. For example, when a solution containing double-stranded DNA is heated, the absorbance at 260 nm increases. The increase results from the breakage of hydrogen bonds between the strands in the double-stranded DNA resulting from the heating, and the dissociation into single-stranded DNA (DNA melting). When all double-stranded DNA dissociates to form single-stranded DNA, the absorbance exhibits approximately a 1.5 increase from the absorbance at which heating started (absorbance when only double-stranded DNA is present). In this manner, completion of melting can be determined. Based on this phenomenon, a melting temperature Tm is generally defined as a temperature at the time when the amount of increase in absorbance reaches 50% of the total amount of increase in absorbance.

In step (A), the measurement of the signal indicating the state of melting of the hybridization product formed from the nucleic acid to be detected and the probe for detection of a polymorphism may be performed by measuring the signal of the fluorescent dye as described above. The labeled probe includes a labeled probe that shows a signal in isolation and does not show a signal upon formation of a hybrid, or a probe that does not show a signal in isolation and shows a signal upon formation of a hybrid. When using the former type of probe, a signal is not exhibited when forming a hybrid (double-stranded DNA) with the amplification product, and a signal is exhibited when the probe dissociates from the amplification product due to heating. Furthermore, when using the latter type of probe, a signal is exhibited when forming a hybrid (double-stranded DNA) with the amplification product, and a signal is decreased (quenched) when the probe dissociates from the amplification product due to heating. Accordingly, by detecting the signal of the fluorescent dye, progress of the melting of the hybridization product and the Tm value can be determined as in the case of the measurement of an absorbance at 260 nm. The signal detection of the fluorescent dye may be performed using a condition that is specific to the signal from the fluorescent dye, and such conditions include for example an excitation wavelength, a detection wavelength and the like. The fluorescent dye and the labeled probe conform to the description above.

Next, an example of the method of detection of a polymorphism according to the present invention will be described. In this example, the probe for detecting a polymorphism according to the present invention that is used in the present example is a labeled probe that is labeled with fluorescent dye. Amplification is performed from a template nucleic acid in the presence of the probe for detecting a polymorphism, and the resulting amplification product is taken to be the nucleic acid to be detected. The method of detection of a polymorphism according to the present invention is characterized by use itself of the probe for detecting a polymorphism according to the present invention, and is not limited in any manner in relation to other steps or conditions.

Firstly, genomic DNA is isolated from the biological sample. The isolation of the genomic DNA from the biological sample may be performed by a known and conventional method. Actual examples include for example a commercially available genomic DNA isolation kit (product name: GFX Genomic Blood DNA Purification Kit, manufactured by GE Healthcare Biosciences).

Next, the labeled probe is added to the sample containing the isolated genomic DNA to thereby prepare a reaction solution. The labeled probe for example as stated above may be a QPROBE.

The labeled probe may be added to the sample containing the isolated genomic DNA, or may be mixed with the genomic DNA in a solvent. There is no particular limitation on the solvent, and examples include known solvents such as a buffering solution such as Tris-HCl, or the like, a solvent containing KCl, $MgCl_2$, $MgSO_4$, glycerol, or the like, or an amplification reaction solution such as a PCR reaction solution.

There is no particular limitation on the timing of addition of the labeled probe, and for example, addition is possible before, during, or after the amplification reaction. Of those options, addition to the reaction solution prior to the amplification reaction may be due to the fact that there is no requirement during addition for exposure of the reaction solution to the external environment, and due to the fact that measurement of the signal value and the amplification reaction can be performed continuously. In this case, as described above, the 3' terminal of the labeled probe may be modified using a labeling substance or a phosphate group.

Next, the sequence containing the detection site generating the target polymorphism is amplified using a method of amplification such as PCR in the presence of the labeled probe using the isolated genomic DNA as a template. Hereinafter, although an example of PCR as a method of amplification will be given to describe the present invention, the present invention is not limited thereby. Furthermore, there is no particular limitation in relation to the conditions for PCR, and performance using a known and conventional method is possible.

More specifically, PCR is performed using the reaction solution above that contains the genomic DNA, the labeled probe and the primer. There is no particular limitation in relation to the composition of the reaction solution and suitable setting thereof may be performed by a person skilled in the art. For example, in addition to the genomic DNA, the labeled probe and the primer, the solution may include polymerases such as DNA polymerase or the like, nucleoside triphosphates, a buffering solution, and various types of catalysts, or the like. There is no particular limitation in relation to the addition ratio of the primer and the labeled probe in the reaction solution, and for example, it may fall within the respective ranges described above.

There is no particular limitation in relation to DNA polymerase, and for example a known and conventional polymerase originating from a thermoduric bacterium may be used, and more specifically, includes commercially available types such as DNA polymerase originating from *Thermus aquaticus* (U.S. Pat. No. 4,889,818, and U.S. Pat. No. 5,079, 352) (product name, Taq polymerase), DNA polymerase originating from *Thermus thermophilus* (WO 91/09950) (rTth DNA polymerase), DNA polymerase originating from *Pyrococcus furiosus* (WO 92/9689) (Pfu DNA polymerase manufactured by Stratagenes), polymerase originating from *Thermococcus litoralis* (EP-A 455 430 (trademark: Vent): manufactured by New England Biolabs), and the like. Of the above, thermoduric polymerase originating from *Thermus aquaticus* may be used.

There is no particular limitation on the addition ratio of the DNA polymerase in the reaction solution, and for example, it may be 1-100 U/mL, 5-50 U/mL, or 2)-40 U/mL. The activity unit of DNA polymerase (U) is generally such that 1 U is the activity when using activated salmon sperm DNA as a template primer, and all nucleotides in 10 nmol are incorporated into an acid-insoluble precipitate in 30 minutes at 74° C. in a reaction solution used for measurement of activity. The composition of the reaction solution used for measurement of activity is for example 25 mmol/L TAPS buffer (pH 9.3, 25° C.), 50 mmol/L KCl, 2 mmol/L $MgCl_2$, 1 mmol/L mercaptoethanol, 200 μmol/L dATP, 200 μmol/L dGTP, 200 μmol/L dTTP, 100 μmol/L "$\alpha$-$^{32}$P" dCTP and 0.25 mg/mL activated salmon sperm DNA.

The nucleoside triphosphates above normally include dNTP (dATP, dCTP, dGTP, and dTTP or dUTP). There is no particular limitation on the addition ratio of dNTP in the reaction solution, and for example, it may be 0.01-1 mmol/L, 0.05-0.5 mmol/L, or 0.1-0.3 mmol/L.

The buffering solution for example includes Tris-HCl, Tricine, MES, MOPS, HEPES, CAPS and the like, and a commercially available PCR buffering solution or commercially available buffering solution for a PCR kit may be used.

The reaction solution may further include heparin, betaine, KCl, $MgCl_2$, $MgSO_4$, glycerol, or the like, and the addition ratio thereof may be set for example within a range that does not impede the PCR reaction.

There is no particular limitation on the overall volume of the reaction solution, and for example, it may be suitably set in response to the equipment used such as a thermal cycler, or the like, and normally has a volume of 1-500 μL, or 10-100 μL.

Next, PCR is performed. There is no particular limitation on the cycle conditions for PCR, and for example, conditions are exemplified below in Table 2 respectively in relation to (1) dissociation of double-stranded DNA that is the nucleic acid to be detected into single-stranded DNA, (2) annealing of the primer to the single-stranded DNA, and (3) extension of the primer using a polymerase reaction. Furthermore, there is no particular limitation on the number of cycles, and when the three steps in (1) to (3) below are taken as one cycle, for example, at least thirty cycles may be performed. There is no particular limitation on the upper limit on the total number of cycles, and for example, it may be no more than 100 cycles, no more than 70 cycles, or no more than 50 cycles. The temperature change in each step may be automatically controlled using a thermal cycler or the like.

TABLE 2

| | Temperature (° C.) and Time (seconds) |
|---|---|
| (1) Dissociation of Single-stranded DNA | For example, 90-99° C., 1-120 seconds or, 92-95° C., 1-60 seconds |
| (2) Primer Annealing | For example, 40-70° C., 1-300 seconds or, 50-70° C., 5-60 seconds |
| (3) Extension Reaction | For example, 50-80° C., 1-300 seconds or, 50-75° C., 5-60 seconds |

There is no particular limitation on the addition ratio of the labeled probe in the reaction solution, and for example, the labeled probe may be added in a range of 10-1000 nmol/L, or in a range of 20-500 nmol/L. For example, the mole ratio of the labeled probe to the nucleic acid to be detected in the reaction solution may be no more than times one in light of ensuring a sufficient signal value. The addition ratio of the labeled probe to the nucleic acid to be detected for example, may be a mole ratio relative to double-stranded nucleic acid, or may be a mole ratio relative to single-stranded nucleic acid.

Next, dissociation of the resulting amplification product (double-stranded DNA) and hybridization is performed using the single-stranded DNA resulting from dissociation and the labeled probe. This may be performed by changing the temperature of the reaction solution in the presence of the labeled probe. In this case, as described above, a reaction solution having the labeled probe added in advance may be subjected to the amplification reaction, and then the temperature of the reaction solution is changed.

There is no limitation on the heating temperature in the dissociation step as long as the double-stranded amplification product can be dissociated into single-strands, and for example, the temperature may be 85-95° C. Furthermore, there is no particular limitation on the heating time, and normally the time is 1 second to 10 minutes, or 1 second to 5 minutes.

The hybridization between the dissociated single-stranded DNA and the labeled probe for example, may be performed after the dissociation step by decreasing the heating temperature in the dissociation step. The temperature condition is for example 40-50° C. Furthermore there is no particular limitation on the processing time at that temperature, and for example, it may be 1-600 seconds.

The temperature of the reaction solution is changed to thereby measure the signal value that indicates the state of melting of the hybridization product formed from the amplification product and the labeled probe. More specifically, for example, the reaction solution (the hybridization body of the single-stranded DNA and the labeled probe) is heated to thereby measure the fluctuation in the signal value associated with the temperature increase. As described above, when using a guanine quenching probe, that is to say, a probe labeled with a terminal cytosine (c), fluorescence is decreased (or quenched) when in a hybridized state with the single-stranded DNA, and fluorescence is emitted when in a dissociated state. Therefore, for example, the hybridization product that exhibits decreasing (or quenching) fluorescence is gradually heated to thereby measure the increase in the fluorescence intensity associated with the temperature increase.

There is no particular limitation on the temperature range when measuring the fluctuation in the fluorescence intensity, and the initial temperature for example, may be from ambient temperature to 85° C., or from 25-70° C. The final temperature for example may be 40-105° C. Furthermore there is no particular limitation on the temperature increase rate, and it may be for example 0.1-2° C. sec, or 0.3-5° C. sec.

Next, the Tm value is determined by analyzing the fluctuation in the signal value. More specifically, a fluorescent intensity change amount per unit time for each temperature (−d fluorescent intensity increase amount/dt) is calculated from the resulting fluorescent intensity and the temperature that exhibits the lowest value is determined as the Tm value. Alternatively, the highest point in the fluorescent intensity increase amount per unit time (d fluorescent intensity increase amount/t) can be determined as the Tm value. In contrast, the decrease amount in the fluorescent intensity may be measured when the labeled probe is not a fluorescent quenching probe but rather a probe that does not exhibit a signal when in isolation and that exhibits a signal when forming a hybrid.

The Tm value can be calculated using known and conventional MELTCALC software (meltcalc.com/) or the like, or may be determined using a nearest neighbor method.

The Tm value is used to determine whether the polymorphism in the EGFR gene is a wild-type variant or a mutant-type variant. In the Tm analysis, the wild-type probe strongly hybridizes with the wild-type detection sequence as compared to the mutant-type detection sequence. Therefore, the Tm value of a double-stranded nucleic acid composed of the wild-type probe and the wild-type detection sequence shows a higher value than the Tm value of a double-stranded nucleic acid composed of the wild-type probe and the mutant-type detection sequence. On the other hand, the mutant-type probe strongly hybridizes with the mutant-type detection sequence as compared to the wild-type detection sequence. Therefore, the Tm value of a double-stranded nucleic acid composed of the mutant-type probe and the mutant-type detection sequence shows a higher value than the Tm value of a double-stranded nucleic acid composed of the mutant-type probe and the wild-type detection sequence. Consequently, determination in advance in relation to the labeled probe of a Tm value ($Tm_H$) in which the probe strongly hybridizes with the detection sequence and a Tm value ($Tm_L$) in which the probe hybridizes with the detection sequence at a value lower than the Tm value ($Tm_B$) enables determination of whether or not the detection sequence includes either the wild-type polymorphism or the mutant-type polymorphism. Further, by preliminarily determining a Tm value ($Tm_H$) in which the wild-type probe strongly hybridizes with the wild-type detection sequence, the sequence can be determined to be the mutant-type detection sequence when a Tm value ($Tm_L$) lower than the Tm value ($Tm_H$) is obtained using the wild-type probe. On the other hand, by preliminarily determining a Tm value ($Tm_H$) in which the mutant-type probe strongly hybridizes with the mutant-type detection sequence, the sequence can be determined to be the wild-type detection sequence when a Tm value ($Tm_L$) lower than the Tm value ($Tm_H$) is obtained using the mutant-type probe.

When the probe that is used is a mutant-type probe, the polymorphism can be determined to be a mutant-type variant when exhibiting the predetermined Tm value ($Tm_B$) with the predetermined mutant-type detection sequence, and the polymorphism can be determined to be a wild-type variant when exhibiting a Tm value ($Tm_L$) lower than the predetermined Tm value ($Tm_H$). When the probe that is used is a wild-type probe, the polymorphism can be determined to be a wild-type variant when exhibiting the predetermined Tm value ($Tm_H$) with the wild-type detection sequence, and the polymorphism can be determined to be a mutant-type variant when exhibiting a Tm value ($Tm_L$) lower than the predetermined Tm value ($Tm_H$).

As described above, in substitution for a method used in the present invention of measuring the signal fluctuation associated with a temperature increase by increasing the temperature of a reaction system including a probe for detecting a polymorphism (heating a hybridization product), for example, measurement of a signal fluctuation may be performed at the time of hybrid formation. That is to say, the temperature of the reaction system including the probe for detecting a polymorphism is decreased to thereby form a hybridization product, and then the signal fluctuation associated with the temperature decrease is measured.

In an actual example, when using a labeled probe that exhibits a signal when in isolation and does not exhibit a signal when forming a hybrid (for example, a guanine quenching probe), although fluorescence is emitted in a state in which the single-stranded DNA is dissociated from the labeled probe, when a hybrid is formed due to a decrease in the temperature, the fluorescence is decreased (or quenched). Therefore, for example, the decrease in the fluorescent intensity associated with the temperature decrease may be measured by gradually decreasing the temperature of the reaction solution. On the other hand, when using a labeled probe that does not exhibit a signal when in isolation and exhibits a signal when forming a hybrid, although fluorescence is not emitted in a state in which the single-stranded DNA is dissociated from the labeled probe, when a hybrid is formed due to a decrease in the temperature, the fluorescence is emitted. Therefore, for example, the increase in the fluorescent intensity associated with a temperature decrease may be measured by gradually decreasing the temperature of the reaction solution.

As described above, the present invention enables use of two or more types of probes for detection of a polymorphism in a single reaction system. When using a plurality of probes for detection of a polymorphism, the timing of addition of each probe for example may be as described above, and simultaneous addition in advance of step (A) may be performed. When executing an amplification reaction, simultaneous addition in advance of the amplification reaction may be performed.

The plurality of probes for example may be a combination of an EGFR858 probe and an exon19 probe, and more specifically, includes examples such as a combination of an EGFR858 probe and an exon19 wild-type probe, a combination of an EGFR858 probe and an exon 19 mutant-type (del) probe, and a combination of an EGFR858 probe and an exon 19 wild-type probe and an exon 19 mutant-type (del) probe. In the present invention, for example, the combination may further include the EGFR790 probe.

When detecting both the EGFR858 polymorphism and the exon 19 polymorphism in a single reaction system, for example, a combination of the EGFR858 probe and the exon 19 probe may be used. At that time, the EGFR858 probe and the exon19 probe as described above may include respectively different labeling substances. The respective Tm values can be determined by detecting a signal corresponding to the measurement conditions of each labeling substance by changing the temperature of the reaction system.

Detection of the EGFR5 polymorphism or the EGFR790 polymorphism is enabled, for example, by respectively combining a wild-type probe and a mutant-type probe in relation to the target polymorphism. In this case, for example, determination of the type of polymorphism is enabled by which probe exhibits a Tm of the hybrid that is a completely complementary match. For example, when using a wild-type probe and a mutant-type probe that have different labeling substances, the polymorphism is determined to be a mutant-type variant when the mutant-type probe exhibits a Tm value of the hybrid that is a completely complementary match, and the polymorphism is determined to be a wild-type variant when the wild-type probe exhibits a Tm value of the hybrid that is a completely complementary match.

The mutant may be located anywhere in the probe described herein provided that the location of the mismatch allows for a change in the melting temperature between the mutant and wild-type sequences. Accordingly, when the probe does not exhibit completely complementary match to a sample, the mismatch may be located anywhere in the probe. Specifically, the mismatch may be a 3' or 5' terminal mismatch. In other embodiments, the mismatch may be located at or near the center of the probe such that the mismatch is most likely to destabilize the duplex with the target sequence under the test hybridization conditions. The method of detecting a polymorphism according to the present invention enables a combination of the probe for detecting a polymorphism according to the present invention for detecting a polymorphism in an EGFR gene and a probe for detecting a polymorphism in another gene. The combination of the probe for detecting a polymorphism according to the present invention and the probe for detecting a polymorphism in another gene enables detection of a polymorphism in two or more genes including the EGFR gene. There is no particular limitation on the other polymorphisms in the EGFR gene, and for example, includes the EGFR790 polymorphism.

Determination Method

The determination method according to the present invention is characterized by execution of the method for detecting a polymorphism by use of the probe for detecting a polymorphism according to the present invention, and there are no other limitations in respect of other steps or conditions. The determination of the efficacy of or resistance to EGFR-TKI due to a polymorphism is for example performed according to a known standard.

Reagent Kit

The reagent kit for detection of a polymorphism in the EGFR gene according to the present invention is characterized by inclusion of the probe for detecting a polymorphism according to the present invention. There are no other limitations in respect of other configurations as king as the reagent kit according to the present invention contains the probe according to the present invention. The probe according to the present invention included in the reagent kit according to the present invention may be a single type or two or more types, and for example, a combination may be included as described above. The reagent kit according to the present invention for example may include the primer according to the present invention as described above. The combination of primers may be in accordance with the above description without any particular limitation thereon. The reagent kit according to the present invention for example may further include required components for the amplification reaction of the nucleic acid, explanatory materials, and the like.

Primer Reagent

The primer reagent according to the present invention may contain any one type of primer according to the present invention, or may contain two or more types. The type of primer for example may be suitably set in response to the target amplification domain. When amplifying a detection sequence including the EGFR858 polymorphism, at least one of the primers con figured from the oligonucleotides according to P8, P9 and P10 may be included, and in particular, at least one primer selected from the group consisting of the oligonucleotides of SEQ ID NO: 15, SEQ ID NO: 16 and SEQ ID NO: 17 may be included. When amplifying a detection sequence including the exon 19 polymorphism, at least one of the primers formed from the oligonucleotides according to P11, P12 and P13 may be included, and in particular, at least one primer selected from the group consisting of the oligonucleotides of SEQ ID NO: 18, SEQ ID NO: 19 and SEQ ID NO: 20 may be included. The primer reagent according to the present invention for example enables amplification of a detection sequence including the EGFR858 polymorphism and the detection sequence including the exon19 polymorphism by having a primer that includes the oligonucleotide according to P8, and the oligonucleotide according to P9 or P10, the oligonucleotide according to P11 or P12, and the oligonucleotide according to P13. Furthermore, although a combination of primers has been described above, there is no limitation in this regard.

Reagent for Detection of Polymorphism

The reagent for detection of a polymorphism according to the present invention is a reagent for detection of a polymorphism in an EGFR gene, and is characterized by inclusion of the probe for detection of a polymorphism according to the present invention. In the present invention, there are no other limitations in respect of other configurations or conditions other than the characteristic of including the probe for detection of a polymorphism according to the present invention. The reagent for detection of a polymorphism according to the present invention for example can be said to be a probe kit used in the detection of a polymorphism in the EGFR gene.

The reagent for detection of a polymorphism for example may include one type of probe for detection of a polymorphism, or two or more types, and may be suitably set in response to the polymorphism that is the target of detection. When detecting only the EGFR858 polymorphism, for example, the EGFR858 probe may be included. The EGFR858 probe for example may be the EGFR858 wild-type probe, may be the EGFR858 mutant-type probe, or may include both. Furthermore, when detecting only the exon 19 polymorphism, for example, the exon19 probe may be included. The exon19 probe for example may be any one of the exon19 wild-type probe, may be the exon 19 mutant-type (sub) probe, may be the exon 19 mutant-type (del) probe, may include two types, or may include all types. Furthermore, although a combination of probes has been described above, there is no limitation in this regard.

Reagent Kit for Detection of Polymorphism

The reagent kit for detection of a polymorphism according to the present invention is a reagent kit for use in detection of a polymorphism in the EGFR gene, and is characterized by inclusion of the probe according to the present invention. One type or two or more types of the probe according to the present invention may be provided in the reagent kit according to the present invention. In the latter configuration, the two or more probes may be included in a mixed configuration, or may be included as separate reagents. Furthermore, when included in a probe kit according to the present invention in a configuration in which two or more probes according to the present invention are mixed, or when executing Tm analysis of each probe and each detection target sequence in the same reaction system at the same time although included as separate reagents, each probe may be labeled with separate fluorescent substances. The variation of the type of fluorescent substance in this manner enables detection of respective probes even in the same reaction system. The fluorescent substance may be a substance having a different detection wavelength.

The reagent kit for detection of a polymorphism in an EGFR gene may include a primer set for the amplification of a sequence including the polymorphic site (domain with which the probe undergoes hybridization).

EXAMPLES

The examples of the present invention will be described below. However, the present invention is not limited by the examples.

Example 1

Tm analysis was performed in the common presence of a wild-type plasmid and a mutant-type plasmid in order to detect an EGFR858 polymorphism in an EGFR gene.

The wild-type plasmid and a mutant-type plasmid are prepared as an EGFR858 wild-type plasmid (L858WT) and as an EGFR858 mutant-type plasmid (L858R). The EGFR858 wild-type plasmid (L858WY) includes a partial sequence of the EGFR gene by insertion of the oligonucleotides from position 112 to position 411 of SEQ ID NO: 1, and in which the nucleotide (k) at position 261 of SEQ ID NO: 1 is thymine (t). The EGFR858 mutant-type plasmid (L858R) includes a partial sequence of the EGFR gene by insertion of the oligonucleotides from position 112 to position 411 of SEQ ID NO: 1, and in which the nucleotide (k) at position 261 of SEQ ID NO: 1 is guanine (g). These plasmids are mixed in a predetermined ratio as shown below to thereby prepare three types of samples. These samples include 250 plasmid copies per μL.

TABLE 3

| Sample | | Mixing Ratio by Plasmid | |
|---|---|---|---|
| | | L858WT | L858R |
| L858WT | 100% | 100% | 0% |
| L858R | 5% | 95% | 5% |
| L858R | 10% | 90% | 10% |

PCR and Tm analysis were performed in relation to 50 μL of PCR reaction solution as illustrated in Table 4 using a fully automatic SNPs detection apparatus (product name: i-densy (trademark) IS-5310 manufactured by Arkray Inc.). PCR included repetition of 50 cycles after processing at 95° C. for one minute with a single cycle being one second at 95° C. and 15 seconds at 58° C., and then processing for one second at 95° C. and 60 seconds at 40° C. Then, the reaction solution was heated from 40° C. to 75° C. with a rate of temperature increase being 1° C./3 seconds to thereby perform Tm analysis by measurement of the change in the fluorescence intensity over time at a detection wavelength of 585-700 nm.

TABLE 4

| (Composition of PCR Reaction Solution: units μL) | |
|---|---|
| Distilled Water | 33.61 |
| 0.94 U/μL Taq polymerase | 2 |
| 10 w/v % NaN$_3$ | 0.23 |
| 100 mmol/L MgCl$_2$ | 0.75 |
| 1 mol/L KCl | 1.25 |
| 1 mol/L Tris-HCl(pH 8.6) | 1.25 |
| 2.5 mmol/L dNTP | 4 |
| 20 w/v % BSA | 0.5 |
| 80 w/v % glycerol | 1.56 |
| 100 μmol/L EGFR858 probe | 0.1 |
| 100 μmol/L EGFR858 F primer | 0.5 |
| 100 μmol/L EGFR858 R primer | 0.25 |
| Sample | 4 |
| Total | 50 μL |

The sequence of the EGFR858 primer is shown below.

```
F primer
                              (SEQ ID NO: 15)
5'-aggaacgtactggtgaaaacaccgc-3'
(EGFR-L858R-F2)

R primer
                              (SEQ ID NO: 16)
5'-ttactttgcctccttctgatggtattc-3'
(EGFR-L858R-R2)
```

The EGFR858 primer that was used is the EGFR858 mutant-type probe having the sequence below. The EGFR858 mutant-type probe is a mutant-type probe in the sense strand of the EGFR858 mutant-type EGFR gene. In the sequence, the nucleotide that is underlined is a nucleotide that is complementary to the EGFR858 mutant-type variant, and the EGFR858 mutant-type probe was labeled with a fluorescent dye TAMRA at the 3' terminal.

(SEQ ID NO: 7)
EGFR858 mutant-type probe (3T-EGFR-858-R2)
5'-ttgccc<u>c</u>gcccaaaatc-(TAMRA)-3'

The results are illustrated in FIG. 1. FIG. 1 is a graph of the Tm analysis showing the change in the fluorescent intensity associated with temperature increase. In FIG. 1, (A) is the result for L858WT 100%, (B) is the result for L958R 5%, and (C) is the result for L858R 10%. The horizontal axis shows the temperature (° C.) during measurement, and the vertical axis shows the change in the fluorescent intensity (hereinafter referred to as "fluorescent change amount". The units are shown as "d fluorescent intensity increase amount/dt" (dF/dt). The Tm value of the L858WT and EGFR858 mutant-type probe is in proximity to 55° C., and the Tm value of the L858R and EGFR858 mutant-type probe is in proximity to 64° C.

As illustrated in FIG. 1(A), the L858WT Tm value is the only confirmed peak for L858WT 100%. On the other hand, as illustrated in FIG. 1(C), peaks were confirmed at both the Tm value for L858WT and the Tm value for L858R for L858R 10% that includes 10% mutant-type plasmid. As illustrated in FIG. 1(B), peaks were confirmed at both the Tm value for L858WT and the Tm value for L858R for L858R 5% in which the content of the mutant-type plasmid is reduced to 5%.

Example 2

In the present example, Tm analysis was respectively executed in relation to wild-type artificial nucleic acid and mutant-type artificial nucleic acid to thereby detect the EGFR 858 polymorphism in the EGFR gene.

EGFR858 wild-type artificial nucleic acid (EGFR-L858R (WT)-F) and EGFR858 mutant-type artificial nucleic acid (EGFR-L858R(MT)-F) that is homologous to positions 241 to 290 SEQ ID NO: 1 as illustrated in the sequence below were prepared. In the following two sequences, the underlined portion corresponds to the nucleotide at position 261 SEQ ID NO: 1. The respective artificial nucleic acids were adjusted to 5 µmol/L and were used as test samples.

(SEQ ID NO: 32)
EGFR-L858R(WT)-F
caagatcacagatttgggc<u>t</u>ggccaaactgctgggtgcggaagagaaag (SEQ ID NO: 33)
EGFR-L858R(MT)-F
caagatcacagatttgggcgggccaaactgctgggtgcggaagagaaag Tm analysis was performed in relation to 25 µL of the reaction solution as illustrated in Table 5 using a fully automatic SNPs detection apparatus (product name: i-densy (trademark) IS-5310 manufactured by Arkray Inc.). Tm analysis was performed by processing at 95° C. for one second and 60 seconds at 40° C. Then, the reaction solution was heated from 40° C. to 75° C. with a rate of temperature increase being 1° C./3 seconds to thereby measure the change in the fluorescence intensity over time at a detection wavelength of 585-700 nm.

TABLE 5

| (Composition of Reaction Solution: units µL) | |
|---|---|
| Distilled water | 21 |
| 10× GeneTaq buffer*[1] | 2.5 |
| 5 µmol/L EGFR858 mutant-type probe | 0.5 |
| 5 µmol/L Sample | 1 |
| Total | 25 µL |

*[1]manufactured by Nippongene

The EGFR858 mutant-type probe is a mutant-type probe in the sense strand of the EGFR858 mutant-type EGFR gene. In the sequence, the underlined nucleotide corresponds to the nucleotide which is complementary to the EGFR858 mutant-type variant. The EGFR858 mutant-type probe was labeled with a fluorescent dye TAMRA at the 3' terminal.

(SEQ ID NO: 9)
EGFR858 mutant-type probe (3T-EGFR-858-R1)
5'-cagtttggcc<u>c</u>gccc-(TAMRA)-3'

Figure 2:
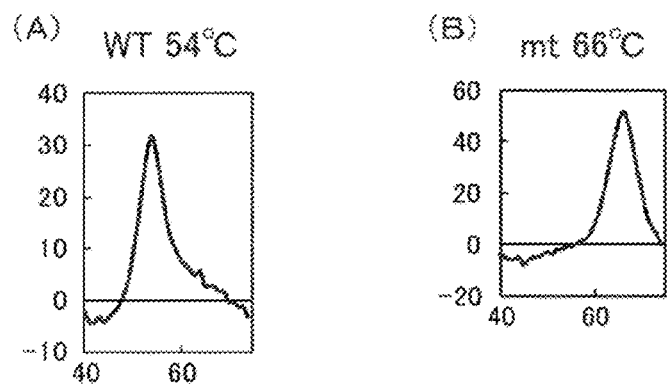
FIG. 2 depicts graphs (A)-(B) illustrating the results of Tm analysis of a reaction solution using different samples according to example 2 of the present invention.

The results are illustrated in FIG. 2. FIG. 2 is a graph of the Tm analysis showing the change in the fluorescent intensity associated with temperature increase. In FIG. 2, (A) is the result for EGFR-L858R(WT)-F and (B) is the result for EGFR-L858R(MT)-F. The horizontal axis shows the temperature (° C.) during measurement, and the vertical axis shows the change in the fluorescent intensity (hereinafter referred to as "fluorescent change amount"). The units are illustrated as "d fluorescent intensity increase amount/dt" (dF/dt). The Tm value of the EGFR-L851R(WT)-F and EGFR858 mutant-type probe is in proximity to 54° C., and the Tm value of the EGFR-L858R(MT)-F and EGFR858 mutant-type probe is in proximity to 66° C.

As illustrated in FIG. 2(A), the EGFR-L858R(WT)-F Tm value is the only confirmed peak for EGFR-L858R(WT)-F. On the other hand, as illustrated in FIG. 2(B), the EGFR-L858R(MT)-F Tm value is the only confirmed peak for EGFR-L858R(MT)-F.

Example 3

In the present example, Tm analysis was performed in relation to wild-type oligonucleotides and mutant-type oligonucleotides to thereby detect the EGFR gene exon19 polymorphism. The detection wavelength of BODIPY FL was 520-555 nm, and the detection wavelength of TAMRA was 585-700 nm.

(1) Oligonucleotide

The wild-type and mutant-type oligonucleotides were prepared using the oligonucleotides 1-8 in Table 6. These oligonucleotides are sequences that are complementary to the sense strand of the EGFR gene. The oligonucleotide 1 is the wild-type oligonucleotide, and is complementary to the partial sequence of the sense strand including the exon 19 polymorphism 1. The oligonucleotides 2-18 are the mutant-type oligonucleotides, and are complementary to the partial sequence of the sense strand including the exon 19 polymorphisms 2-18. Table 6 shows the corresponding domain in the nucleotide sequence of SEQ ID NO: 2 for each oligonucleotide. The range of the nucleotide sequence continuing from the triangle is the deletion site.

TABLE 6

(Oligonucleotide)

| No. | Base Sequence | Tm value (° C.) | Corresponding domain of SEQ ID NO: 2 |
|---|---|---|---|
| 1 | 5'-ttccttgttggctttcggagatgttgcttctcttaattccttgatagcgacgggaattttt-3' | 74 | 98-157 |
| 2 | 5'-tcgaggatttccttgttggctttcggagatgttttgatagcgacgggaattttaactttc-3' | 87 | 91-157(Δ118-132) |
| 3 | 5'-tcgaggatttccttgttggctttcggagatgtcttgatagcgacgggaattttaactttc-3' | 60 | 91-165(Δ119-133) |
| 4 | 5'-gatttccttgttggctttcggagatgttggttccttgatagcgacgggaattttaacttt-3' | 65 | 92-160(Δ122-130, G131C) |
| 5 | 5'-tcgaggatttccttgttggctttcggagattccttgatagcgacgggaattttaactttc-3' | 60 | 91-165(Δ123-137) |
| 6 | 5'-atcgaggatttccttgttggctttcgattccttgatagcgacgggaattttaactttctc-3' | 66 | 89-166(Δ123-140) |
| 7 | 5'-aggatttccttgttggctttcggagatggttccttgatagcgacgggaattttaactttc-3' | 66 | 91-162(Δ122-133, A134C) |
| 8 | 5'-catcgaggatttccttgttggctttcggttccttgatagcgacgggaattttaactttct-3' | 65 | 90-167(Δ122-140) |
| 9 | 5'-catcgaggatttccttgttggctttcggaaccttgatagcgacgggaattttaactttct-3' | 64 | 90-167(Δ120-137, C138T) |
| 10 | 5'-ggatttccttgttggctttcggagatgcttccttgctagcgacgggaattttaactttct-3' | 67 | 90-161(Δ123-134) |
| 11 | 5'-catcgaggatttccttgttggctttcgattccttgatagcgacgggaattttaactttct-3' | 65 | 90-167(Δ123-140) |
| 12 | 5'-catcgaggatttccttgttggctttctgttccttgatagcgacgggaattttaactttct-3' | 65 | 90-167(Δ122-139, C141A) |
| 13 | 5'-tcgaggatttccttgttggctttcggagataccttgatagcgacgggaattttaactttc-3' | 63 | 91-165(Δ120-134, C135T) |
| 14 | 5'-acatcgaggatttccttgttggctttcggaaccttgatagcgacgggaattttaactttc-3' | 64 | 91-168(Δ121-138, A120T) |
| 15 | 5'-acatcgaggatttccttgttggctttcggaattttgatagcgacgggaattttaactttc-3' | 68 | 91-168(Δ118-135, T137A, C137T) |
| 16 | 5'-tcgaggatttccttgttggctttcggagatatcttaattgcgacgggaattttaactttc-3' | 50 | 91-165(Δ112-119, Δ129-135, G128T) |
| 17 | 5'-tcgaggatttccttgttggctttcggttgttccctgatagcgacgggaattttaactttc-3' | 65 | 91-165(Δ122-131, Δ135-139) |
| 18 | 5'-cgaggatttcctttgttgcttctcttaattccttgatagcgacgggaattttaactttct-3' | 66 | 90-164(Δ137-151) |

*Sequences 1-18 are respectively shown as SEQ ID NOs: 49-66.

(2) Tm Analysis

Tm analysis was performed in relation to 25 μL of the reaction solution as illustrated in Table 7 using a fully automatic SNPs detection apparatus (product name: i-densy (trademark) IS-5310 manufactured by Arkray Inc.). Tm analysis was performed by processing at 95° C. for one second and 60 seconds at 40° C. Then, the reaction solution was heated from 40° C. to 75° C. with a rate of temperature increase being 1° C./3 seconds to thereby measure the change in the fluorescence intensity over time at a detection wavelength corresponding to each fluorescent dye. Furthermore, a negative control was prepared by adding 5 μL of distilled water to 25 μL of the reaction solution instead of 5 μL of sample and measuring the change in the fluorescence intensity over time in the same manner.

TABLE 7

(Composition of Reaction Solution: units μL)

| | |
|---|---|
| Distilled water | 17.4 |
| ×10 GeneTaq buffer*[1] | 2.5 |
| 100 μmol/L exon19 probe | 0.1 |
| 5 μmol/L Sample | 5 |
| Total | 25 μL |

*[1]manufactured by Nippongene

Example 3-1

The oligonucleotides 1-18 were adjusted to 5 μmol/L. Samples of the reaction solution were prepared using a sample 1s of the oligonucleotide 1 in isolation and samples 2m-18m in which the oligonucleotide 1 and the oligonucleotides 2-18 are mixed in a volume ratio of 1:4.

Probes with the sequences below were used as exon19 probes. The probes have sequences perfectly complementary to the wild-type oligonucleotide 1, and the Tm value of the probe and the wild-type oligonucleotide 1 is in proximity to 74° C.

(SEQ ID NO: 5)
exon19 wild-type probe (5FL-EGFR-EX19-F2)
5'-(BODIPY FL)-cccgtcgctatcaaggaattaagagaagc-3'

Figure 9:
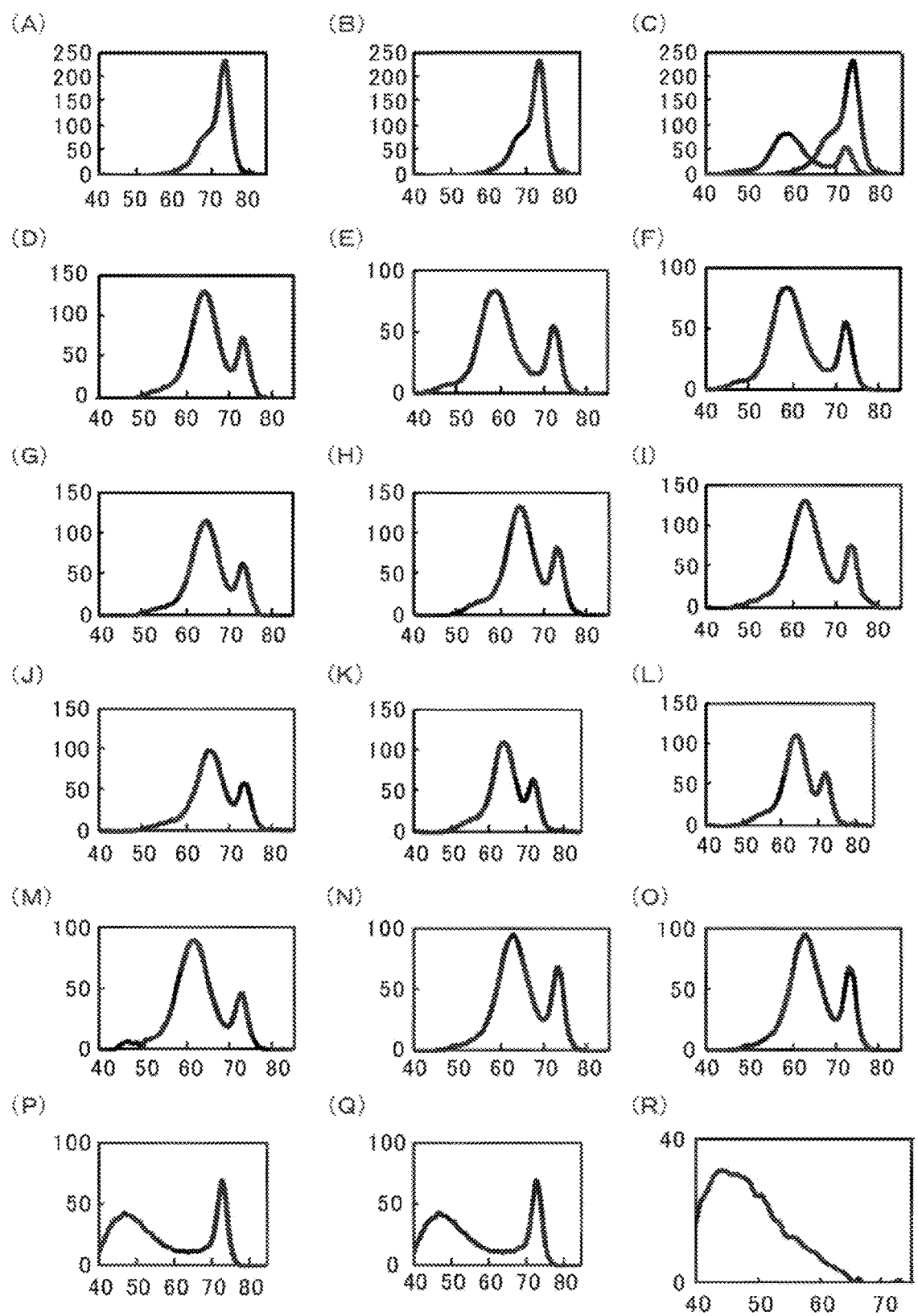
FIG. 9 depicts graphs (A)-(R) illustrating the results of Tm analysis of a reaction solution using different samples according to an example 3-1 of the present invention.

The results are illustrated in FIG. 9. FIG. 9 is a graph of the Tm analysis showing the change in the fluorescent intensity associated with temperature increase. In FIG. 9, (A)-Q) are the results in order for detection of the fluorescent dye in relation to samples 1s, 2m-17m. (R) shows the results for the negative control. The horizontal axis shows the temperature (° C.) during measurement, and the vertical axis shows the change in the fluorescent intensity (hereinafter referred to as "fluorescent change amount"). The units are shown as "d fluorescent intensity increase amount/dt" (dF/dt).

Table 8 shows the results of Tm analysis in relation to each sample for peak number. Tm value of each peak and the difference between the Tm value for each peak and the Tm value (74° C. for the wild-type oligonucleotide 1 (Δ° C.). As illustrated in Table K and FIG. 9, the sample 1s including only the wild-type oligonucleotide 1 exhibits a peak only at the Tm value (74° C.) for the wild-type oligonucleotide 1. The samples 2m-17m including the wild-type oligonucleotide 1 and the mutant-type oligonucleotides 2-17 have two respective peaks. In other words, the samples 2m-17m have peaks at the Tm value of the wild-type oligonucleotide 1 and the exon19 wild-type probe and also at a lower temperature. The sample 18 that contains the mutant-type oligonucleotide 18 has a peak only at the Tm value (74° C.) for the wild-type oligonucleotide 1, and a peak was not confirmed at any other temperature.

TABLE 8

| Sample | Number of Peaks | Peak 1 | | Peak 2 | |
|---|---|---|---|---|---|
| | | Tm(° C.) | Δ(° C.) | Tm(° C.) | Δ(° C.) |
| 1s | 1 | 74 | — | | |
| 2m | 2 | 74 | — | 57 | 17 |
| 3m | 2 | 74 | — | 60 | 14 |
| 4m | 2 | 74 | — | 65 | 9 |
| 5m | 2 | 74 | — | 60 | 14 |
| 6m | 2 | 74 | — | 66 | 8 |
| 7m | 2 | 74 | — | 66 | 8 |
| 8m | 2 | 74 | — | 65 | 9 |
| 9m | 2 | 74 | — | 64 | 10 |
| 10m | 2 | 74 | — | 67 | 7 |
| 11m | 2 | 74 | — | 65 | 9 |
| 12m | 2 | 74 | — | 65 | 9 |
| 13m | 2 | 74 | — | 63 | 11 |
| 14m | 2 | 74 | — | 64 | 10 |
| 15m | 2 | 74 | — | 58 | 16 |
| 16m | 2 | 74 | — | 50 | 24 |
| 17m | 2 | 74 | — | 65 | 9 |
| 18m | 1 | 74 | — | x | x |

Example 3-2

The oligonucleotides 1-18 were adjusted to 5 μmol/L. Samples of the reaction solution were prepared using a sample 1s of the oligonucleotide 1 in isolation and the samples 2m-18m in which the oligonucleotide 1 and the oligonucleotides 2-18 are mixed in a volume ratio of 1:4.

Probes with the sequences below were used as exon19 probe. The probe has a sequence perfectly complementary to the mutant-type oligonucleotide 18, and the Tm value of the probe and the mutant-type oligonucleotide 18 is in proximity to 58° C.

(SEQ ID NO: 6)
exon 19 mutant-type (del) probe (3T-EGFR-EX19-No. 18-F1)
5'-agcaacaaaggaaatc-(TAMRA)-3'

Figure 10:
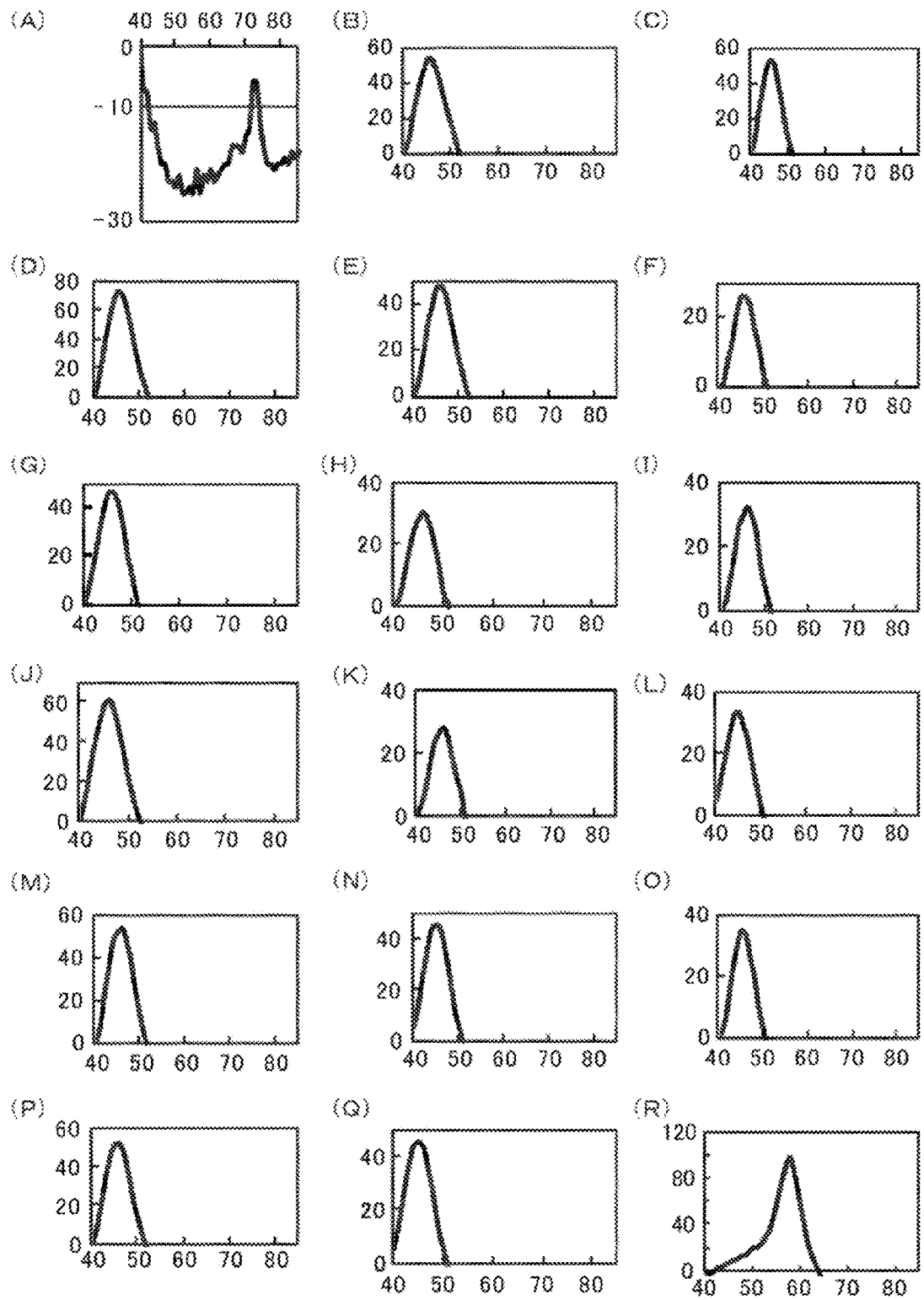
FIG. 10 depicts graphs (A)-(R) illustrating the results of Tm analysis of a reaction solution using different samples according to an example 3-2 of the present invention.

The results are illustrated in FIG. 10. FIG. 10 is a graph of the Tm analysis showing the change in the fluorescent intensity associated with temperature increase. In FIG. 10, (A)-(R) are the results in order for detection of the fluorescent dye in relation to samples 1s, 2m-18m. The horizontal axis shows the temperature (° C.) during measurement, and the vertical axis shows the change in the fluorescent intensity (hereinafter referred to as "fluorescent change amount"). The units are shown as "d fluorescent intensity increase amount/dt" (dF/dt).

Table 9 shows the results of Tm analysis in relation to each sample for peak number. Tm value of each peak and the difference between the Tm value for each peak and the Tm value (58° C.) for the mutant-type oligonucleotide 18 (Δ° C.). As illustrated in Table 9 and FIG. 10, the sample 18m including the mutant-type oligonucleotide 18 has a peak only at the Tm value (58° C.) for the mutant-type oligonucleotide 18. A peak was not confirmed in relation to the sample 1s that includes only the wild-type oligonucleotide 1. Furthermore, the samples 2m-17m that include oligonucleotides other than the mutant-type oligonucleotide 18 have a peak at a lower temperature than the sample 18m.

TABLE 9

| Sample | Number of Peaks | Peak 1 | |
|---|---|---|---|
| | | Tm(° C.) | Δ(° C.) |
| 1s | x | x | x |
| 2m | 1 | 46 | 12 |
| 3m | 1 | 46 | 12 |
| 4m | 1 | 46 | 12 |
| 5m | 1 | 47 | 11 |
| 6m | 1 | 47 | 11 |
| 7m | 1 | 47 | 11 |
| 8m | 1 | 47 | 11 |
| 9m | 1 | 47 | 11 |
| 10m | 1 | 47 | 11 |
| 11m | 1 | 47 | 11 |
| 12m | 1 | 46 | 12 |
| 13m | 1 | 47 | 11 |
| 14m | 1 | 46 | 12 |
| 15m | 1 | 46 | 12 |
| 16m | 1 | 47 | 11 |
| 17m | 1 | 46 | 12 |
| 18m | 1 | 58 | — |

Example 3-3

The oligonucleotides 1-18 were adjusted to 5 μmol/L. Samples (1s-18s) of the reaction solution wet respectively used in isolation.

Probes with the sequences below were used as exon 19 probes. The probes have sequences complementary to the wild-type oligonucleotide 1 except that the nucleotide at position 119 in SEQ ID NO: 1 is t, and the Tm value of the probe and the wild-type oligonucleotide 1 is in proximity to 67° C.

```
                                              (SEQ ID NO: 4)
exon19 mutant-type (sub) probe (5FL-EGFR-EX19No.
19-F2-3)
5'-(BODIPY FL)-cccgtcgctatcaagtaattaagagaagcaaca-
3'
```

Figure 11:
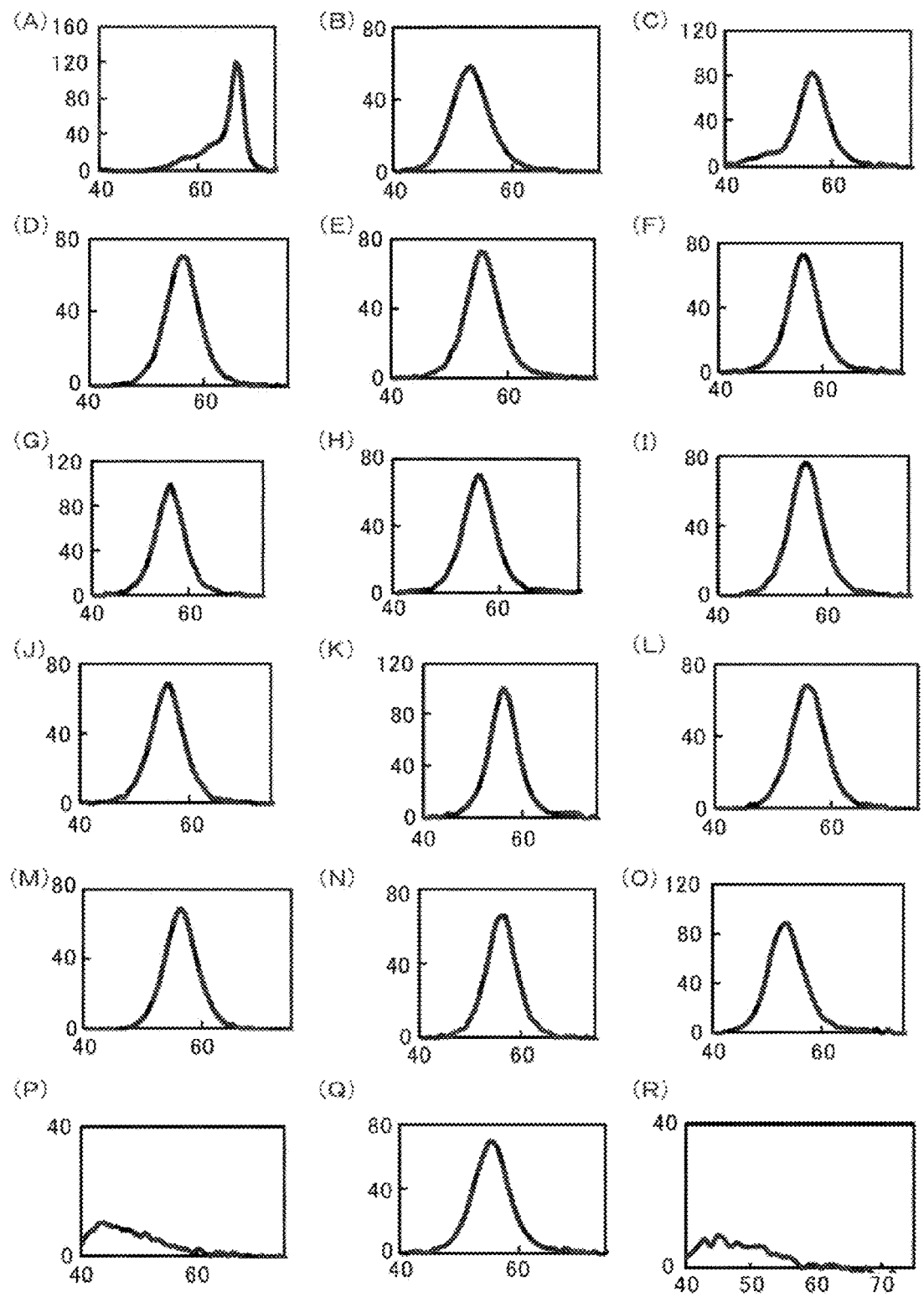
FIG. 11 depicts graphs (A)-(R) illustrating the results of Tm analysis of a reaction solution using different samples according to an example 3-3 of the present invention.

The results are illustrated in FIG. 11. FIG. 11 is a graph of the Tm analysis showing the change in the fluorescent intensity associated with temperature increase. In FIG. 11, (A)-(Q) are the results in order for detection of the fluorescent dye in relation to samples 1s-17s. (R) shows the results of the negative control. The horizontal axis shows the temperature (° C.) during measurement, and the vertical axis shows the change in the fluorescent intensity (hereinafter referred to as "fluorescent change amount"). The units are shown as "d fluorescent intensity increase amount/dt" (dF/dt).

Table 10 shows the results of Tm analysis in relation to each sample for peak number, Tm value of each peak and the difference between the Tm value for each peak and the Tm value (67° C.) for the wild-type oligonucleotide 1 (Δ° C.). As illustrated in Table 10 and FIG. 11, the sample 1s including only the wild-type oligonucleotide 1 has a peak only at the Tm value (67° C.) for the wild-type oligonucleotide 1. The samples 2s-15s and 17s including only the mutant-type oligonucleotides 2-15 and 17 have respective peaks at a temperature that is lower than the Tm value of the wild-type oligonucleotide 1. A peak was not confirmed in relation to the samples 16s and 18s that include only the mutant-type oligonucleotide 16 or 18.

TABLE 10

| Sample | Number of Peaks | Peak 1 Tm(° C.) | Δ(° C.) |
|---|---|---|---|
| 1s | 1 | 67 | — |
| 2s | 1 | 53 | 14 |
| 3s | 1 | 56 | 11 |
| 4s | 1 | 56 | 11 |
| 5s | 1 | 55 | 12 |
| 6s | 1 | 56 | 11 |
| 7s | 1 | 56 | 11 |
| 8s | 1 | 56 | 11 |
| 9s | 1 | 56 | 11 |
| 10s | 1 | 56 | 11 |
| 11s | 1 | 56 | 11 |
| 12s | 1 | 56 | 11 |
| 13s | 1 | 56 | 11 |
| 14s | 1 | 56 | 11 |
| 15s | 1 | 56 | 11 |
| 16s | x | x | x |
| 17s | 1 | 55 | 12 |
| 18s | x | x | x |

Comparative Example 3

The oligonucleotides 1-18 were adjusted to 5 μmol/L. Samples (1s-18s) of the reaction solution were respectively used in isolation.

Probes with the sequences below were used as exon 19 probes. The probes have sequences strongly hybridize with the wild-type oligonucleotide 1, and the Tm value of the probe and the wild-type oligonucleotide 1 is in proximity to 72° C.

```
                                             (SEQ ID NO: 28)
exon19 wild-type probe (5FL-EGFR-EX19-WT-F1)
5'-(BODIPY FL)-caaggaattaagagaagcaacatctccg-3'
```

Figure 12:
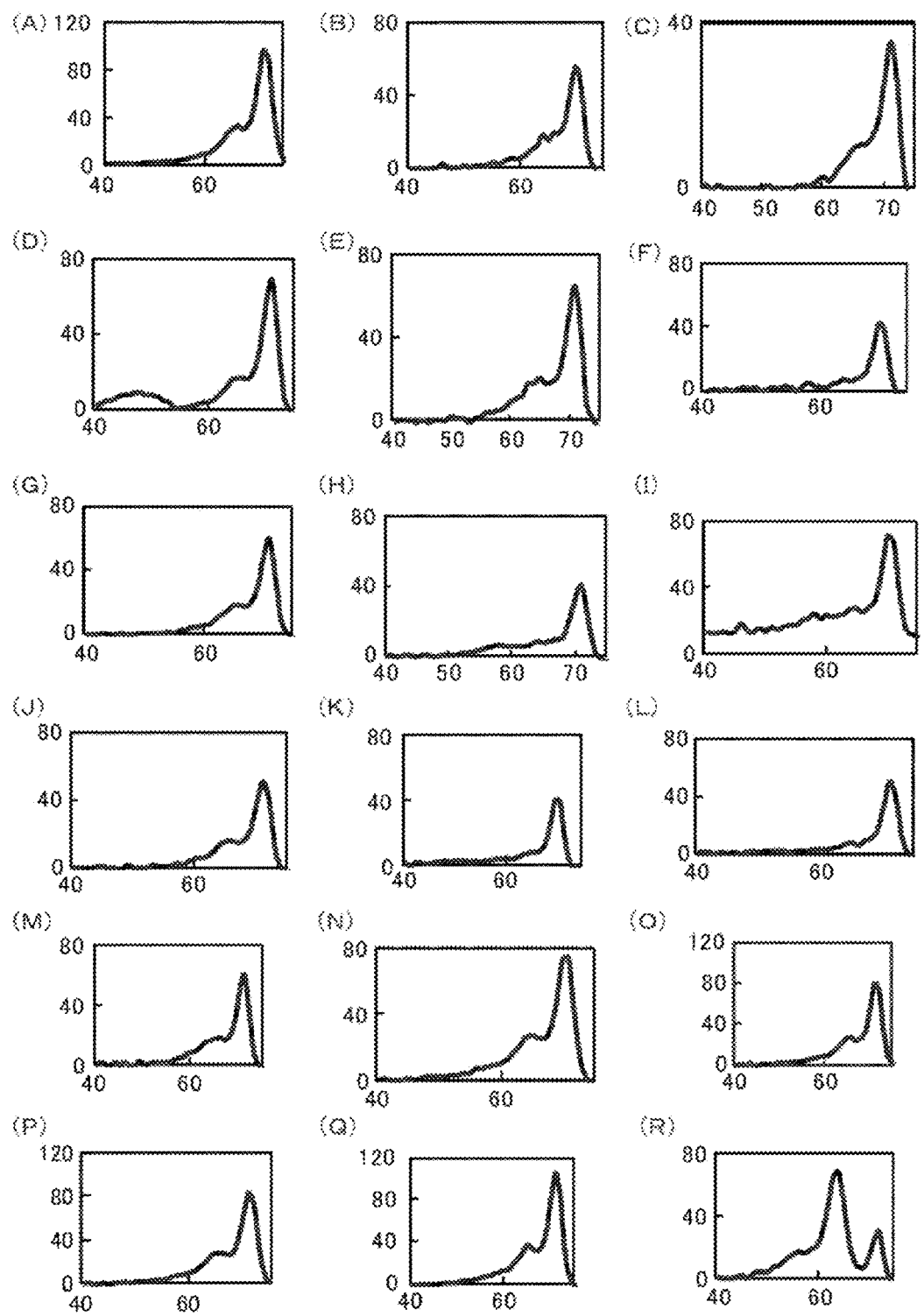
FIG. 12 depicts graphs (A)-(R) illustrating the results of Tm analysis of a reaction solution using different samples according to comparative example 3.

The results are illustrated in FIG. 12. FIG. 12 is a graph of the Tm analysis showing the change in the fluorescent intensity associated with temperature increase. In FIG. 12, (A)-(R) are the results in order for detection of the fluorescent dye in relation to samples 1s-18s. In each graph, the horizontal axis shows the temperature (° C.) during measurement, and the vertical axis shows the change in the fluorescent intensity (hereinafter referred to as "fluorescent change amount"). The units are shown as "d fluorescent intensity increase amount/dt" (dF/dt). Table 11 shows the results of Tm analysis show that for each sample in relation to the difference between the Tm value for the largest peak and the Tm value (72° C.) for the wild-type olignucleotide 1 and the peak Tm value.

As illustrated in FIG. 12, the peak for sample 1s exhibits a shoulder irrespective of whether including only the wild-type oligonucleotide 1, and it is not possible to discriminate whether it is the wild-type oligonucleotide or the mutant-type oligonucleotide. Furthermore a plurality of peaks is confirmed in relation to the samples 2s-18s including only the mutant-type oligonucleotide 2-18. As illustrated in Table 11, the Tm value for the largest peak of the samples 2s-18s exhibits almost no difference from the Tm value of the wild-type oligonucleotide 1.

TABLE 11

| Sample | Number of Peaks | Peak 1 Tm(° C.) | Δ(° C.) |
|---|---|---|---|
| 1s | 1 | 72 | — |
| 2s | 1 | 70 | 2 |
| 3s | 1 | 71 | 1 |
| 4s | 1 | 71 | 1 |
| 5s | 1 | 71 | 1 |
| 6s | 1 | 71 | 1 |
| 7s | 1 | 71 | 1 |
| 8s | 1 | 71 | 1 |
| 9s | 1 | 71 | 1 |
| 10s | 1 | 71 | 1 |
| 11s | 1 | 71 | 1 |
| 12s | 1 | 71 | 1 |
| 13s | 1 | 71 | 1 |
| 14s | 1 | 71 | 1 |
| 15s | 1 | 72 | 0 |
| 16s | x | 71 | 1 |
| 17s | 1 | 71 | 1 |

Example 4

In the present example. Tm analysis was performed in the presence of both a wild-type plasmid and a mutant-type plasmid to thereby detect the EGFR gene exon 19 polymorphism.

A partial sequence of the EGFR gene was prepared using a plasmid including the insertion of the oligonucleotides illustrated in Table 6. More specifically, an exon19 wild-type plasmid (ex19WT) including the insertion of wild-type oligonucleotide 1, an exon 19 mutant-type plasmid 2 (ex19mt2) including the insertion of mutant-type oligonucleotide 2, an exon19 mutant-type plasmid 4 (ex19mt4) including the insertion of mutant-type oligonucleotide 4, and an exon 19 mutant-type plasmid 6 (ex19mt6) including the insertion of mutant-type oligonucleotide 6 were prepared. The plasmids were mixed using the predetermined ratio shown in Table 12 to thereby prepare four samples. The samples were adjusted so that 250 plasmid copies are present per μL.

TABLE 12

| Sample | Respective Plasmid Mixing Ratios | | | |
|---|---|---|---|---|
| | ex19WT | ex19mt2 | ex19mt4 | ex19mt6 |
| ex19WT | 100% | 0% | 0% | 0% |
| ex19mt2 | 5% | 95% | 5% | 0% | 0% |
| ex19mt4 | 5% | 95% | 0% | 5% | 0% |
| ex19mt6 | 5% | 95% | 0% | 0% | 5% |

Tm analysis was performed in relation to 50 μL of the PCR reaction solution as illustrated in Table 13 using a fully automatic SNPs detection apparatus (product name: i-densy (trademark) IS-5310 manufactured by Arkray Inc.). PCR and Tm analysis were performed in the same manner as Example 1 with the exception that the detection wavelength was taken to be 520-555 nm and 585-700 nm.

TABLE 13

| (Composition of PCR Reaction Solution: units μL) | |
|---|---|
| Distilled water | 32.36 |
| 0.94 U/μL Taq polymerase | 2 |
| 10 w/v % NaN$_3$ | 0.23 |
| 100 mmol/L MgCl$_2$ | 0.75 |
| 1 mol/L KCl | 1.25 |
| 1 mol/L Tris-HCl (pH 8.6) | 1.25 |
| 2.5 mmol/L dNTP | 4 |
| 20 w/v % BSA | 0.5 |
| 80 w/v % glycerol | 1.56 |
| 100 μmol/L exon19 F primer | 0.5 |
| 100 μmol/L exon19 R primer | 1 |
| 100 μmol/L exon19 wild-type probe | 0.4 |
| 100 μmol/L exon19 mutant-type (del) probe | 0.2 |
| Sample | 4 |
| Total | 50 μL |

The exon19 primer sequence is shown below. The exon 19 probe used was the exon 19 wild-type probe and the exon 19 mutant-type (del) probe as described in Example 3.

```
                                   (SEQ ID NO: 18)
F primer (EGFR-EX19-F1)
5'-gatcccagaaggtgagaaag-3'

(SEQ ID NO: 20)
R primer (EGFR-EX19-R1)
5'-gaaactcacatcgaggatttc-3'

(SEQ ID NO: 5)
exon19 wild-type probe (5FL-EGFR-EX19-F2)
5'-(BODIPY FL)-cccgtcgctatcaaggaattaagagaagc-3'

(SEQ ID NO: 6)
exon19 mutant-type (del) probe
(3T-EGFR-EX19-No18-F1)
5'-agcaacaaaggaaatc-(TAMRA)-3'
```

Figure 3:
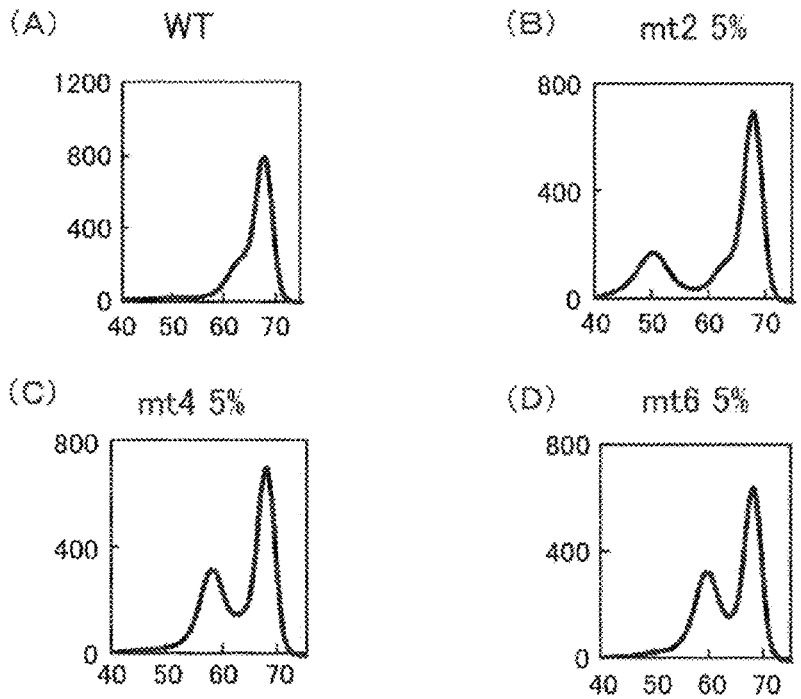
FIG. 3 depicts graphs (A)-(D) illustrating the results of Tm analysis of a reaction solution using different samples according to example 4 of the present invention.

The results are illustrated in FIG. 3. FIG. 3 is a graph of the Tm analysis showing the change in the fluorescent intensity associated with temperature increase. In FIG. 3, (A) is the result for ex19WT 100%, (B) is the result for ex19mt2 5%, (C) is the result for ex19mt4 5%, and (D) is the result for ex19mt6 5%. The horizontal axis shows the temperature (° C.) during measurement, and the vertical axis shows the change in the fluorescent intensity (hereinafter referred to as "fluorescent change amount"). The units are shown as "d fluorescent intensity increase amount/dt" (dF/dt). The Tm value of the ex19WT and exon19 wild-type probe is in proximity to 68° C., and the Tm value of the ex19mt2, the ex19mt4 and the ex19mt6 and exon19 mutant-type (del) probe is a lower temperature than the Tm value of the ex19WT and the exon 19 mutant-type (del) probe, and are respectively 51° C., 59° C., and 60° C.

As illustrated in FIG. 3(A), the ex19WT Tm value is the only confirmed peak for ex19WT 100%. On the other hand, as illustrated in FIGS. 3(B)-(D), peaks at two Tm values were confirmed in the samples that include the wild-type plasmid and the mutant-type plasmid. In other words, as illustrated in FIGS. 3(B)-(D), peaks were confirmed at both the Tm values for the wild-type ex19WT and the exon19 wild-type probe and at a lower temperature. In this manner, even when the wild-type and the mutant-type polymorphisms are mixed, use of the F primer, the R primer and the exon 19 probe according to the present example enables detection of the exon19 polymorphism by discrimination of the wild-type variant and the mutant-type variant.

Example 5

In the present example, Tm analysis was performed in the presence of both a wild-type plasmid and a mutant-type plasmid to thereby detect the EGFR gene EGFR858 polymorphism. The detection wavelength of PACIFIC BLUE is 445-480 nm, the detection wavelength of BODIPY is 520-555 nm, and the detection wavelength of TAMRA is 585-700 nm.

Example 5-1

The three samples from Example 1 (L858WT 100%, L858R 5%, and L858R 10%) were prepared. The samples were adjusted so that 250 plasmid copies are present per μL.

PCR and Tm analysis were performed in relation to 50 μL of PCR reaction solution as illustrated in Table 14 using a fully automatic SNPs detection apparatus (product name: i-densy (trademark) IS-5310 manufactured by Arkray Inc.). PCR repeated 50 cycles after processing at 95° C. for one minute with a single cycle being one second at 95° C. and 30 seconds at 60° C., followed by processing for one second at 95° C. and 60 seconds at 40° C. Then, the reaction solution was heated from 40° C. to 75° C. with a rate of temperature increase being 1° C./3 seconds to thereby perform Tm analysis by measurement of the change in the fluorescence intensity over time at a detection wavelength according to the fluorescent dye used in each probe.

TABLE 14

| (Composition of PCR Reaction Solution: units μL) | |
|---|---|
| Distilled water | 31.06 |
| 0.94 U/μL Taq polymerase | 2 |
| 10 w/v % NaN$_3$ | 0.23 |
| 100 mmol/L MgCl$_2$ | 0.75 |
| 1 mol/L KCl | 1.25 |
| 1 mol/L Tris-HCl (pH 8.6) | 1.25 |
| 2.5 mmol/L dNTP | 4 |
| 20 w/v % BSA | 0.5 |
| 80 w/v % glycerol | 1.56 |
| 100 μmol/L exon19 F primer | 0.5 |
| 100 μmol/L exon19 R primer | 1 |
| 100 μmol/L EGFR858 F primer | 0.5 |
| 100 μmol/L EGFR858 R primer | 0.25 |
| 100 μmol/L EGFR790 F primer | 0.5 |
| 100 μmol/L EGFR790 R primer | 0.25 |
| 100 μmol/L EGFR858 probe | 0.1 |
| 100 μmol/L exon19 probe | 0.2 |
| 100 μmol/L EGFR790 probe | 0.1 |
| Sample | 4 |
| Total | 50 μL |

The sequences of the F primer and the R primer are shown below.
(EGFR858 primer)

```
                                        (SEQ ID NO: 15)
F primer (EGFR-L858R-F2)
5'-aggaacgtactggtgaaaacaccgc-3'

(SEQ ID NO: 17)
R primer (EGFR-L858R-R1)
5'-gcctccttctgcatggtattctttctc-3'

(SEQ ID NO: 19)
(exon19 primer)
F primer (EGFR-EX19-F2)
5'-tctctctgtcatagggactc-3'

(SEQ ID NO: 20)
R primer (EGFR-EX19-R1)
5'-gaaactcacatcgaggatttc-3'

(SEQ ID NO: 25)
(EGFR790 primer)
F primer (EGFR-T790M-R1)
5'-tccaggaagcctacgtgatggccag-3'

(SEQ ID NO: 26)
R primer (EGFR-T790M-R1)
       5'-ccaatattgtctttgtgttcccggacatagtc-3'
```

The EGFR858 probe was an EGFR858 mutant-type probe (SEQ ID NO: 7) having the same sequence as that in Example 1 and labeled with PACIFIC BLUE in substitution for TAMRA. The exon19 probe was the exon19 wild-type probe (SEQ ID NO: 5) from Example 3. The EGFR790 probes were the probes having the sequences below. The EGFR790 mutant-type probe was a probe strongly hybridizes with the detection sequence in the sense strand of the EGFR790 mutant-type variant in the EGFR gene, and in that sequence, the underlined nucleotide is the nucleotide that is complementary to the EGFR790 mutant-type variant. The EGFR790 mutant-type probe was labeled at the 3' terminal with the fluorescent dye TAMRA.

```
                                        (SEQ ID NO: 7)
EGFR858 mutant-type probe (3PB-EGFR-858-R2)
5'-ttggcccgcccaaaatc-(PACIFIC BLUE)-3'

(SEQ ID NO: 5)
exon19 wild-type probe (5FL-EGFR-EX19-F2)
   5'-(BODIPY FL)-cccgtcgctatcaaggaattaagagaagc-3'

(SEQ ID NO: 23)
EGFR790 mutant-type probe (3T-EGFR-790M-mt-R3)
5'-tgagctgcatgatgaggtgcac-(TAMRA)-3'
```

Figure 4:
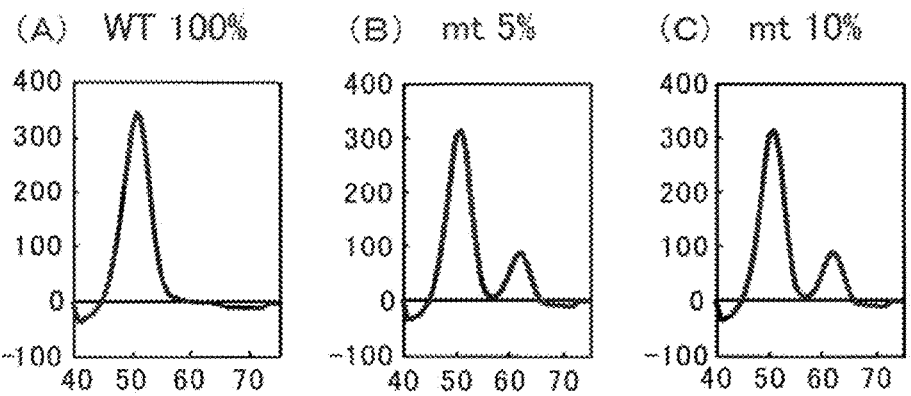
FIG. 4 depicts graphs (A)-(C) illustrating the results of Tm analysis of a reaction solution using different samples according to an example 5-1 of the present invention.

The results are illustrated in FIG. 4. FIG. 4 is a graph of the Tm analysis showing the change in the fluorescent intensity associated with temperature increase. In FIG. 4, (A) is the result for L858WT 100%, (B) is the result for L858R 5%, and (C) is the result for L858R 10%, and respectively, the results for detection of PACIFIC BLUE in the EGFR858 mutant-type probe are shown. The horizontal axis shows the temperature (° C.) during measurement, and the vertical axis shows the change in the fluorescent intensity (hereinafter referred to as "fluorescent change amount"). The units are shown as "d fluorescent intensity increase amount/dt" (dF/dt). The Tm value of the L958WT and EGFR858 mutant-type probe is in proximity to 51° C., and the Tm value of the L858R and EGFR858 mutant-type probe is in proximity to 61° C.

As illustrated in FIG. 4(A), the L858WT Tm value is the only confirmed peak for L858WT 100%. On the other hand, as illustrated in FIG. 4(C), peaks were confirmed at both the Tm value for L858WT and the Tm value for L858R for L858R 10% that includes 10% mutant-type plasmid. As illustrated in FIG. 4(B), peaks were confirmed at both the Tm value for L858WT and the Tm value for L858R for L858R 5% in which the content of the mutant-type plasmid is reduced to 5%.

Example 5-2

In the present example, the following three types of samples were used to execute PCR and Tm analysis in the same manner as Example 5-1 and thereby detect the exon 19 polymorphism in the EGFR gene with the exception that the detection wavelength was 525-555 nm.

The samples were prepared by mixing the exon 19 wild-type plasmid (ex19WT) and the exon19 mutant-type plasmid 6 (ex19 mt6) from Example 4 in the predetermined ratio illustrated below. The samples were adjusted so that 250 plasmid copies are present per μL.

TABLE 15

| Sample | | Respective Plasmid Mixing Ratios | |
|---|---|---|---|
| | | ex19WT | ex19mt6 |
| ex19WT | 100% | 100% | 0% |
| ex19mt6 | 5% | 95% | 5% |
| ex19mt6 | 10% | 90% | 10% |

Figure 5:
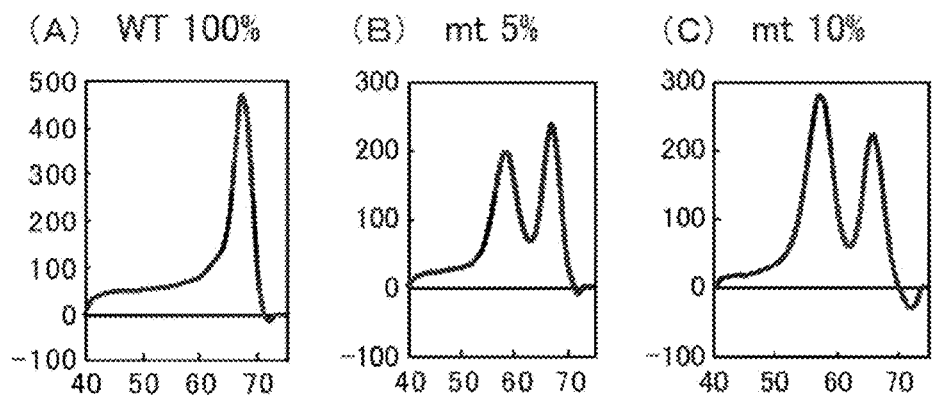
FIG. 5 depicts graphs (A)-(C) illustrating the results of Tm analysis of a reaction solution using different samples according to an example 5-2 of the present invention.

The results are illustrated in FIG. 5. FIG. 5 is a graph of the Tm analysis showing the change in the fluorescent intensity associated with temperature increase. In FIG. 5, (A) is the result for ex19WT 100%, (B) is the result for ex19mt6 5%, and (C) is the result for ex19mt6 10%, and respectively, the results for detection of BODIPY FL in the exon 19 wild-type probe are shown. The horizontal axis shows the temperature (° C.) during measurement, and the vertical axis shows the change in the fluorescent intensity (hereinafter referred to as "fluorescent change amount"). The units are shown as "d fluorescent intensity increase amount/dt" (dF/dt). The Tm value of the ex19WT and exon 19 wild-type probe is in proximity to 68° C., and the Tm value of the ex19mt6 and exon 19 wild-type probe is in proximity to 59° C.

As illustrated in FIG. 5(A), the ex19WT Tm value is the only confirmed peak for ex19WT 100%. On the other hand, as illustrated in FIG. 5(C), peaks were confirmed at both the Tm value for ex19WT and the Tm value for ex19mt6 for ex19 mt6 10% that includes 10% mutant-type plasmid. As illustrated in FIG. 5(B), peaks were confirmed at both the Tm value for ex19WT and the ex19mt6 Tm value for ex19mt6 5% in which the content of the mutant-type plasmid is reduced to 5%.

Example 5-3

In the present example, the following three types of samples were used to execute PCR and Tm analysis in the same manner as Example 5-1 and thereby detect the EGFR790 polymorphism in the EGFR gene with the exception that the detection wavelength was 585-700 nm.

The EGFR790 wild-type plasmid (T790WT) and the EGFR790 mutant-type plasmid (T790M) were prepared as the wild-type plasmid and the mutant-type plasmid. The EGFR790) wild-type plasmid (T790WT) includes a partial sequence of the EGFR gene being an insertion of the oligonucleotides from position 197 to position 496 of SEQ ID NO: 21, and the nucleotide (y) at position 347 of SEQ ID NO: 21 is cytosine (c). The EGFR790 mutant-type plasmid (T790M)

includes a partial sequence of the EGFR gene being an insertion of the oligonucleotides from position 197 to position 496 of SEQ ID NO: 21, and the nucleotide (y) at position 347 of SEQ ID NO: 21 is thymin (t). The plasmids were mixed using the predetermined ratio shown below to thereby prepare three samples. The samples were adjusted so that 250 plasmid copies are present per µL.

TABLE 16

| Sample | | Respective Plasmid Mixing Ratios | |
|---|---|---|---|
| | | T790WT | T790M |
| T790WT | 100% | 100% | 0% |
| T790M | 5% | 95% | 5% |
| T790M | 10% | 90% | 10% |

Figure 6:
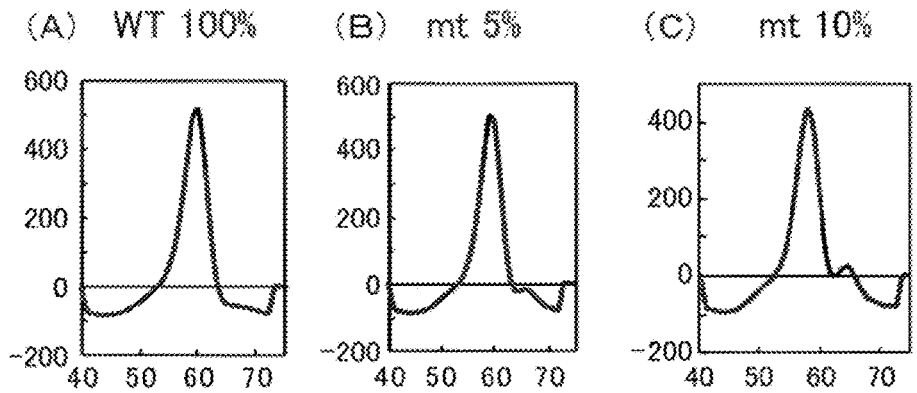
FIG. 6 depicts graphs (A)-(C) illustrating the results of Tm analysis of a reaction solution using different samples according to an example 5-3 of the present invention.

The results are illustrated in FIG. 6. FIG. 6 is a graph of the Tm analysis showing the change in the fluorescent intensity associated with temperature increase. In FIG. 6, (A) is the result for T790WT 100%, (B) is the result for T790M 5%, and (C) is the result for T790M 10%, and respectively, the results for detection of TAMRA in the EGFR790) mutant-type probe are shown. The horizontal axis shows the temperature (° C.) during measurement, and the vertical axis shows the change in the fluorescent intensity (hereinafter referred to as "fluorescent change amount"). The units are shown as "d fluorescent intensity increase amount/dt" (dF/dt). The Tm value of the T790WT and EGFR790 mutant-type probe is in proximity to 60° C., and the Tm value of the T790M and EGFR790) mutant-type probe is in proximity to 66° C.

As illustrated in FIG. 6(A), the T790WT Tm value is the only confirmed peak for T790WT 100%. On the other hand, as illustrated in FIG. 6(C), peaks at both the T790WT Tm value and the T790M Tm value were confirmed in T790M 10% that includes the 10% mutant-type plasmid. Furthermore, as illustrated in FIG. 6(B), peaks were confirmed at both the T790WT Tm value and the T790M Tm value for T790M 5% in which the content of the mutant-type plasmid is reduced to 5%.

Comparative Example 1

In the present example, the EGFR 858 polymorphism in the EGFR gene was detected in the same manner as Example 2 with the exception that the EGFR858 probe was the EGFR858 wild-type probe.

The EGFR858 wild-type probe is a probe that strongly hybridizes with the detection sequence in the sense strand of the EGFR858 wild-type variant of the EGFR gene, and in the sequence below, the underlined nucleotide is the nucleotide that is complementary to the EGFR858 wild-type variant. The EGFR858 wild-type probe was labeled at the 5' terminal with a fluorescent dye PACIFIC BLUE.

```
                                           (SEQ ID NO: 27)
EGFR858 wild-type probe (5PB-EGFR858861 WT-R1)
  5'-(PACIFIC BLUE)-ccagcagtttggccagc-3'
```

Figure 7:
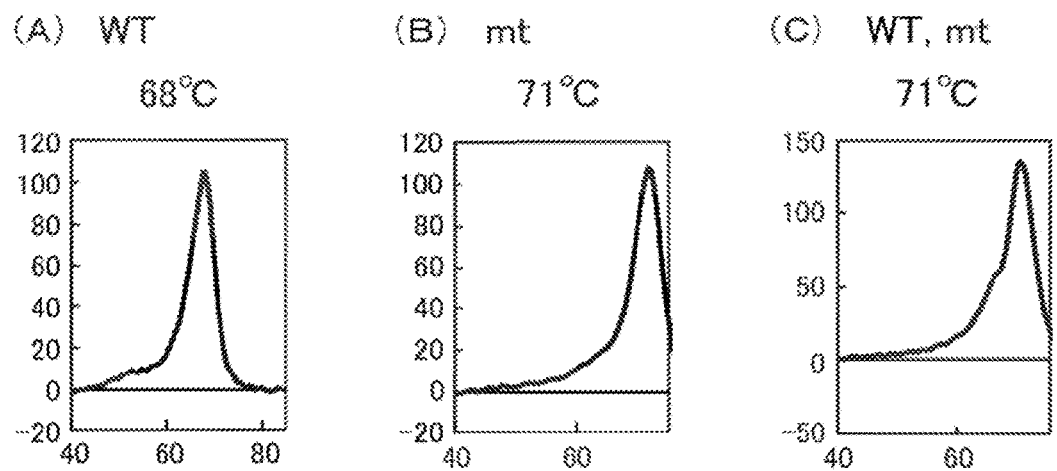
FIG. 7 depicts graphs (A)-(C) illustrating the results of Tm analysis of a reaction solution using different samples according to comparative example 1.

The results are illustrated in FIG. 7. FIG. 7 is a graph of the Tm analysis showing the change in the fluorescent intensity associated with temperature increase. In FIG. 7, (A) is the result for EGFR-L858R(WT)-F (SEQ ID NO: 32), (13) is the result for EGFR-L858R(MT)-F (SEQ ID NO: 33), and (C) is the result for a sample in which EGFR-L858R(WT)-F (SEQ ID NO: 32) and EGFR-L858R(MT)-F (SEQ ID NO: 33) are mixed in a ratio of 1:1. The horizontal axis shows the temperature (° C.) during measurement, and the vertical axis shows the change in the fluorescent intensity (hereinafter referred to as "fluorescent change amount"). The units are shown as "d fluorescent intensity increase amount/dt" (dF/dt).

As illustrated in FIG. 7(A), the L858WT 100% only exhibits a peak at 68° C., and as illustrated in FIG. 7(B), the L858R 100% only exhibits a peak at 71° C. However the difference between the temperatures of both peaks was 3° C., and that difference was small. Furthermore, as illustrated in FIG. 7(C), the mixed sample of EGFR-L858R(WT)-F (SEQ ID NO: 32) and EGFR-L858R(MT)-F (SEQ ID NO: 33) exhibits a temperature of 71° C. which overlaps with the peaks for L858WT and L858R and therefore detection of both peaks was not possible. Since the detection peak of the EGFR858 wild-type variant and the detection peak of the EGFR858 mutant-type variant are proximate, accurate detection is difficult when mixing the wild-type variant and the mutant-type variant.

Comparative Example 2

In the present example, four samples were used to detect the EGFR gene exon19 polymorphism in the same manner as Example 3 with the exception that the exon 19 wild-type probe was used as the exon 19 probe and the detection wavelength was 520-555 nm. The samples were prepared by adjusting the oligonucleotides 1, 2, 4 and 6 to 5 µmol/L. A sample 1 was the oligonucleotide 1 used in isolation, and a sample 2, a sample 4 and a sample 6 were prepared by mixing the oligonucleotide 1 with the oligonucleotides 2, 4 or 6 in a volume ratio of 1:5.

The exon19 wild-type probe is a probe that strongly hybridizes with the detection sequence in the antisense strand of the exon19 wild-type EGFR gene. In the sequence, the nucleotide that is underlined is the nucleotide that is complementary to the exon19 wild-type variant, and the exon19 wild-type probe was labeled with a fluorescent dye BODIPY FL at the 5' terminal.

```
                                             (SEQ ID NO: 28)
    exon19 wild-type probe (5FL-EGFR-EX19-WT-F1)
      5'-(BODIPY FL)-caaggaattaagagaagcaacatctccg-3'
```

Figure 8:
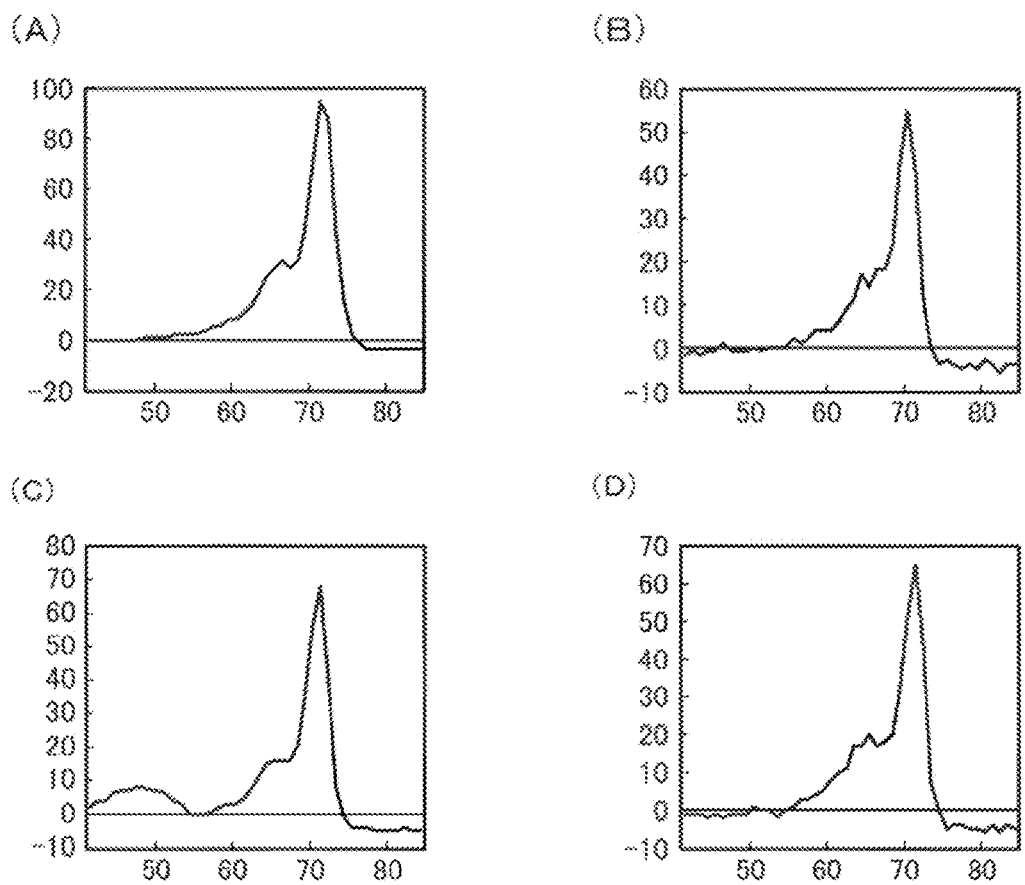
FIG. 8 depicts graphs (A)-(D) illustrating the results of Tm analysis of a reaction solution using different samples according to comparative example 2.

The results are illustrated in FIG. 8. FIG. 8 is a graph of the Tm analysis showing the change in the fluorescent intensity associated with temperature increase. FIG. 8 shows the results of using the exon 19 wild-type probe to obtain the detection results in relation to (A) sample 1, (B) sample 2, (C) sample 4, and (D) sample 6. The horizontal axis shows the temperature (° C.) during measurement, and the vertical axis shows the change in the fluorescent intensity (hereinafter referred to as "fluorescent change amount"). The units are shown as "d fluorescent intensity increase amount/dt" (dF/dt). The Tm value of oligonucleotide 1 and the exon 19 wild-type probe is proximate to 71° C., the Tm value of oligonucleotide 2 and the exon 19 wild-type probe is proximate to 71° C., the Tm value of oligonucleotide 4 and the exon 19 wild-type probe is proximate to 49° C., and the Tm value of oligonucleotide 6 and the exon 9 wild-type probe is proximate to 71° C.

As illustrated in FIG. 8(A), the Tm value for oligonucleotide 1 is the only confirmed peak for sample 1 which only contains wild-type oligonucleotide 1. As illustrated in FIG. 8(C), sample 4 which contains wild-type oligonucleotide 1 and mutant-type oligonucleotide 4 includes peaks that were confirmed at both the Tm value for wild-type oligonucleotide 1 and the Tm value for mutant-type oligonucleotide 4. However, as illustrated in FIGS. 8(B) and (D), although samples 2 and 6 that contain wild-type oligonucleotide 1 and mutant-type oligonucleotide 2 or 6 includes peaks that were confirmed at both the Tm value for wild-type oligonucleotide 1, a peak was not confirmed in relation to the Tm value for the respective mutant-type oligonucleotides.

Example 6

An EGFR858 polymorphism in an EGFR gene was detected in the same manner as Example 2 with the exception that Tm analysis was respectively executed in relation to the wild-type artificial nucleic acid and mutant-type artificial nucleic acid below using the probes illustrated in Table 17. In Table 17, the probes of SEQ ID NOs: 71 and 87 are probes that do not correspond to the probe of the present invention.

EGFR858 wild-type artificial nucleic acid (SEQ ID NO: 67: EGFR-L858R (WT)-F90) and EGFR858 mutant-type artificial nucleic acid (SEQ ID NO: 68: EGFR-L858R (MT)-F90) that are homologous to positions 217 to 306 SEQ ID NO: 1 were prepared. In the following two sequences, the underlined nucleotides correspond to the nucleotide at position 261 SEQ ID NO: 1. The respective artificial nucleic acids were adjusted to 5 µmol/L and were used as a 858 wild-type sample and a 858 mutant-type sample.

(SEQ ID NO: 67)
EGFR-L858R(WT)-F90
    actggtgaaaacaccgcagcatgtcaagatcacagattttgggctggc
caaactgctgggtgcggaagagaaagaataccatgcagaagg (SEQ ID NO: 68)
EGFR-L858R(MT)-F90
actggtgaaaacaccgcagcatgtcaagatcacagattttgggcgggc
caaactgctgggtgcggaagagaaagaataccatgcagaagg In the Tm analysis, the Tm value of a double-stranded nucleic acid composed of each of the probes and the wild-type sample and the Tm value of a double-stranded nucleic acid composed of each of the probes and the mutant-type sample were measured, and then the difference (ΔTm) therebetween was calculated. Then, on the basis of the calculated value, it was evaluated whether or not each probe can be judged as a wild-type or a mutant-type. The results are illustrated in Table 17.

(Evaluation Criteria)

○: ΔTm is at least 3° C. and judgment of whether a polymorphism is a wild-type or a mutant-type can be performed effectively, x: ΔTm is less than 3° C. and judgment of whether a polymorphism is a wild-type or a mutant-type cannot be performed effectively.

TABLE 17

|  |  | SEQ ID NO. | Name | Sequence (5'→3') | mer | Result |
|---|---|---|---|---|---|---|
| Comparative Example |  | 71 | 3T-EGFR-858-R3 | cCgcccaaaatctgtgatcttgacatgctgc-(TAMRA) | 31 | x |
| Example | P15-1 | 72 | 3T-EGFR-858-R4 | gccCgcccaaaatctgtgatcttgacatgc-(TAMRA) | 30 | ○ |
|  | P15-2 | 73 | 3T-EGFR-858-R5 | gccCgcccaaaatctgtgatcttgac-(TAMRA) | 26 | ○ |
|  | P15-3 | 74 | 3T-EGFR-858-R6 | tggccCgcccaaaatctgtgatc-(TAMRA) | 23 | ○ |
|  | P15-4 | 75 | 3T-EGFR-858-R7 | agcagtttggccCgcc-(TAMRA) | 16 | ○ |
|  | P15-5 | 76 | 3T-EGFR-858-R8 | acccagcagtttggccCgc-(TAMRA) | 19 | ○ |
|  | P16-1 | 77 | 5T-EGFR-858-R9 | (TAMRA)-ccCgcccaaaatctgtga | 18 | ○ |
|  | P16-2 | 78 | 5T-EGFR-858-R10 | (TAMRA)-cCgcccaaaatctgtgat | 18 | ○ |
|  | P16-3 | 79 | 5T-EGFR-858-R11 | (TAMRA)-cagtttggccCgcccaaaatct | 22 | ○ |
|  | P16-4 | 80 | 5T-EGFR-858-R12 | (TAMRA)-cagcagtttggccCgcccaaaa | 22 | ○ |
|  | P16-5 | 81 | 5T-EGFR-858-R13 | (TAMRA)-ccagcagtttggccCgcccaaaa | 23 | ○ |
|  | P16-6 | 82 | 5T-EGFR-858-R14 | (TAMRA)-cccagcagtttggccCgcccaaaa | 24 | ○ |
|  | P16-7 | 83 | 5T-EGFR-858-R15 | (TAMRA)-cacccagcagtttggccCgcccaa | 24 | ○ |
|  | P16-8 | 84 | 5T-EGFR-858-R16 | (TAMRA)-cgcacccagcagtttggccCgccc | 24 | ○ |
|  | P16-9 | 85 | 5T-EGFR-858-R17 | (TAMRA)-ccgcacccagcagtttggccCgcc | 24 | ○ |
|  | P16-10 | 86 | 5T-EGFR-858-R18 | (TAMRA)-cttccgcacccagcagtttggccCgcc | 27 | ○ |
| Example | P19 | 88 | 35T-EGFR-858-R21 | (TAMRA)-cagcagtttggccCgccc-(TAMRA) | 18 | ○ |
| Comparative Example |  | 87 | 5T-EGFR-858-R20 | (TAMRA)-ctttctcttccgcacccagcagtttggccCg | 31 | x |

As illustrated in Table 17, each of the probes of Examples showed one peak in relation to both the wild-type sample and the mutant-type sample and showed the Tm value with the mutant-type sample at least 3° C. higher than the Tm value with the wild-type sample (ΔTm≥3° C.). On the other hand, each of the probes of Comparative Examples showed one peak in relation to both the wild-type sample and the mutant-type sample but ΔTm was less than 3° C. From these, it was found out that, even in the common presence of the wild-type detection sequence and the mutant-type detection sequence, use of the probes of Examples enables effective judgment of the wild-type and the mutant-type.

Example 7

An EGFR858 polymorphism in an EGFR gene was detected in the same manner as Example 2 with the exception that Tm analysis was respectively executed in relation to the wild-type artificial nucleic acid and mutant-type artificial nucleic acid below using the probes illustrated in Table 18. In Table 18, the probe of SEQ ID NO: 93 is a probe that does not correspond to the probe of the present invention.

EGFR858 wild-type artificial nucleic acid (SEQ ID NO: 69: EGFR-L858R (WT)-R90) and EGFR858 mutant-type artificial nucleic acid (SEQ ID NO: 70: EGFR-L858R (MT)-R90) that are complementary to positions 217 to 306 SEQ ID NO: 1 were prepared. In the following two sequences, the underlined nucleotides correspond to the nucleotide at position 261 SEQ ID NO: 1. The respective artificial nucleic acids were adjusted to 5 μmol/L and were used as a EGFR 858 wild-type sample and a EGFR 858 mutant-type sample.

```
                                                       (SEQ ID NO: 69)
EGFR-L858(WT)-R90
ccttctgcatggtattctttctcttccgcacccagcagtttggccagc
ccaaaatctgtgatcttgacatgctgcggtgttttcaccagt (SEQ ID NO: 70)
EGFR-L858R(MT)-R90
ccttctgcatggtattctttctcttccgcacccagcagtttggcccgc
ccaaaatctgtgatcttgacatgctgcggtgttttcaccagt
```

In the Tm analysis, the Tm value of a double-stranded nucleic acid composed of each of the probes and the wild-type sample and the Tm value of a double-stranded nucleic acid composed of each of the probes and the mutant-type sample were measured. Each probe was evaluated in the same manner as Example 6. The results are illustrated in Table 18.

TABLE 18

| | | SEQ ID NO. | Name | Sequence (5'→3') | mer | Result |
|---|---|---|---|---|---|---|
| Example | P17-1 | 89 | 5T-EGFR-858-F1 | (TAMRA)-catgtcaagatcacagatttgggcGggc | 29 | ○ |
| | P17-2 | 90 | 5T-EGFR-858-F2 | (TAMRA)-caagatcacagatttgggcGggc | 24 | ○ |
| | P17-3 | 91 | 5T-EGFR-858-F3 | (TAMRA)-cacagatttgggcGggccaaa | 22 | ○ |
| | P17-4 | 92 | 5T-EGFR-858-F4 | (TAMRA)-cagatttgggcGggccaaa | 20 | ○ |
| Comparative Example | | 93 | 5T-EGFR-858-F5 | (TAMRA)-cGggccaaacTgctgggtgc | 20 | x |
| Example | P18-1 | 94 | 3T-EGFR-858-F6 | atcacagatttgggcGggc-(TAMRA) | 20 | ○ |
| | P18-2 | 95 | 3T-EGFR-858-F7 | atcacagatttgggcGggcc-(TAMRA) | 21 | ○ |
| | P18-3 | 96 | 3T-EGFR-858-F8 | attttgggcGggccaaac-(TAMRA) | 18 | ○ |
| | P18-4 | 97 | 3T-EGFR-858-F9 | attttgggcGggccaaacTgc-(TAMRA) | 21 | ○ |
| | P18-5 | 98 | 3T-EGFR-858-F10 | ggcGggccaaacTgctgggtgc-(TAMRA) | 22 | ○ |

As illustrated in Table 18, each of the probes of Examples showed one peak in relation to both the wild-type sample and the mutant-type sample and showed the Tm value with the mutant-type sample at least 3° C. higher than the Tm value with the wild-type sample (ΔTm≥3° C.). On the other hand, the probe of Comparative Example showed one peak in relation to both the wild-type sample and the mutant-type sample but ΔTm was less than 3° C. From these, it was found out that, even in the common presence of the wild-type detection sequence and the mutant-type detection sequence, use of the probes of Examples enables effective judgment of the wild-type and the mutant-type.

The results of Examples 1 to 7 and Comparative Examples 1 to 3 demonstrate that use of the F primer, the R primer and the probe according to each of the examples enables detection of the EGFR858 polymorphism, the exon19 polymorphism and the EGFR790 polymorphism in the EGFR gene by discrimination of the wild-type variant and the mutant-type variant for example even when wild-type variant and the mutant-type variant are mixed.

The method of detection of a polymorphism according to the present invention enables simple and highly reliable discrimination of a polymorphism in an EGFR gene for example by using of a probe for detection of a polymorphism according to the present invention. More specifically, even when the target polymorphism in a sample coexists in a wild-type EGFR gene and a mutant-type EGFR gene, simple and highly reliable detection is possible of the wild-type and mutant-type polymorphism. Furthermore, the primer according to the present invention for example enables specific amplification of the domain containing the EGFR gene polymorphism. In this manner, since the present invention enables the simple and highly reliable amplification and discrimination of the EGFR gene polymorphism, the detection results can be reflected in a selection of a therapeutic regime for disease and the present invention exhibits extreme utility in the field of medical care, or the like. Furthermore, the present invention enables application to the detection of a polymorphism in an EGFR gene in diverse areas including biochemistry in addition to medical fields.

The invention may be embodied in other forms without departing from the spirit or essential characteristics thereof.

The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

The invention claimed is:

1. A probe consisting of the nucleic acid sequence of SEQ ID NO: 6, and a fluorescent label attached to the nucleic acid sequence.

2. The probe according to claim 1, wherein the fluorescent label is attached to the 3' or 5' end of the nucleic acid sequence.

3. The probe according to claim 1, wherein the probe emits fluorescence when not hybridized to the target sequence, and the fluorescent intensity decreases when hybridized to the target sequence.

4. A kit for detecting a polymorphism in an EGFR gene, wherein the kit includes the probe according to claim 1.

5. The kit according to claim 4, further comprising a probe for detecting an EGFR exon20 T790M polymorphism.

6. The kit according to claim 4, further comprising a primer for amplifying a domain including a sequence hybridizing with at least one of the oligonucleotides according to P1, P3, and P15 to P19 in the nucleotide sequence of SEQ ID NO: 1 of the EGFR gene, wherein the oligonucleotide P1 comprises an oligonucleotide of 11 to 50 nucleotides complementary to nucleotides 251 to 261 of SEQ ID NO: 1;

the oligonucleotide P3 comprises an oligonucleotide of 5 to 50 nucleotides complementary to nucleotides 257 to 261 of SEQ ID NO: 1;

the oligonucleotide P15 comprises an oligonucleotide of 6 to 50 nucleotides complementary to nucleotides 259 to 264 of SEQ ID NO: 1;

the oligonucleotide P16 comprises an oligonucleotide of 5 to 50 nucleotides complementary to nucleotides 258 to 262 of SEQ ID NO: 1;

the oligonucleotide P17 is an oligonucleotide comprising a nucleotide sequence of 16 to 50 nucleotides comprising nucleotides 249 to 264 of SEQ ID NO: 1;

the oligonucleotide P18 is an oligonucleotide comprising a nucleotide sequence of 8 to 50 nucleotides comprising nucleotides 257 to 264 of SEQ ID NO: 1; and the oligonucleotide P19 comprises an oligonucleotide of 18 to 50 nucleotides complementary to nucleotides 257 to 274 of SEQ ID NO: 1.

7. The kit according to claim 6, wherein the primer consists of any of the sequences of SEQ ID NO: 15 to 20.

8. The kit according to claim 6, further comprising a probe for detecting an EGFR exon20 T790M polymorphism.

* * * * *

SEQUENCE LISTING

```
<160> NUMBER OF SEQ ID NOS: 66

<210> SEQ ID NO 1
<211> LENGTH: 410
<212> TYPE: DNA
<213> ORGANISM: Homo sapiens

<400> SEQUENCE: 1
ctttccattc tttggatcag tagtcactaa cgttcgccag ccataagtcc tcgacgtgga      60
gaggctcaga gcctggcatg aacatgaccc tgaattcgga tgcagagctt cttcccatga     120
tgatctgtcc ctcacagcag ggtcttctct gtttcagggc atgaactact tggaggaccg     180
tcgcttggtg caccgcgacc tggcagccag gaacgtactg gtgaaaacac cgcagcatgt     240
caagatcaca gattttgggc kggccaaacd gctgggtgcg gaagagaaag aataccatgc     300
agaaggaggc aaagtaagga ggtggcttta ggtcagccag cattttcctg acaccaggga     360
ccaggctgcc ttcccactag ctgtattgtt taacacatgc aggggaggat                 410

<210> SEQ ID NO 2
<211> LENGTH: 287
<212> TYPE: DNA
<213> ORGANISM: Homo sapiens

<400> SEQUENCE: 2
tcactgggca gcatgtggca ccatctcaca attgccagtt aacgtcttcc ttctctctct      60
gtcataggga ctctggatcc cagaaggtga gaaagttaaa attcccgtcg ctatcaagga     120
attaagagaa gcaacatctc cgaaagccaa caaggaaatc ctcgatgtga gtttctgctt     180
tgctgtgtgg gggtccatgg ctctgaacct caggcccacc ttttctcatg tctggcagct     240
gctctgctct agaccctgct catctccaca tcctaaatgt tcacttt                   287

<210> SEQ ID NO 3
<211> LENGTH: 272
<212> TYPE: DNA
<213> ORGANISM: Homo sapiens

<400> SEQUENCE: 3
tcactgggca gcatgtggca ccatctcaca attgccagtt aacgtcttcc ttctctctct      60
gtcataggga ctctggatcc cagaaggtga gaaagttaaa attcccgtcg ctatcaagga     120
attaagagaa gcaacaaagg aaatcctcga tgtgagtttc tgctttgctg tgtggggtc      180 catggctctg aacctcaggc ccaccttttc tcatgtctgg cagctgctct gctctagacc     240
ctgctcatct ccacatccta aatgttcact tt                                   272

<210> SEQ ID NO 4
<211> LENGTH: 33
<212> TYPE: DNA
<213> ORGANISM: Artificial
<220> FEATURE:
<223> OTHER INFORMATION: probe

<400> SEQUENCE: 4
cccgtcgcta tcaagtaatt aagagaagca aca                                   33
```

<210> SEQ ID NO 5
<211> LENGTH: 29
<212> TYPE: DNA
<213> ORGANISM: Artificial
<220> FEATURE:
<223> OTHER INFORMATION: probe

<400> SEQUENCE: 5
cccgtcgcta tcaaggaatt aagagaagc                             29

<210> SEQ ID NO 6
<211> LENGTH: 16
<212> TYPE: DNA
<213> ORGANISM: Artificial
<220> FEATURE:
<223> OTHER INFORMATION: probe

<400> SEQUENCE: 6
agcaacaaag gaaatc                                           16

<210> SEQ ID NO 7
<211> LENGTH: 17
<212> TYPE: DNA
<213> ORGANISM: Artificial
<220> FEATURE:
<223> OTHER INFORMATION: probe

<400> SEQUENCE: 7
ttggcccgcc caaaatc                                          17

<210> SEQ ID NO 8
<211> LENGTH: 17
<212> TYPE: DNA
<213> ORGANISM: Artificial
<220> FEATURE:
<223> OTHER INFORMATION: probe

<400> SEQUENCE: 8
ttggccagcc caaaatc                                          17

<210> SEQ ID NO 9
<211> LENGTH: 15
<212> TYPE: DNA
<213> ORGANISM: Artificial
<220> FEATURE:
<223> OTHER INFORMATION: probe

<400> SEQUENCE: 9
cagtttggcc cgccc                                            15

<210> SEQ ID NO 10
<211> LENGTH: 15
<212> TYPE: DNA
<213> ORGANISM: Artificial
<220> FEATURE:
<223> OTHER INFORMATION: probe

<400> SEQUENCE: 10
ctgtttggcc cgccc                                            15

<210> SEQ ID NO 11
<211> LENGTH: 15
<212> TYPE: DNA
<213> ORGANISM: Artificial
<220> FEATURE:

```
<223> OTHER INFORMATION: probe

<400> SEQUENCE: 11
ccgtttggcc cgccc                                                        15

<210> SEQ ID NO 12
<211> LENGTH: 15
<212> TYPE: DNA
<213> ORGANISM: Artificial
<220> FEATURE:
<223> OTHER INFORMATION: probe

<400> SEQUENCE: 12
cagtttggcc agccc                                                        15

<210> SEQ ID NO 13
<211> LENGTH: 15
<212> TYPE: DNA
<213> ORGANISM: Artificial
<220> FEATURE:
<223> OTHER INFORMATION: probe

<400> SEQUENCE: 13
ctgtttggcc agccc                                                        15

<210> SEQ ID NO 14
<211> LENGTH: 15
<212> TYPE: DNA
<213> ORGANISM: Artificial
<220> FEATURE:
<223> OTHER INFORMATION: probe

<400> SEQUENCE: 14
ccgtttggcc agccc                                                        15

<210> SEQ ID NO 15
<211> LENGTH: 25
<212> TYPE: DNA
<213> ORGANISM: Artificial
<220> FEATURE:
<223> OTHER INFORMATION: primer

<400> SEQUENCE: 15
aggaacgtac tggtgaaaac accgc                                             25

<210> SEQ ID NO 16
<211> LENGTH: 28
<212> TYPE: DNA
<213> ORGANISM: Artificial
<220> FEATURE:
<223> OTHER INFORMATION: primer

<400> SEQUENCE: 16
ttactttgcc tccttctgca tggtattc                                          28

<210> SEQ ID NO 17
<211> LENGTH: 27
<212> TYPE: DNA
<213> ORGANISM: Artificial
<220> FEATURE:
<223> OTHER INFORMATION: primer

<400> SEQUENCE: 17
gcctccttct gcatggtatt ctttctc                                           27
```

```
<210> SEQ ID NO 18
<211> LENGTH: 20
<212> TYPE: DNA
<213> ORGANISM: Artificial
<220> FEATURE:
<223> OTHER INFORMATION: primer

<400> SEQUENCE: 18
gatcccagaa ggtgagaaag                                                    20

<210> SEQ ID NO 19
<211> LENGTH: 20
<212> TYPE: DNA
<213> ORGANISM: Artificial
<220> FEATURE:
<223> OTHER INFORMATION: forward primer

<400> SEQUENCE: 19
tctctctgtc atagggactc                                                    20

<210> SEQ ID NO 20
<211> LENGTH: 21
<212> TYPE: DNA
<213> ORGANISM: Artificial
<220> FEATURE:
<223> OTHER INFORMATION: reverse primer

<400> SEQUENCE: 20
gaaactcaca tcgaggattt c                                                  21

<210> SEQ ID NO 21
<211> LENGTH: 1020
<212> TYPE: DNA
<213> ORGANISM: Homo sapiens

<400> SEQUENCE: 21
tggccactgt tgcctgggcc tctctgtcat ggggaatccc cagatgcacc caggaggggc          60
cctctcccac tgcatctgtc acttcacagc cctgcgtaaa cgtccctgtg ctaggtcttt         120
tgcaggcaca gcttttcctc catgagtacg tattttgaaa ctcaagatcg cattcatgcg         180
tcttcacctg aaggggtcc atgtgcccct ccttctggcc accatgcgaa gccacactga          240
cgtgcctctc cctccctcca ggaagcctac gtgatggcca gcgtggacaa ccccacgtg          300
tgccgcctgc tgggcatctg cctcacctcc accgtgcagc tcatcaygca gctcatgccc         360
ttcggctgcc tcctggacta tgtccgggaa cacaaagaca atattggctc ccagtacctg         420
ctcaactggt gtgtgcagat cgcaaaggta atcagggaag ggagatacgg ggagggggaga        480
taaggagcca ggatcctcac atgcggtctg cgctcctggg atagcaagag tttgccatgg         540
ggatatgtgt gtgcgtgcat gcagcacaca cacattcctt tattttggat tcaatcaagt         600
tgatcttctt gtgcacaaat cagtgcctgt cccatctgca tgtggaaact ctcatcaatc         660
agctaccttt gaagaatttt ctctttattg agtgctcagt gtggtctgat gtctctgttc         720
ttatttctct ggaattcttt gtgaatactg tggtgatttg tagtggagaa ggaatattgc         780
ttccccatt caggacttga taacaaggta agcaagccag gccaaggcca ggaggaccca          840
ggtgatagtg gtggagtgga gcaggtgcct tgcaggaggc ccagtgagga ggtgcaagga         900
gctgacagag ggcgcagctg ctgctgctat gtggctgggg ccttggctaa gtgtccccct         960
ttccacaggc tcgctccaga gccagggcgg ggctgagaga gcagagtggt caggtagccc        1020

<210> SEQ ID NO 22
```

```
<211> LENGTH: 22
<212> TYPE: DNA
<213> ORGANISM: Artificial
<220> FEATURE:
<223> OTHER INFORMATION: probe

<400> SEQUENCE: 22
tgagctgcrt gatgaggtgc ac                                          22

<210> SEQ ID NO 23
<211> LENGTH: 22
<212> TYPE: DNA
<213> ORGANISM: Artificial
<220> FEATURE:
<223> OTHER INFORMATION: probe

<400> SEQUENCE: 23
tgagctgcat gatgaggtgc ac                                          22

<210> SEQ ID NO 24
<211> LENGTH: 22
<212> TYPE: DNA
<213> ORGANISM: Artificial
<220> FEATURE:
<223> OTHER INFORMATION: probe

<400> SEQUENCE: 24
tgagctgcgt gatgaggtgc ac                                          22

<210> SEQ ID NO 25
<211> LENGTH: 25
<212> TYPE: DNA
<213> ORGANISM: Artificial
<220> FEATURE:
<223> OTHER INFORMATION: foward primer

<400> SEQUENCE: 25
tccaggaagc ctacgtgatg gccag                                       25

<210> SEQ ID NO 26
<211> LENGTH: 32
<212> TYPE: DNA
<213> ORGANISM: Artificial
<220> FEATURE:
<223> OTHER INFORMATION: reverse primer

<400> SEQUENCE: 26
ccaatattgt ctttgtgttc ccggacatag tc                               32

<210> SEQ ID NO 27
<211> LENGTH: 17
<212> TYPE: DNA
<213> ORGANISM: Artificial
<220> FEATURE:
<223> OTHER INFORMATION: probe

<400> SEQUENCE: 27
ccagcagttt ggccagc                                                17

<210> SEQ ID NO 28
<211> LENGTH: 28
<212> TYPE: DNA
<213> ORGANISM: Artificial
<220> FEATURE:
<223> OTHER INFORMATION: probe

<400> SEQUENCE: 28
```
caaggaatta agagaagcaa catctccg                                28

<210> SEQ ID NO 29
<211> LENGTH: 61
<212> TYPE: DNA
<213> ORGANISM: Homo sapiens

<400> SEQUENCE: 29
cccgtcgcta tcaaggaatt aagagaagca acatctccga aagccaacaa ggaaatcctc    60
g                                                                   61

<210> SEQ ID NO 30
<211> LENGTH: 33
<212> TYPE: DNA
<213> ORGANISM: Homo sapiens

<400> SEQUENCE: 30
cccgtcgcta tcaaaacatc tccgaaagcc aac                           33

<210> SEQ ID NO 31
<211> LENGTH: 45
<212> TYPE: DNA
<213> ORGANISM: Homo sapiens

<400> SEQUENCE: 31
cccgtcgcta tcaagacatc tccgaaagcc aaaaggaaat cctcg              45

<210> SEQ ID NO 32
<211> LENGTH: 50
<212> TYPE: DNA
<213> ORGANISM: Homo sapiens

<400> SEQUENCE: 32
caagatcaca gattttgggc tggccaaact gctgggtgcg gaagagaaag         50

<210> SEQ ID NO 33
<211> LENGTH: 50
<212> TYPE: DNA
<213> ORGANISM: Homo sapiens

<400> SEQUENCE: 33
caagatcaca gattttgggc gggccaaact gctgggtgcg gaagagaaag         50

<210> SEQ ID NO 34
<211> LENGTH: 52
<212> TYPE: DNA
<213> ORGANISM: Homo sapiens

<400> SEQUENCE: 34
cccgtcgcta tcaaggaacc aacatctccg aaagccaaca aggaaatcct cg      52

<210> SEQ ID NO 35
<211> LENGTH: 46
<212> TYPE: DNA
<213> ORGANISM: Homo sapiens

<400> SEQUENCE: 35
cccgtcgcta tcaaggaatc tccgaaagcc aacaaggaaa tcctcg             46

<210> SEQ ID NO 36
<211> LENGTH: 43
<212> TYPE: DNA

<213> ORGANISM: Homo sapiens

<400> SEQUENCE: 36
cccgtcgcta tcaaggaatc gaaagccaac aaggaaatcc tcg    43

<210> SEQ ID NO 37
<211> LENGTH: 49
<212> TYPE: DNA
<213> ORGANISM: Homo sapiens

<400> SEQUENCE: 37
cccgtcgcta tcaaggaacc atctccgaaa gccaacaagg aaatcctcg    49

<210> SEQ ID NO 38
<211> LENGTH: 43
<212> TYPE: DNA
<213> ORGANISM: Homo sapiens

<400> SEQUENCE: 38
cccgtcgcta tcaaggaacc gaaagccaac aaggaaatcc tcg    43

<210> SEQ ID NO 39
<211> LENGTH: 43
<212> TYPE: DNA
<213> ORGANISM: Homo sapiens

<400> SEQUENCE: 39
cccgtcgcta tcaaggttcc gaaagccaac aaggaaatcc tcg    43

<210> SEQ ID NO 40
<211> LENGTH: 49
<212> TYPE: DNA
<213> ORGANISM: Homo sapiens

<400> SEQUENCE: 40
cccgtcgcta tcaaggaatc atctccgaaa gccaacaagg aaatcctcg    49

<210> SEQ ID NO 41
<211> LENGTH: 43
<212> TYPE: DNA
<213> ORGANISM: Homo sapiens

<400> SEQUENCE: 41
cccgtcgcta tcaaggaatc gaaagccaac aaggaaatcc tcg    43

<210> SEQ ID NO 42
<211> LENGTH: 43
<212> TYPE: DNA
<213> ORGANISM: Homo sapiens

<400> SEQUENCE: 42
cccgtcgcta tcaaggaaca gaaagccaac aaggaaatcc tcg    43

<210> SEQ ID NO 43
<211> LENGTH: 46
<212> TYPE: DNA
<213> ORGANISM: Homo sapiens

<400> SEQUENCE: 43
cccgtcgcta tcaaggtatc tccgaaagcc aacaaggaaa tcctcg    46

<210> SEQ ID NO 44
<211> LENGTH: 43

<212> TYPE: DNA
<213> ORGANISM: Homo sapiens

<400> SEQUENCE: 44
cccgtcgcta tcaaggttcc gaaagccaac aaggaaatcc tcg         43

<210> SEQ ID NO 45
<211> LENGTH: 44
<212> TYPE: DNA
<213> ORGANISM: Homo sapiens

<400> SEQUENCE: 45
cccgtcgcta tcaaaatctc cgaaagccaa caaggaaatc ctcg        44

<210> SEQ ID NO 46
<211> LENGTH: 46
<212> TYPE: DNA
<213> ORGANISM: Homo sapiens

<400> SEQUENCE: 46
cccgtcgcaa ttaagatatc tccgaaagcc aacaaggaaa tcctcg      46

<210> SEQ ID NO 47
<211> LENGTH: 46
<212> TYPE: DNA
<213> ORGANISM: Homo sapiens

<400> SEQUENCE: 47
cccgtcgcta tcaaggaaca accgaaagcc aacaaggaaa tcctcg      46

<210> SEQ ID NO 48
<211> LENGTH: 46
<212> TYPE: DNA
<213> ORGANISM: Homo sapiens

<400> SEQUENCE: 48
cccgtcgcta tcaaggaatt aagagaagca acaaaggaaa tcctcg      46

<210> SEQ ID NO 49
<211> LENGTH: 60
<212> TYPE: DNA
<213> ORGANISM: Homo sapiens

<400> SEQUENCE: 49
ttccttgttg gctttcggag atgttgcttc tcttaattcc ttgatagcga cgggaatttt    60

<210> SEQ ID NO 50
<211> LENGTH: 60
<212> TYPE: DNA
<213> ORGANISM: Homo sapiens

<400> SEQUENCE: 50
tcgaggattt ccttgttggc tttcggagat gttttgatag cgacgggaat tttaactttc    60

<210> SEQ ID NO 51
<211> LENGTH: 60
<212> TYPE: DNA
<213> ORGANISM: Homo sapiens

<400> SEQUENCE: 51
tcgaggattt ccttgttggc tttcggagat gtcttgatag cgacgggaat tttaactttc    60

<210> SEQ ID NO 52

```
<211> LENGTH: 60
<212> TYPE: DNA
<213> ORGANISM: Homo sapiens

<400> SEQUENCE: 52
gatttccttg ttggctttcg gagatgttgg ttccttgata gcgacgggaa ttttaacttt      60

<210> SEQ ID NO 53
<211> LENGTH: 60
<212> TYPE: DNA
<213> ORGANISM: Homo sapiens

<400> SEQUENCE: 53
tcgaggattt ccttgttggc tttcggagat tccttgatag cgacgggaat tttaactttc      60

<210> SEQ ID NO 54
<211> LENGTH: 60
<212> TYPE: DNA
<213> ORGANISM: Homo sapiens

<400> SEQUENCE: 54
atcgaggatt ccttgttgg ctttcgattc cttgatagcg acgggaattt taactttctc      60

<210> SEQ ID NO 55
<211> LENGTH: 60
<212> TYPE: DNA
<213> ORGANISM: Homo sapiens

<400> SEQUENCE: 55
aggatttcct tgttggcttt cggagatggt tccttgatag cgacgggaat tttaactttc      60

<210> SEQ ID NO 56
<211> LENGTH: 60
<212> TYPE: DNA
<213> ORGANISM: Homo sapiens

<400> SEQUENCE: 56
catcgaggat ttccttgttg ctttcggtt ccttgatagc gacgggaatt ttaactttct      60

<210> SEQ ID NO 57
<211> LENGTH: 60
<212> TYPE: DNA
<213> ORGANISM: Homo sapiens

<400> SEQUENCE: 57
catcgaggat ttccttgttg ctttcggaa ccttgatagc gacgggaatt ttaactttct      60

<210> SEQ ID NO 58
<211> LENGTH: 60
<212> TYPE: DNA
<213> ORGANISM: Homo sapiens

<400> SEQUENCE: 58
ggatttcctt gttggctttc ggagatgatt ccttgatagc gacgggaatt ttaactttct      60

<210> SEQ ID NO 59
<211> LENGTH: 60
<212> TYPE: DNA
<213> ORGANISM: Homo sapiens
```

<400> SEQUENCE: 59
catcgaggat tccttgttg gctttcgatt ccttgatagc gacgggaatt ttaactttct    60

<210> SEQ ID NO 60
<211> LENGTH: 60
<212> TYPE: DNA
<213> ORGANISM: Homo sapiens

<400> SEQUENCE: 60
catcgaggat tccttgttg gctttctgtt ccttgatagc gacgggaatt ttaactttct    60

<210> SEQ ID NO 61
<211> LENGTH: 60
<212> TYPE: DNA
<213> ORGANISM: Homo sapiens

<400> SEQUENCE: 61
tcgaggattt ccttgttggc tttcggagat accttgatag cgacgggaat tttaactttc    60

<210> SEQ ID NO 62
<211> LENGTH: 60
<212> TYPE: DNA
<213> ORGANISM: Homo sapiens

<400> SEQUENCE: 62
acatcgagga tttccttgtt ggctttcgga accttgatag cgacgggaat tttaactttc    60

<210> SEQ ID NO 63
<211> LENGTH: 60
<212> TYPE: DNA
<213> ORGANISM: Homo sapiens

<400> SEQUENCE: 63
acatcgagga tttccttgtt ggctttcgga attttgatag cgacgggaat tttaactttc    60

<210> SEQ ID NO 64
<211> LENGTH: 60
<212> TYPE: DNA
<213> ORGANISM: Homo sapiens

<400> SEQUENCE: 64
tcgaggattt ccttgttggc tttcggagat atcttaattg cgacgggaat tttaactttc    60

<210> SEQ ID NO 65
<211> LENGTH: 60
<212> TYPE: DNA
<213> ORGANISM: Homo sapiens

<400> SEQUENCE: 65
tcgaggattt ccttgttggc tttcggttgt tccttgatag cgacgggaat tttaactttc    60

<210> SEQ ID NO 66
<211> LENGTH: 60
<212> TYPE: DNA
<213> ORGANISM: Homo sapiens

<400> SEQUENCE: 66
cgaggatttc ctttgttgct tctcttaatt ccttgatagc gacgggaatt ttaactttct    60